United States Patent
Bonny

(10) Patent No.: US 8,236,924 B2
(45) Date of Patent: Aug. 7, 2012

(54) CELL-PERMEABLE PEPTIDE INHIBITORS OF THE JNK SIGNAL TRANSDUCTION PATHWAY

(75) Inventor: Christophe Bonny, Lausanne (CH)

(73) Assignee: Xigen SA, Lausanne (CH)

( * ) Notice: Subject to any disclaimer, the term of this patent is extended or adjusted under 35 U.S.C. 154(b) by 994 days.

(21) Appl. No.: 12/101,911

(22) Filed: Apr. 11, 2008

(65) Prior Publication Data
US 2009/0069234 A1    Mar. 12, 2009

Related U.S. Application Data

(62) Division of application No. 10/457,614, filed on Jun. 9, 2003, now abandoned.

(51) Int. Cl.
*A61K 38/00* (2006.01)
*A61P 17/14* (2006.01)
(52) U.S. Cl. ......... 530/300; 530/324; 514/1.1; 514/20.7
(58) Field of Classification Search .................. None
See application file for complete search history.

(56) References Cited

U.S. PATENT DOCUMENTS

| | | | |
|---|---|---|---|
| 4,631,211 A | 12/1986 | Houghten | |
| 4,698,327 A | 10/1987 | Nagarajan et al. | |
| 4,732,890 A | 3/1988 | Bonelli et al. | |
| 5,169,933 A | 12/1992 | Anderson et al. | |
| 5,597,895 A | 1/1997 | Gaynor et al. | |
| 5,670,617 A | 9/1997 | Frankel et al. | |
| 5,672,479 A | 9/1997 | Johnson et al. | |
| 5,674,980 A | 10/1997 | Frankel et al. | |
| 5,686,264 A | 11/1997 | Gaynor et al. | |
| 5,747,641 A | 5/1998 | Frankel et al. | |
| 5,756,684 A | 5/1998 | Johnson et al. | |
| 5,804,604 A | 9/1998 | Frankel et al. | |
| 5,840,313 A | 11/1998 | Vahlne et al. | |
| 5,880,261 A | 3/1999 | Waeber et al. | |
| 5,989,814 A | 11/1999 | Frankel et al. | |
| 5,994,108 A | 11/1999 | Gaynor et al. | |
| 5,994,109 A | 11/1999 | Woo et al. | |
| 6,043,083 A | 3/2000 | Davis et al. | |
| 6,117,632 A | 9/2000 | O'Mahony | |
| 6,265,386 B1 * | 7/2001 | Campbell | 514/36 |
| 6,284,456 B1 | 9/2001 | Jones et al. | |
| 6,300,317 B1 | 10/2001 | Szoka et al. | |
| 6,316,003 B1 | 11/2001 | Frankel et al. | |
| 6,348,185 B1 | 2/2002 | Piwnica-Worms | |
| 6,448,283 B1 | 9/2002 | Ylikoski et al. | |
| 6,495,663 B1 | 12/2002 | Rothbard et al. | |
| 6,586,403 B1 | 7/2003 | Mathison et al. | |
| 6,610,820 B1 * | 8/2003 | Bonny | 530/300 |
| 6,630,351 B1 | 10/2003 | Monahan et al. | |
| 6,653,443 B2 | 11/2003 | Zhang et al. | |
| 6,740,524 B1 | 5/2004 | Akuta et al. | |
| 6,780,970 B2 * | 8/2004 | Bonny | 530/324 |
| 6,881,825 B1 | 4/2005 | Robbins et al. | |
| 6,960,648 B2 | 11/2005 | Bonny | |
| 7,034,109 B2 | 4/2006 | Bonny | |
| 2002/0103229 A1 | 8/2002 | Bhagwat et al. | |
| 2003/0100549 A1 | 5/2003 | Salituro et al. | |
| 2003/0104622 A1 | 6/2003 | Robbins et al. | |
| 2003/0108539 A1 | 6/2003 | Bonny | |
| 2003/0124113 A1 | 7/2003 | Hillman et al. | |
| 2003/0220480 A1 | 11/2003 | Bonny | |
| 2004/0082509 A1 | 4/2004 | Bonny | |
| 2004/0265879 A1 | 12/2004 | Iversen et al. | |
| 2005/0059597 A1 | 3/2005 | Tymianski | |
| 2005/0106695 A1 | 5/2005 | Bonny | |
| 2006/0223807 A1 | 10/2006 | Davis et al. | |
| 2006/0258706 A1 | 11/2006 | Saindane | |
| 2006/0270646 A1 | 11/2006 | Graczyk et al. | |
| 2007/0003531 A1 | 1/2007 | Mukherji et al. | |
| 2008/0008749 A1 | 1/2008 | Pearlman et al. | |

FOREIGN PATENT DOCUMENTS

| | | |
|---|---|---|
| EP | 0 679 716 A1 | 11/1995 |
| EP | 0 897 002 A2 | 2/1999 |
| EP | 1 364 949 A1 | 11/2003 |
| JP | 58-146538 | 9/1983 |
| JP | 02-221294 | 4/1990 |
| JP | 7-503617 | 4/1995 |
| WO | 92-18138 A1 | 10/1992 |
| WO | 93-18759 A1 | 9/1993 |
| WO | 94-04562 A1 | 3/1994 |
| WO | 94-05311 A1 | 3/1994 |
| WO | WO 94/04686 | 3/1994 |
| WO | 94-23751 A1 | 10/1994 |
| WO | WO 95/34295 | 12/1995 |
| WO | WO 97/05265 | 2/1997 |
| WO | WO 97/10836 | 3/1997 |
| WO | WO 98/11907 | 3/1998 |
| WO | 98-23781 A1 | 6/1998 |
| WO | 98-44106 A1 | 10/1998 |
| WO | 98-47913 A1 | 10/1998 |

(Continued)

OTHER PUBLICATIONS

Piroli et. al. Rescue of Hearing, Auditory Hair Cells, and Neurons by CEP-1347/KT7515, and Inhibitor of c-Jun N-Terminal Kinase Activation, The Journal of Neuroscience, Jan. 1, 2001 20 (1): 43-50.*
Pirvola (Rescue of Hearing, Auditory Hair Cells, and Neurons by CEP-1347/KT7515, and Inhibitor of c-Jun N-Terminal Kinase Activation, The Journal of Neuroscience, Jan. 1, 2001 20 (1): 43-50.*
Inhibit.Dictionary.com. The American Heritage® Stedman's Medical Dictionary, Houghton Mifflin Company, internet document http://dictionary.reference.com/browse/inhibit, accessed: Oct. 10, 2007, 1 page.
J. Rudinger, In: Peptide Hormones, JA Parsons, Ed. (1976) 1-7.
D. Voet and J.G. Voet, Biochemistry, 2nd Edition.(1995), pp. 235-241.
D.E. Smilek, et at. Proc. Natl. Acad. Sci. USA (1991) 88, pp. 9633-9637.
W.S. Messer, "Vasopressin and Oxytocin", web document updated Apr. 3, 2000; http://www.neurosci.pharm.utoledo.edu/MBC3320/vasopressin.htm; 5 pages.

(Continued)

Primary Examiner — Christina Bradley
Assistant Examiner — Jeanette Lieb
(74) Attorney, Agent, or Firm — Morgan Lewis & Bockius LLP

(57) ABSTRACT

The invention provides cell-permeable peptides that bind to JNK proteins and inhibit JNK-mediated effects in JNK-expressing cells.

21 Claims, 21 Drawing Sheets

FOREIGN PATENT DOCUMENTS

| | | | |
|---|---|---|---|
| WO | 98-51325 | A2 | 11/1998 |
| WO | 98-51825 | A1 | 11/1998 |
| WO | WO 98/49188 | | 11/1998 |
| WO | WO 98/52614 | | 11/1998 |
| WO | 99-07728 | A2 | 2/1999 |
| WO | 99-16787 | A1 | 4/1999 |
| WO | 99-50282 | A2 | 10/1999 |
| WO | WO 99/49879 | | 10/1999 |
| WO | 99-58561 | A1 | 11/1999 |
| WO | 99-67284 | A2 | 12/1999 |
| WO | 00-12587 | A2 | 3/2000 |
| WO | 00-41719 | A1 | 7/2000 |
| WO | 01-10888 | A1 | 2/2001 |
| WO | 01-13957 | A2 | 3/2001 |
| WO | 01-15511 | A2 | 3/2001 |
| WO | WO 0127268 | A2 * | 4/2001 |
| WO | 02-31109 | A2 | 4/2002 |
| WO | 02-061105 | A2 | 8/2002 |
| WO | 02-062396 | A2 | 8/2002 |
| WO | 02-065986 | A2 | 8/2002 |
| WO | 02-069930 | A1 | 9/2002 |
| WO | 02-081504 | A2 | 10/2002 |
| WO | 02-081505 | A2 | 10/2002 |
| WO | 03-075917 | A1 | 9/2003 |
| WO | 03-103698 | A1 | 12/2003 |
| WO | 03-103718 | A2 | 12/2003 |
| WO | 2004-022580 | A2 | 3/2004 |
| WO | 2004-035793 | A1 | 4/2004 |
| WO | 2004-045535 | A2 | 6/2004 |
| WO | 2004-054501 | A2 | 7/2004 |
| WO | 2004-070052 | A2 | 8/2004 |
| WO | 2004-092339 | A2 | 10/2004 |
| WO | 2005-084158 | A2 | 9/2005 |
| WO | 2005-097116 | A1 | 10/2005 |
| WO | 2007-031098 | A1 | 3/2007 |
| WO | 2008-028860 | A1 | 3/2008 |
| WO | 2009-143864 | A1 | 12/2009 |
| WO | 2009-143865 | A1 | 12/2009 |

OTHER PUBLICATIONS

S. Rudikoff, et al. Proc. Natl. Acad. Sci. USA (1982) 79, pp. 1979-1983.
D. Wilson. Preventing Nerve Cell Death in ALS. Internet document http://www.als.ca/_news/57.aspx 2 pages, Dec. 5, 2001, accessed Aug. 23, 2006.
Parkinson's Disease; Challenges, NIH Publication 05-5595. Apr. 22, 2005, 22 pages.
H. Adle-Biassette, et al. Neuropathol. Appl. Neurobiol. (1999)25(2), pp. 123-133.
Adler et al., "Regulation of JNK signaling by GSTp", EMBO J. 18(5), pp. 1321-1334 (1999).
Brady et al., "Drug design. Reflections on a peptide", Nature 368, pp. 692-693 (1994).
Brugidou et al., "The Retro-inverso Form of a Homeobox-Derived Short Peptide is Rapidley Internalized by Cultured Neurons: A New Basis for an Efficient Intracellular Delivery System", Biochem. Biophys. Res. Comm. 214(2), pp. 685-693 (1995).
Chie et al., "Identification of the site of inhibition of oncogenic ras-p21-induced signal transduction by a peptide from a ras effector domain", J Protein Chem. 18(8), pp. 881-884 (1999).
Chorev et al., "A dozen years of retro-inverso peptidomimetics", Acc. Chem. Res. 26, pp. 266-273 (1993).
Chorev et al., "Recent developments in retro peptides and proteins—an ongoing topochemical exploration", Trends Biotechnol. 13(10), pp. 438-445 (1995).
Dang et al., "Nuclear and nucleolar targeting sequences of c-erb-A, c-myb, N-myc, p53, HSP70, and HIV tat proteins", J. Biol. Chem. 264(30), pp. 18019-18023 (1989).
Elliott et al., "Intercellular trafficking and protein delivery by a herpesvirus structural protein", Cell, 88(2), pp. 223-233 (1997).
Frankel et al., "Activity of synthetic peptides from the Tat protein of human immunodeficiency virus type 1", Proc. Natl. Acad. Sci. USA, 86, pp. 7397-7401 (1989).
GenBank Accession No. AF218778.
Giorello et al., "Inhibition of cancer cell growth and c-Myc transcriptional activity by a c-Myc helix 1-type peptide fused to an internalization sequence", Cancer Res. 58, pp. 3654-3659 (1998).
Guichard et al., "Partially modified retro-inverso pseudopeptides as non-natural ligands for the human class I histocompatibility molecule HLA-A2", J. Med. Chem. 39, pp. 2030-2039 (1996).
Hauber et al., "Mutational analysis of the conserved basic domain of human immunodeficiency virus tat protein", J. Virol. 63(3), pp. 1181-1187 (1989).
Jackson et al., "Heat shock induces the release of fibroblast growth factor 1 from NIH 3T3 cells", Proc. Natl. Aca. Sci. USA, 89, pp. 10691-10695 (1996).
Jameson et al., "A rationally designed CD4 analogue inhibits experimental allergic encephalomyelitis", Nature, 368(6473), pp. 744-746 (1994).
Lebleu, "Delivering information-rich drugs—prospects and challenges", Trends Biotechnol., 14(4), pp. 109-110 (1996).
Lin et al., "Inhibition of nuclear translocation of transcription factor NF-kappa B by a synthetic peptide containing a cell membrane-permeable motif and nuclear localization sequence", J. Biol. Chem. 270, pp. 14255-14258 (1996).
Nagahara et al., "Tranduction of full-length TAT fusion proteins into mammalian cells: TAT-p27Kip1 induces cell migration", Nat Med. 4(12), pp. 1449-1452 (1998).
Noguchi et al., "Regulation of c-Myc through phophorylation at Ser-62 and Ser-71 by c-Jun N-terminal kinase", J. Biol. Chem. 274(46), pp. 32580-32587 (1999).
Rojas et al., "Controlling epidermal growth factor (EGF)-stimulated Ras activation in intact cells by a cell-permeable peptide mimicking phosphorylated EGF receptor", J. Biol. Chem. 271, pp. 27456-27461 (1996).
Ruben et al., "Structural and functional characterization of human immunodeficiency virus tat protein", J. Virol. 63(1), pp. 1-8 (1989).
Schwarze et al., "In vivo protein transduction: delivery of a biologically active protein into the mouse", Science, 285(5433), pp. 1569-1572 (1999).
Torgerson et al., "Regulation of NF-kappa B, AP-1, NFAT, and STAT1 nuclear import in T lymphocytes by noninvasive delivery of peptide carrying the nuclear localization sequence of NF-kappa B p50", J. Immunol. 161(11), pp. 6084-6092 (1998).
Van Regenmortel et al., "D-peptides as immunogens and diagnostic reagents", Curr. Opin. Biotechnol. 9(4), pp. 377-382 (1998).
Vocero-Akbani et al., "Killing HIV-infected cells by transduction with an HIV protese-activated caspase-3 protein", Nat. Med. 5(1), pp. 29-33 (1999).
Yang et al., "Differential targeting of MAP kinases to the ETS-domain transcription factor Elk-1", EMBO J. 7, pp. 1740-1749 (1998).
Zhang et al., "Preparation of functionally active cell-permeable peptides by single-step ligation of two pepetide modules", Proc. Natl. Acad. Sci. USA, 95(16), pp. 9184-9189 (1998).
Briand et al., A retro-inverso peptide corresponding to the GH loop of foot-and-mouth disease virus elicits high levels of long-lasting protective neutralizing antibodies, Proc. Natl. Acad. Sci. USA 94:12545-12550 (1997).
Marino et al., Inhibition of experimental autoimmune encephalomyelitis in SJL mice by oral administration of retro-inverso derivative of encephalitogenic epitope P87-99, Eur. J. Immunol. 29:2560-2566 (1999).
Yasuda et al., The JIP group of mitogen-activated protein kinase scaffold proteins, Mol. Cell. Biol. 19(10);7245-7254 (1999).
Torchilin, Vladimir P. —Fluorescense Microscopy to Follow the Targeting of Liposomes and Micelles to Cells and their Intracellular Fate—Advanced Drug Delivery Reviews—2005—pp. 95-109—vol. 57—ScienceDirect—Elsevier B.V.—The Netherlands.
Touchard et al.—A Peptide Inhibitor of c-Jun N-Terminal Kinase for the Treatment of Endotoxin-Induced Uveitis—Immunology and Microbiology—Investigative Ophthalmology & Visual Sciene—Sep. 2010—pp. 4683-4693—vol. 51—No. 9—Association for Research in Vision and ophthalmology—USA.
Tournier et al.—Mitogen-Activated Protein Kinasa 7 is an Activator of the c-Jun NH2-Terminal Kinase—Cell Biology—Proceedings of the National Academy of Science—Jul. 1997—pp. 7337-7342—vol. 94—National Academy of Science—USA.

Vives et al.—A Truncated HIV-1 Tat Protein Basic Domain Rapidly Translocates Through the Plasma Membrane and Accumulates in the Cell Nucleus—Journal of Biological Chemistry—Jun. 20, 1997—pp. 16010-16017—vol. 272—No. 25—The American Society for Biochemistry and Molecular Biology, Inc.—USA.

Vives et al.—Struture-Activity Relationship Study of the Plasma Membrane Translocating Potential of a Short Peptide from HIV-1 Tat Protein—Letters in Peptide Science—1997—pp. 429-436—vol. 4—Kluwer Acdemic Publishers—The Netherlands.

Voet, Donald and Voet, Judith G.—Abnormal Hemoglobins—1995—pp. 235-241—Biochemistry Second Edition—John Wiley & Sons, Inc.—USA.

Wadia et al.—Delivery of Novel Anti-Cancer Peptides by Protein Transduction Domains—Peptides—2004—pp. 65-69—American Pharmaceutical Review—USA.

Waldmeier et al.—Recent Clinical Failures in Parkinson's Disease with Apoptosis Inhibitors Underline the Need for a Paradigm Shift in Drug Discovery for Neurodegenerative Diseases—Biochemistry Pharmachology—Nov. 15, 2006—pp. 1197-1208—vol. 72—No. 10—ScienceDirect—Elsevier Inc.—USA.

Walsh et al.—Erythrocyte Survival is Promoted by Plasma and Suppressed by a Bak-Derived BH3 Peptide that Interacts with Membrane-Associated Bcl-XL—Red Cells—Blood—May 1, 2002—pp. 3439-3448—vol. 99—No. 9—The American Society of Hematology—USA.

Wender et al.—The Design, Sytsesis and Evaluation of Molecules that Enable or Enhance Cellular Uptake: Peptoid Molecular Transporters—PNAS—Proceedings of the National Academy of Sciences—Nov. 21, 2000—pp. 13003-13008—vol. 97—No. 24—National Academy of Sciences—USA.

Whitmarsh et al.—A Mammalian Scaffold Complex That Selectively Mediates MAP Kinase Activation—Science—Sep. 11, 1998—pp. 1671-1674—vol. 281—www.sciencemag.org—USA.

Whitmarsh, A.J. and Davis, R.J.—Transcription Factor AP-1 Regulation by Mitogen-Activated Protein Kinasa Signal Transduction Pathways—Review—Journal of Molecular Medicine—Oct. 7, 1996—pp. 589-607—vol. 74—No. 10—Springer-Verlag—USA.

Wishart et al.—A Single Mutation Converts a Novel Phosphotyrosine Binding Domain into a Dual-specificity Phosphatase—Communication—The Journal of Biological Chemistry—Nov. 10, 1995—pp. 26782-26785—vol. 270—No. 45—The American Society for Biochemistry and Molecular Biology, Inc.—USA.

Witkowski et al.—Conversion of a β-Ketoacyl Synthase to a Malonyl Decarboxylase by Replacement of the Active-Site Cysteine with Glutamine—Biochemistry—Aug. 18, 1999—pp. 11643-11650—vol. 38—American Chemical Society—USA.

Wyszko et al.—Interaction of Native RNAs with Tat Peptides—NATO Science Series, 3: High Technology 1999, 70 (RNA Biochemistry and Biotechnology), Sep. 9, 2002—pp. 277-290—Institute of Bioorganic Chemistry of the Polish Academy Sciences, Poznan—Poland—Kluwer Academiv Publishers—Chemical Abstracts Database Accession No. 133:204452 CA—No. XP002554007—Poland.

Yamamoto et al.—Molecular Design of Bioconjugated Cell Adhesian Peptide with a Water-Soluble Polymeric Modifer for Enhancement of Antimetastatic Effect—Current Drug Targets—2002—pp. 123-130—vol. 3—Bentham Science Publishers Ltd.—USA.

Zoukhri et al.—c-Jun NH2-Terminal Kinase Mediates Interleukin-1 β-Induced Inhibition of Lacrimal Gland Secretion—Journal of Neurochemistry—2006—pp. 126-135—vol. 96—International Society for Neurochemistry—USA.

NCBI Sequence Viewer—Accession No. AAD20443—Reports—Islet-Brain 1 (*Homo sapiens*)—Two References—Mooser et al.—Mar. 17, 1999—2 pages—USA.

NCBI Sequence Viewer—Accession No. AAD22543—Reports—Islet-Brain 1 (*Rattus norvegicus*)—Three References—Bonny et al.—Mar. 1, 2006—2 pages—USA.

NCBI Sequence Viewer—Accession No. AAF32323—Reports—Islet-Brain 2 (*Homo sapiens*)—Two References—Negri et al.—Feb. 9, 2000—2 pages—USA.

NCBI Sequence Viewer—Accession No. AF074091—Reports—*Homo sapiens* Islet-Brain 1 mRNA—Complete Cds.—Two References—Mooser et al.—Mar. 17, 1999—2 pages—USA.

NCBI Sequence Viewer—Accession No. AF108959—Reports—*Rattus norvegicus* Islet-Brain 1 (IB1) mRNA—Complete Cds.—Three References—Bonny et al.—Mar. 1, 2006—2 pages—USA.

NCBI Sequence Viewer—Accession No. AF218778—Reports—*Homo sapiens* Islet-Brain 2 mRNA—Complete Cds—Three References—Kristensen et al.—Mar. 2, 2006—2 pages—USA.

NCBI Sequence Viewer—Accession No. PH0878—Reports—Ig Kappa Chain V Region (Anti-DNA, SNA)—Human (Fragment) One Reference—Manheimer-Lory et al.—May 30, 1997—1 page—USA.

Ahmed, Shafiq Uddin and Milner, Jo—Basal Cancer Cell Survival Involves JNK2 Suppression of a Novel JNK1/c-Jun/Bcl-3 Apoptotic Network—PLoS ONE—Oct. 2009—pp. 1-13—vol. 4—Issue 10—University of York—United Kingdom.

Duby et al. (Contributors)—Using Synthetic Oligonucleotides as Probes—Current Protocols in Molecular Biology—Supplement 2—Apr. 1988—pp. 6.4.1-6.4.10—John Wiley & Sons—Document No. XP-002044485—USA.

Fischer, P.M.—The Design, Synthesis and Application of Stereochemical and Directional Peptide Isomers: A Critical Review—Current Protein and Peptide Science—2003—pp. 339-356—vol. 4—Bentham Science Publishes Ltd.—United Kingdom.

Thoren et al.—The Antennapedia Peptide Penetratin Translocates across Lipid Bilayers—The First Direct Observation—FEBS Letters—2000—pp. 265-268—No. 482—Federation of European Biochemical Societies—Elsevier Science B.V.—Europe.

Aarts et al.—Treatment of Ischemic Brain Damage by Perturbing NMDA Receptor—PSD-95 Protein Interactions—Science—Oct. 25, 2002—pp. 846-850—vol. 298—www.sciencemag.org—USA.

Abaza et al.—Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin—Journal of Protein Chemistry—1992—pp. 433-444—vol. 11—No. 5—USA.

Agrawal, Vishal and Kishan, K.V. Radha—Promiscuous Binding Nature of SH3 Domains to their Target Proteins—Protein and Peptide Letters—2002—pp. 185-193—vol. 9—No. 3—Bentham Science Publishers Ltd.—USA.

Aldrian-Herrada et al.—A Peptide Nucleic Acid (PNA) is More Rapidly Internalized in Cultured Neurons when Coupled to a Retro-Inverso Delivery Peptide. The Antisense Activity Depresses the Target mRNA and Protein in Magnocellular Oxytocin Neurons—Nucleic Acids Research—1998—pp. 4910-4916—vol. 26—No. 21—Oxford University Press—United Kingdom.

Assi et al.—The Specific JNK Inhibitor SP600125 Targets Tumour Necrosis Factor-βProduction and Epithelial Cell Apoptosis in Acute Murine Colitis—Immunology—2006—pp. 112-121—Blackwell Publishing Ltd.—USA.

Barr et al.—Identification of the Critical Features of a Small Peptide Inhibitor of JNK Activity—Mar. 20, 2002—pp. 10987-10997—vol. 277—No. 13—USA.

Berendsen, Herman J.C.—A Glimpse of the Holy Grail?—Oct. 23, 1998—pp. 642-643—vol. 282—No. 5389—Science—Research Library—USA.

Bessalle et al.—All-D-Magainin: Chirality, Antimicrobial Activity and Proteolytic Resistance—FEBS Letters—Nov. 12, 1990—pp. 151-155—vol. 274—No. 1/2—Federation of European Biochemical Societies—Elsevier Science Publishes B.V.—The Netherlands.

Bonny et al.,—Cell-Permeable Peptide Inhibitors of JNK: Novel Blockers of Beta-Cell Death—Diabetes—Jan. 2001—pp. 77-82—vol. 50—No. 1—USA.

Bonny et al.—IB1, A JIP-1-Related Nuclear Protein Present in Insulin-Secreting Cells—Journal of Biological Chemistry—Jan. 23, 1998—pp. 1843-1846—vol. 273—No. 4—USA.

Bonny et al.—Pancreatic-Specific Expression of the Glucose Transporter Type 2 Gene: Identification of cis-Elements and Islet-Specific trans-Acting Factors—Mol Endo—Molecular Endrocrinology—1995—pp. 1413-1426—vol. 9—No. 10—The Endocrine Society—USA.

Bonny et al.—Targeting the JNK Pathway as a Therapeutic Protective Strategy for Nervous Systems Diseases—2005—pp. 57-67—vol. 16—No. 1—Freund & Pettman—United Kingdom.

Borsello et al.—A Peptide Inhibitor of c-Jun N-Terminal Kinase Protects Against Excitotoxicity and Cerebral Ischemia—Aug. 24, 2003 (Sep. 2003)—pp. 1180-1186—vol. 9—No. 9—Nature Medicine—USA.

Borsello, Tiziana and Bonny, Christophe—Use of Cell-Permeable Peptides to Prevent Neuronal Degeneration—TRENDS in Molecular Medicine—May 2004—pp. 239-244—vol. 10—No. 5—Elsevier Ltd—www.sciencedirect.com—USA.

Bradley, Christina Marchette and Barrick, Doug—Limits of Cooperativity in a Structurally Modular Protein: Response of the Notch Ankyrin Dpmaon to Analogous Alanine Substitutions in Each Repeat—JMB—Journal of Molecular Biology—Nov. 22, 2002—pp. 373-386—vol. 324—USA.

Branden et al.—A Peptide Nucleic Acid-Nuclear Localization Signal Fusion that Mediates Nuclear Transport of DNA—Nature Biotechnology—Aug. 1999—pp. 784-787—vol. 17—Nature America Inc.—USA.

Branden, Carl and Tooze, Carl—Introduction to Protein—Second Edition—1999—Garland Publishing, Inc.—p. 382—USA.

Branden, Carl and Tooze, Carl—Introduction to Protein—1991—Garland Publishing, Inc.—p. 247—USA.

Cardozo et al.—Cell-Permeable Peptides Induce Dose- and Length-Dependent Cytotoxic Effects—Biochimica et Biophysica Acta—Jun. 14, 2007—pp. 2222-2234—No. 1768—ScienceDirect—Elsevier B.V.—The Netherlands.

Chaloin et al.—Design of Carrier Peptide-Oligonucleotide Conjugates with Rapid Membrane Translocation and Nuclear Localization Properties—Biochemical and Biophysical Research Communications—Article No. RC978050—1998—pp. 601-608—vol. 243—No. 2—Academic Press—Elsevier B.V.—The Nethlands.

Creighton, Thomas E. (Editor)—Janin, Jaël—Protein—Protein Interactions—Encyclopedia of Molecular Biology—1999—pp. 2027-2033—vol. 1—A Wiley-Interscience Publication—John Wiley & Sons, Inc.—USA.

Derossi et al.—Cell Internalization of the Third Helix of the Antennapedia Homeodomain is Receptor-independent—The Journal of Biological Chemistry—Jul. 26, 1996—pp. 18188-18193—vol. 271—No. 30—The American Society for Biochemistry and Molecular Biology, Inc.—USA.

Designing Custom Peptides—Sigma Genosys—Technical Bulletin—Dec. 16, 2004—2 pages—<http://www.sigma-genosys.com/peptide_design.asp>—USA.

Dickens et al.—Database—UNIPROT—Retrieved from EBI—Database Accession No. Q9WVI9—Abstracts—Feb. 28, 2003—Document No. XP-002366175—USA.

Dickens et al.—A Cytoplasmic Inhibitor of the JNK Signal Transduction Pathway—Science—Aug. 1, 1997—pp. 693-696—vol. 277—No. 5326—Science Magazine—USA.

Dietz, Gunner P.H. and Bahr, Mathias—Review—Delivery of Bioactive Molecules into the Cell: The Trojan Horse Approach—Molecular and Cellular Neuroscience—2004—pp. 85-131—vol. 27—Elsevier Inc.—The Netherlands.

Dominguez-Bendala et al.—TAT-Mediated Neurogenin 3 Protein Transduction Stimulates Pancreatic Endocrine Differentiation In Vitro—Diabetes—Mar. 2005—pp. 720-726—vol. 54—The American Diabetes Association—USA.

Fawell et al.—TAT-Mediated Delivery of Heterologous Proteins into Cells—Cell Biology—Proceedings of the National Academy of Sciences—Jan. 8, 1994—pp. 664-668—vol. 91—Biogen Inc.—USA.

Fornoni et al.—The L-Isoform but not D-Isoforms of a JNK Inhibitory Peptide Protects Pancreatic β-cells—Biochemical and Biophysical Research Communications—Jan. 2, 2007—pp. 227-233—vol. 354—ScienceDirect—Elsevier Inc.—USA.

Frankel, Alan D. and Pabo, Carl O.—Cellular Uptake of the Tat Protein from Human Immunodeficiency Virus—Cell—Dec. 23, 1988—pp. 1189-1193—vol. 55—Cell Press—USA.

Fujita et al.—Prophylactic or Therapeutic Agent for Retinal Diseases and Method for Preventing or Treating Retinal Diseases, Each Comprising JNK (C-JUN N-Terminal Kinase)-Inhibiting Peptide, and Use of the Peptide—International Application No. PCT/JP2010/55208—Santen Pharmaceutical Co., Ltd.—Database WPI—Thompson Scientific—pp. 1-4—Document No. XP-002643212—USA.

Futaki et al.—Arginine-rich Peptides—An Abundant Source of Membrane-Permeable Peptides Having Potential as Carriers for Intracellular Protein Delivery—The Journal of Biological Chemistry—Feb. 23, 2001—pp. 5836-5840—vol. 276—No. 8—The American Society of Biochemistry and Molecular Biology, Inc.—USA.

Gammon et al.—Quantitative Analysis of Permeation Peptide Complexes Labeled with Technetium-99m: Chiral and Sequence-Specific Effects on Net Cell Uptake—Bioconjugate Chemistry—Mar. 4, 2003—pp. 368-376—vol. 14—No. 2—American Chemical Society—USA.

Gotthardt et al.—Interactions of the Low Density Lipoprotein Receptor Gene Family with Cytosolic Adaptor and Scaffold Proteins Suggest Diverse Biological Functions in Cellular Communication and Signal Transduction—The Journal of Biological Chemistry—Aug. 18, 2000—pp. 25616-25624—vol. 275—No. 33—The American Society for Biochemistry and Molecular Biology, Inc.—USA.

Guichard et al.—Antigenic Mimicry of Natural L-Peptides with Retro-Inverso-Peptidomimetics—Proceedings of the National Academy of Sciences—Immunology—Oct. 1994—pp. 9765-9769—vol. 91—The National Academy of Sciences—USA.

Gunaseelan et al.—Synthesis of Poly(ethylene glycol)-Based Saquinavir Prodrug Conjugates and Assessment of Release and Anti-HIV-1 Bioactivity Using a Novel Protease Inhibition Assay—Bioconjugate Chemistry—Oct. 28, 2004—pp. 1322-1333—vol. 15—No. 6—American Chemical Society—USA.

Gura, Trisha—Cancer Models: Systems for Identifying New Drugs Are Often Faulty—Science—Nov. 7, 1997—pp. 1041-1042—No. 278 (5340)—USA.

Hawiger, Jacek—Noninvasive Intracellular Delivery of Functional Peptides and Proteins—Current Opinion in Chemical Biology—1999—pp. 89-94—vol. 3—Elsevier Science Ltd—USA.

Hayashi et al.—Development of Oligoarginine-Drug Conjugates Linked to New Peptidic Self-Cleavable Spacers Toward Effective Intestinal Absorption—Bioorganic and Medicinal Chemistry Letters—Jul. 7, 2007—pp. 5129-5132—vol. 17—ScienceDirect—Elsevier Ltd—USA.

Heemskerk et al.—From Chemical to Drug: Neurodegeneration Drug Screening and the Ethics of Clinical Trials—Commentary—Nature Neuroscience Supplement—Nov. 2002—pp. 1027-1029—vol. 5—Nature Publishing Group—http://www.nature.com/natureneuroscience—USA.

Herve et al.—On the Immunogenic Properties of Retro-Inverso Peptides. Total Retro-Inversion of T-Cell Epitopes Causes a Loss of Binding to MHC II Molecules—Molecular Immunology—1997—pp. 157-163—vol. 34—No. 2—Elsevier Science Ltd.—UK.

Hillier et al.—*Homo sapiens*—The WashU-Merck EST Project—EMBL Sequence Database—R85141—Aug. 17, 1995—p. 1—Document No. XP-002076858—USA.

Ho et al.—Synthetic Protein Transduction Domains: Enhanced Transduction Potential in Vitro and in Vivo—Advances in Brief—Cancer Research—Jan. 15, 2001—pp. 474-477—vol. 61—USA.

Holinger et al.—Bak BH3 Peptides Antagonize Bcl-xL Function and Induce Apoptosis through Cytochrome c-Independent Activation of Caspases—The Journal of Biological Chemistry—May 7, 1999—pp. 13298-13304—vol. 274—No. 19—The American Society for Biochemistry and Molecular Biology, Inc.—USA.

Holzberg et al.—Disruption of the c-JUN-JNK Complex by a Cell-permeable Peptide Containing the c-JUN δ Domain Induces Apoptosis and Affects a Distinct Set of Interleukin-1-induced Inflammatory Genes—The Journal of Biological Chemistry—Oct. 10, 2003—pp. 40213-40223—vol. 278—No. 41—The American Society for Biochemistry and Molecular Biology, Inc.—USA.

Houghten, Richard A.—General Method for the Rapid Solid-Phase Synthesis of Large Numbers of Peptides: Specificity of Antigen-Antibody Interaction at the Level of Individual Amino Acids—Proceedings of the National Academy of Sciences—Immunology—Aug. 1985—pp. 5131-5135—vol. 82—The National Academy of Sciences—USA.

Huq et al.—Specific Recognition of HIV-1 TAR RNA by a D-Tat Peptide—Comment—Nature Structural Biology—Nov. 1997—pp. 881-882—vol. 4—No. 11—Nature Publishing Group—http://www.nature.com/nsmb—USA.

Johnson, Gary L. and Nakamura, Kazuhiro—The c-jun Kinase/Stress-Activated Pathway: Regulation, Function and Role in Human Disease—Biochimica et Biophysica Acta—Jan. 4, 2007—pp. 1341-1348—vol. 1773—ScienceDirect—Elsevier B.V.—The Netherlands.

Jung, Günther (Editor)—Chapter 5—The Versatility of Nonsupport-Bound Combinatorial Libraries—Pinilla et al.—Combinatorial Peptide and Nonpeptide Libraries—A Handbook—May 1997—pp. 139-171—Wiley-VCH—USA.

Jung, Günther (Editor)—Chapter 11—Cyclic Peptide Libraries: Recent Developments—Spatola, Arno F. and Romanovskis, Peteris—Combinatorial Peptide and Nonpeptide Libraries—A Handbook—May 1997—pp. 327-347—Wiley-VCH—USA.

Kennedy, Norman J. and Davis, Roger J.—Perspectives: Role of JNK in Tumor Development—Cell Cycle—May/Jun. 2003—pp. 199-201—vol. 2—No. 3—www.landesbioscience.com—USA.

Kida et al.—Design and Synthesis of a Tat-related Gene Transporter: A Tool for Carrying the Adenovirus Vector into Cells—Bioorganic and Medicinal Chemistry Letters—Dec. 6, 2005—pp. 743-745—vol. 16—ScienceDirect—Elsevier Ltd—USA.

Kieber-Emmons et al.—Therapeutic Peptides and Peptidomimetics—Current Opinion in Biotechnology—1997—pp. 435-441—vol. 8—Current Biology Ltd.—USA.

Kishan, K.V. Radha and Agrawal, Vishal—SH3-like Fold Proteins are Structurally Conserved and Functionally Divergent—Current Protein and Peptide Science—1995—pp. 143-150—vol. 6—Nentham Science Publishers Ltd.—USA.

Kisselev, Lev—Polypeptide Release Factors in Prokaryotes and Eukaryotes: Same Function, Different Structure—Jan. 2002—pp. 8-9—vol. 10—Structure—Elsevier Science Ltd—USA.

Lee et al.—c-Jun N-terminal Kinasa (JNK) Mediates Feedback Inhibition of the Insulin Signaling Cascade—The Journal of Biological Chemistry—Jan. 31, 2003—pp. 2896-2902—vol. 278—No. 5—The American Society for Biochemistry and Molecular Biology, Inc.—USA.

Lewis et al.—Lymphoma Cell Uptake of Radiometal- and Fluorescent-Labelled BCL-2 Antisense PNA Conjugates is Mediated by a Retro-Inverso Delivery Peptide—Abstracts—Journal of Label Compounds and Radiopharmaceuticals—2003—p. S13—vol. 46—SI-S403—XP-002347557—USA.

Li, Shawn S.C.—Review Article—Specificity and Versatility of SH3 and Other Ptoline-Recognition Domains: Structural Basis and Implications for Cellular Signal Transduction—Biochemical Journal—Sep. 15, 2005—pp. 641-653—Biochemical Society—vol. 390—Part 3—United Kingdom.

Lim et al.—Penetration Enhancement in Mouse Skin and Lipolysis in Adipocytes by TAT-GKH, A New Cosmetic Ingredient—Journal of Cosmetic Science—Sep./Oct. 2003—pp. 483-491—vol. 54—USA.

Lloyd-Williams et al.—Chapter 5—Chemical Approaches to the Synthesis of Peptides and Proteins—1997—Formation of Disulfide Bridges—pp. 209-236—CCR Press LLC—USA.

Lloyd-Williams et al.—Chapter 6—Chemical Approaches to the Synthesis of Peptides and Proteins—1997—Peptide Libraries—pp. 237 and 264-267—CRC Press LLC—USA.

Mann, David A. and Frankel, Alan D.—Endocytosis and Targeting of Exogenous HIV-1 Tat Protein—The EMBO Journal—1991—pp. 1733-1739—vol. 10—No. 7—Oxford University Press—United Kingdom.

Marks et al.—Protein Targeting by Tyrosine- and Di-leucine-based Signals: Evidence for Distinct Saturable Components—The Journal of Cell Biology—Oct. 1, 1996—pp. 341-354—vol. 135—No. 2—The Rockefeller University Press—USA.

Mayer, Bruce J.—SH3 Domains: Complexity in Moderation—Commentary—Journal of Cell Science—Signal Transduction and Cellular Organization—Apr. 2001—pp. 1253-1263—vol. 114—The Company of Biologists Ltd—USA.

Mazur, Dan J. and Perrino, Fred W.—Identification and Expression of the TREX1 and TREX2 cDNA Sequences Encoding Mammalian 3'→5' Exonucleases—The Journal of Biological Chemistry—Jul. 9, 1999—pp. 19655-19660—vol. 274—No. 28—The American Society for Biochemistry and Molecular Biology, Inc.—USA.

Melikov, K. and Chernomordik, L.V.—Review—Arginine-rich Cell Penetrating Peptides: From Endosomal Uptake to Nuclear Delivery—Cellular and Molecular Life Sciences—Oct. 18, 2005—pp. 2739-2749—vol. 62—Birkhauser Verlag—Switzerland.

Mi et al.—Characterization of a Class of Cationic Peptides Able to Facilitate Efficient Protein Transduction in Vitro and in Vivo—Article—Molecular Therapy—Oct. 2000—pp. 339-347—vol. 2—No. 4—The American Society of Gene Therapy—USA.

Milano et al.—A Peptide Inhibitor of c-Jun NH2-terminal Kinase Reduces Myocardial Ischemia-reperfusion Injury and Infarct Size in Vivo—American Journal of Physiology—Heart Circulation Physiology—Apr. 2007—pp. H1828-H1835—vol. 292—www.ajpheart.org—The American Physiological Society—USA.

Mooi et al.—Regulation and Structure of an *Escherichia coli* Gene Coding for an Outer Membrane Protein Involved in Export of K88ab Fimbrial Subunits—Nucleic Acids Research—1986—pp. 2443-2457—vol. 14—No. 6—IRL Press Limited—United Kingdom.

Moon et al—Bcl-2 Overexpression Attenuates SP600125-induced Apoptosis in Human Leukemia U937 Cells—Cancer Letters—Feb. 3, 2008—pp. 316-325—vol. 264—ScienceDirect—Elsevier Ireland Ltd—Ireland.

Mooser et al.—Genomic Organization, Fine-Mapping, and Expression of the Human Islet-Brain 1 (IB1)/C-Jun-Amino-Terminal Kinase Interacting Protein-1 (JIP-1) Gene—Genomics—Jan. 15, 1999—pp. 202-208—vol. 55—Academic Press—USA.

Moulin, Nathalie and Widman, Christian—Islet-Brain (IB)/JNK-Interacting Proteins (JIPs): Future Targets for the Treatment of Neurodegenerative Diseases?—Current Neurovascular Research—2004—pp. 111-127—vol. 1—No. 2—Institut de Biologie Cellulaire et de Morphologie (IBCM)—Université de Lusanne—Switzerland—Bentham Science Publishers Ltd.—USA.

Negri et al.—Design of a Novel Peptide Inhibitor of the JNK Signaling Pathway—1217-P—Journal—Diabetes—Abstract Book—61st Scientific Session—Jun. 2001—p. A294—vol. 50—Supplement No. 2—American Diabetes Association—USA.

Neundorf et al.—Detailed Analysis Concerning the Biodistribution and Metabolism of Human Calcitonin-Derived Cell-Penetrating Peptides—Bioconjugate Chemistry—Jul. 24, 2008—pp. 1596-1603—vol. 19—No. 8—American Chemical Society—USA.

Ngo et al.—Computational Complexity, Protein Structure Prediction, and the Levinthal Paradox—The Protein Folding Problem and Tertiary Structure Prediction—Merz et al. (Editors)—1994—pp. 433, 492-495—Birkhauser Boston—USA.

Nori, Aparna and Kopecek, Jindrich—Intracellular Targeting of Polymer-Bound Drugs for Cancer Chemotherapy—Advanced Drug Delivery Reviews—Dec. 24, 2004—pp. 609-636—vol. 57—ScienceDirect—Elsevier B.V.—The Netherlands.

Nori et al.—Tat-Conjugated Synthetic Macromolecules Facilitate Cytoplasmic Drug Delivery to Human Ovarian Carcinoma Cells—Bioconjugate Chemistry—Nov. 16, 2002—pp. 44-50—vol. 14—No. 1—American Chemical Society—USA.

Okitsu et al.—Protein Transduction Domains Enable Isolated Islets to Efficiently Internalize the Target Protein—Transplantation Proceedings—2003—p. 479—vol. 35—Elsevier Science Inc.—USA.

Pan et al.—Small Peptide Inhibitor of JNKs Protects Against MPTP-Induced Nigral Dopaminergic Injury via Inhibiting the JNK-Signaling Pathway—Laboratory Investigation—Feb. 2010—pp. 156-167—vol. 90—USCAP, Inc.—USA.

Penco et al.—Identification of an Import Signal for, and the Nuclear Localization of, Human Lactoferrin—Biotechnology and Applied Biochemistry—2001—pp. 151-159—vol. 34—Portland Press Ltd—United Kingdom.

Pennington, Michael W. and Dunn, Ben M. (Editors)—Chapter 11—Design of Novel Synthetic Peptides Including Cyclic Conformationally and Topgraphically Constrained Analogs—Hruby, Victor J. and Bonner, G. Gregg—Methods in Molecular Biology—vol. 35—Peptide Synthesis Protocols—1994—pp. 201-239—Humana Press Inc.—USA.

Pennington, Michael W. and Dunn, Ben M. (Editors)—Chapter 12—Solid-Phase Synthesis of Peptides Containing the CH2NH Reduced Bond Surrogate—Pennington, Michael W.—Methods in Molecular Biology—vol. 35—Peptide Synthesis Protocols—1994—pp. 241-247—Humana Press Inc.—USA.

Pirvola et al.—Rescue of Hearing, Auditory Hair Cells, and Neurons by CEP-1347/KT7515, an Inhibitor of c-Jun N-Terminal Kinase Activation—The Journal of Neuroscience—01-01-200—pp. 43-50—vol. 20—No. 1—Society of Neuroscience—USA.

Prantner et al.—Synthesis and Characterization of a Gd-DOTA-D-Permeation Peptide for Magnetic Resonance Relaxation Enhancement of Intracellular Targets—Research Article—Massachusetts Institute of Technology—Molecular Imaging—Oct. 2003—pp. 333-341—vol. 2—No. 4—The Society for Molecular Imaging—USA.

Ramage, Robert and Epton, Roger (Editors)—Chapters 165 and 166—Guichard et al.—Chapter 167—Gur'Yanov et al.—EPS—Peptides 1996—Proceedings of the Twenty-Fourth European Peptide Symposium—1998—pp. 447-451—The European Peptide Society—Mayflower Scientific Ltd—United Kingdom.

Ramage, Robert and Epton, Roger (Editors)—Chapter 183—Horvath et al.—Chapter 184—Hruby et al.—EPS—Peptides 1996—Proceedings of the Twenty-Fourth European Peptide Symposium—1998—pp. 483-486—The European Peptide Society—Mayflower Scientific Ltd—United Kingdom.

Ramanathan et al.—Targeting the Sodium-Dependent Multivitamin Transporter (SMVT) for Improving the Oral Absorption Properties of a Retro-Inverso Tat Nonapeptide—Pharmaceutical Research—Jul. 2001—pp. 950-956—vol. 18—No. 7—USA.

Ribeiro et al.—Heme Oxygenase-1 Fused to a TAT Peptide Transduces and Protects Pancreatic β-Cells—BBRC—Biochemical and Biophysical Research Communications—Apr. 4, 2003—pp. 876-881—vol. 305—ScienceDirect—Academic Press—Elsevier Science (USA)—USA.

Rickels et al.—Phage Display Selection of Ligand Residues Important for Src Homology 3 Domain Binding Specificity—Biochemistry—Proceedings of the National Academy of Science—Nov. 1995—pp. 10909-10913—vol. 92—National Academy of Science—USA.

Robinson et al.—Properties and Structure-Activity Studies of Cyclic β-Hairpin Peptidomimetics Based on the Cationic Antimicrobial Peptide Protegrin I—Bioorganic & Medicinal Chemistry—Jan. 7, 2005—pp. 2055-2064—vol. 13—ScienceDirect—Elsevier Ltd.—USA.

Roduit, Raphaël and Schorderet, Daniel F.—MAP Kinase Pathways in UV-Induced Apoptosis of Retinal Pigment—Epithelium ARPE19 Cells—Apoptosis—2008—pp. 343-353—DOI 10.1007/s10495-008-0179-8—Springer Science+Business Media, LLC—USA.

Roy et al.—Role of the JNK Signal Transduction Pathway in Inflammatory Bowel Disease—World Journal of Gastroenterology—Jan. 14, 2008—pp. 200-202—vol. 14—No. 2—www.wjgnet.com—USA.

Saito, Naoyuki G. and Paterson, Yvonne—Contribution of Peptide Backbone Atoms to Binding of an Antigenic Peptide to Class 1 Major Histocompatibility Complex Module—Molecular Immunology—Nov. 13, 1997—pp. 1133-1145—vol. 34—Nos. 16-17—Pergamon—Elsevier Science Ltd.—United Kingdom.

Schimmer et al.—The BH3 Domain of BAD Fused to the Antennapedia Peptide Induces Apoptosis via its Alpha Helical Structure and Independent of Bcl-2—Cell Death and Differentiation—Feb. 18, 2001—pp. 725-733—Canada.

Schinzel, R. and Drueckes, P.—The Phosphate Recognition Site of *Escherichia coli* Maltodextrin Phosphorylase—FEBS Letters—Jul. 29, 1991—pp. 125-128—vol. 286—Nos. 1 and 2—Federation of European Biochemical Societies—Elsevier Science Publishers B.V.—The Netherlands.

Sebestyen et al.—DNA Vector Chemistry: The Covalent Attachment of Signal Peptides to Plasmid DNA—Research—Nature Biotechnology—Jan. 1998—pp. 80-85—vol. 16—USA.

Selective Dimerisation of Cysteines to Form Heterodimers—Aim—Chemistry—Procedure—NJE—Feb. 3, 1997—USA.

Shimonishi, Yasutsuga (Editor)—Oehlke et al.—Rapid Translocation of Amphipathic α-Helical and β-Sheet-Forming Peptides through Plasma Membranes of Endothelian Cells—pp. 282-783—Van Regenmortel et al.—Peptide Analogues as Vaccines and Immunomodulators—pp. 784-787—Saito, N.G. and Paterson, Y.—Contributation of Peptide Backbone Atoms to Binding of an Antigenic Peptide to Class I Major Histocompatibility Complex Molecule—pp. 805-807—Peptide Science—Present and Future—Kluwer Academic Publishers—United.

Stevens et al.—Efficient Generation of Major Histocompatibility Complex Class 1-Peptide Complexes Using Synthetic Peptide Libraries—The Journal of Biological Chemistry—Jan. 30, 1998—pp. 2874-2884—vol. 273—No. 5—The American Society for Biochemistry and Molecular Biology, Inc.—USA.

Stevens et al.—Peptide Length Preferences for Rat and Mouse MHC Class 1 Molecules Using Random Peptide Libraries—European Journal of Immunology—Apr. 1998—pp. 1272-1279—vol. 28—Wiley-VCH Verlag GmbH—Germany.

\* cited by examiner

PEPTIDES SEQUENCES, HUMAN, MOUSE AND RAT

A.

```
                       ::        **.:
IB2       :  IPSPSVEEPHKHRPTTLRL--TTLGAQDS
IB1       :  PGTGCGDTYRPKRPTTLNLFPQVPRSQDT
C-JUN     :  GAYGYSNPKILKQSMTLNLADPVGNLKPH
ATF2      :  TNEDHLAVHKHKHEMTLKFGPARNDSVIV
```

B.

```
             :.******.*         **:
L-IB2     :  EEPHKHRPTTLRL--TTLGAQDS
L-IB1     :  DTYRPKRPTTLNLFPQVPRSQDT
                        o o
```

C.

```
L-TAT       :  NH2- GRKKRRQRRR                                   -COOH
L-TAT-IB1   :  NH2- GRKKRRQRRRPPDTYRPKRPTTLNLFPQVPRSQDT           -COOH
L-TAT-IB2   :  NH2- GRKKRRQRRRPEEPHKHRPTTLRLTTLGAQDS              -COOH
L-TAT-JBD20 :  NH2- GRKKRRQRRRPPRPKRPTTLNLFPQVPRSQDT              -COOH

D-TAT       :  NH2- RRRQRRKKRG                                    -COOH
D-TAT-IB1   :  NH2- TDQSRPVQPFLNLTTPRKPRYTDPPRRQRRKKRG            -COOH
D-TAT-JBD20 :  NH2- TDQSRPVQPFLNLTTPRKPRPPRRQRRKKRG               -COOH
```

FIG. 1

GENERIC SEQUENCES, HUMAN, MOUSE AND RAT

```
L-TAT-IB        : NH2- XXXXXXXRKKRRQRRRXXXXXXXXRPTTLXLXXXXXXXQDS/TX -COOH
L-TAT-JBD20     : NH2- XXXXXXXRKKRRQRRRXXXXXXXXRPTTLXLXXXXXXXQDS/TX -COOH
D-TAT           : NH2- XXXXXRRRQRRKKRXXXXX -COOH
D-TAT-IB        : NH2- XT/SDQXXXXXXLXLTTPRXXXXXXXXRRQRRKKRXXXXXXX -COOH
D-TAT-JBD20     : NH2- XT/SDQXXXXXXLXLTTPRXXXXXXXXRRQRRKKRXXXXXXX -COOH
```

FIG. 2

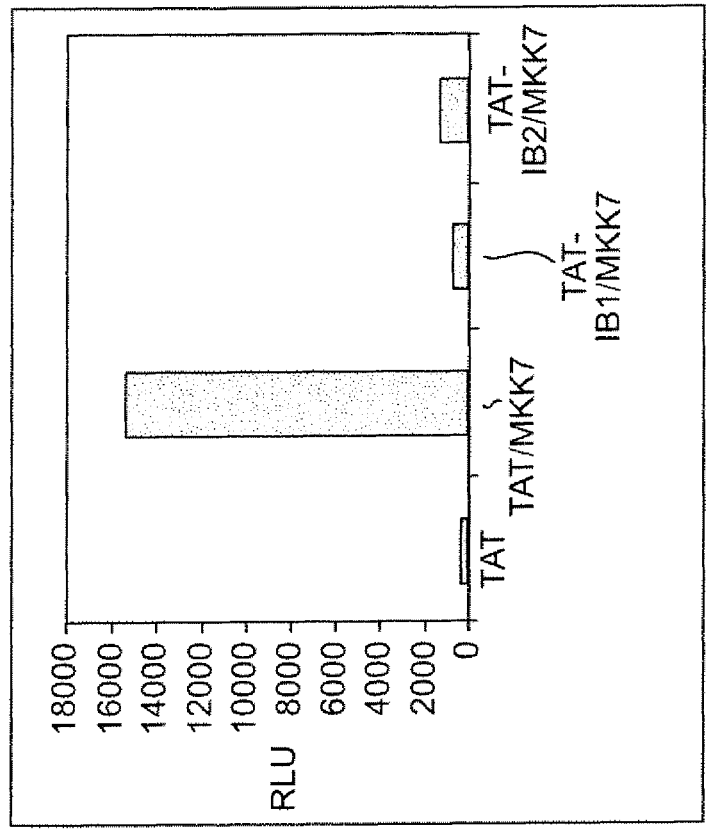
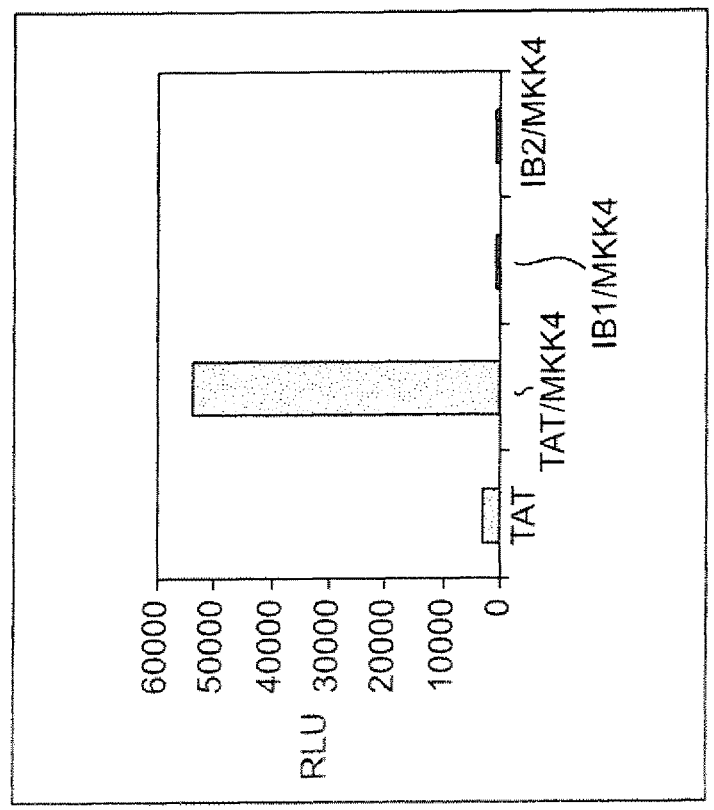
FIG. 5

L-TAT-IB1 AND D-TAT-IB1 PEPTIDES PREVENT IR-INDUCED
APOPTOSIS IN A HUMAN COLON CANCER CELL LINE

SUPPRESSION OF JNK TRANSCRIPTION FACTOR
PHOSPHORYLATION BY L-TAT-IB PEPTIDES

NEOMYCIN- EXPOSED CULTURES IN PRESENCE OF D-JNKI

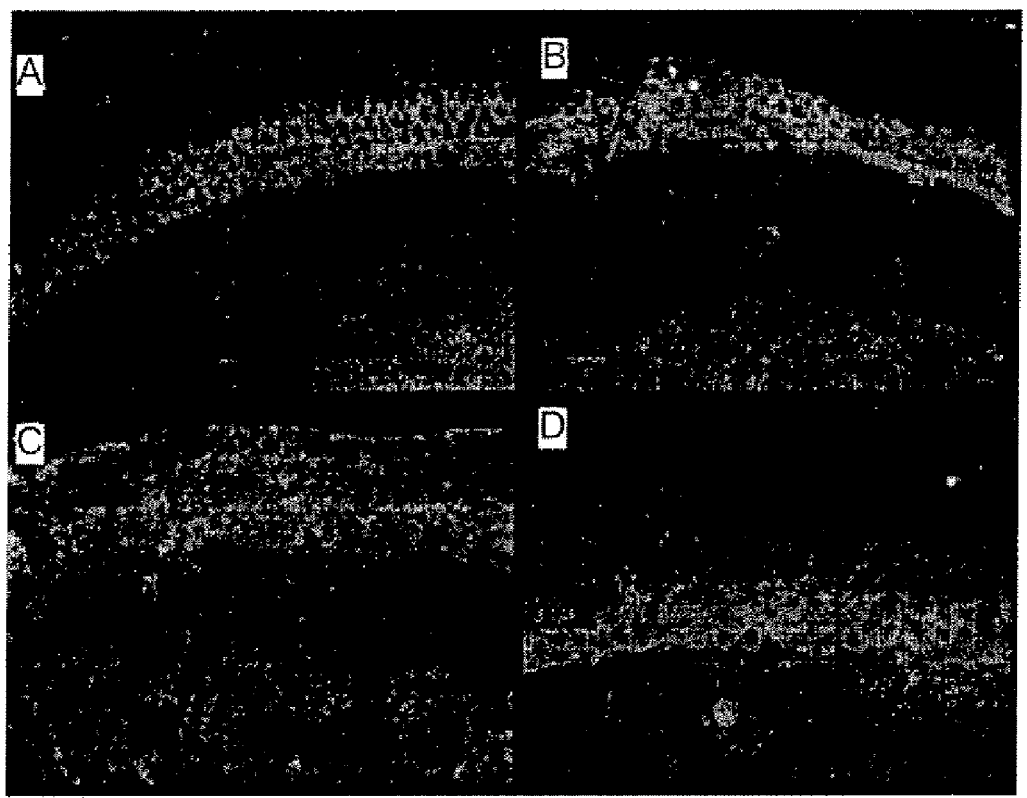

INHIBITION OF NEOMYCIN INDUCED-HAIR CELL LOSS
BY D-JNKI PEPTIDES IN NEONATAL COCHLEAR EXPLANTS

EXAMPLES (A-D) OF PHALLOIDIN AND TUNEL-FITC DOUBLE
LABELING OF MID-COCHLEAR TURNS PRETREATED WITH
5 μM D-JNKI FOR 24 h AND THEN CHALLENGED WITH 1 mM
NEOMYCIN IN THE PRESENCE OF D-JNK.
NOTE THAT PRE TREATMENT WITH D-JNKI GREATLY
PROTECTED HAIR CELLS FROM NEOMYCIN DAMAGE.

*FIG. 14B*

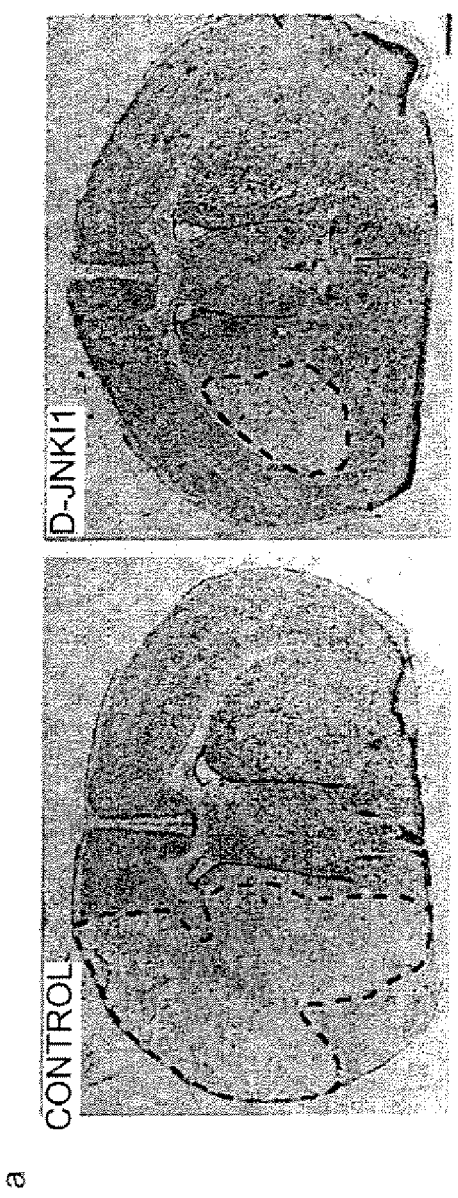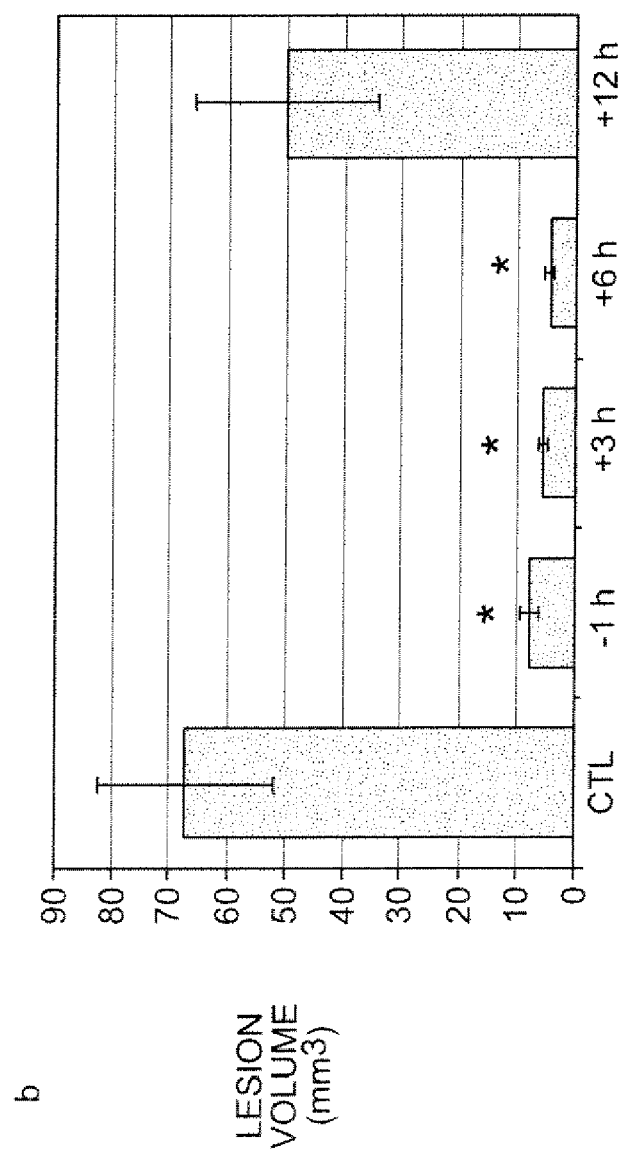
FIG. 19

US 8,236,924 B2

CELL-PERMEABLE PEPTIDE INHIBITORS OF THE JNK SIGNAL TRANSDUCTION PATHWAY

RELATED U.S. APPLICATION

This application is a divisional of U.S. Ser. No. 10/457,614, filed Jun. 9, 2003 now abandoned, which is incorporated herein by reference in its entirety.

FIELD OF THE INVENTION

This invention relates generally to protein kinase inhibitors and more specifically to inhibitors of the protein kinase c-Jun amino terminal kinase.

BACKGROUND OF THE INVENTION

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors, and receptor tyrosine kinases. In mammalian cells, JNK has been implicated in such biological processes as oncogenic transformation and in mediating adaptive responses to environmental stress. JNK has also been associated with modulating immune responses, including maturation and differentiation of immune cells, as well effecting programmed cell death in cells identified for destruction by the immune system.

SUMMARY OF THE INVENTION

The present invention is based in part on the discovery of peptides that are effective inhibitors of JNK proteins. The peptides, referred to herein as JNK peptide inhibitors, decrease the downstream cell-proliferative effects of c-Jun amino terminal kinase (JNK).

Accordingly, the invention includes novel JNK inhibitor peptides ("JNKI peptides"), as well as chimeric peptides which include a JNK peptide inhibitor linked a trafficking peptide that can be used to direct a peptide on which it is present do a desired cellular location. The trafficking sequence can be used to direct transport of the peptide across the plasma membrane. Alternatively, or in addition, the trafficking peptide can be used to direct the peptide to desired intracellular location, such as the nucleus.

The JNK inhibitor peptides can be present as polymers of L-amino acids. Alternatively, the peptides can be present as polymers of D-amino acids.

Also included in the invention are pharmaceutical compositions that include the JNK-binding peptides, as well as antibodies that specifically recognize the JNK-binding peptides.

The invention also includes a method of inhibiting expression of a JNK kinase in a cell.

In another aspect, the invention includes a method of treating a pathophysiology associated with activation of JNK in a cell or cells. For example, the target cells may be, e.g., cultured animal cells, human cells or micro-organisms. Delivery can be carried out in vivo by administering the chimeric peptide to an individual in whom it is to be used for diagnostic, preventative or therapeutic purposes. The target cells may be in vivo cells, i.e., cells composing the organs or tissues of living animals or humans, or microorganisms found in living animals or humans.

The invention further provides a method of preventing or treating hearing loss in a subject. The method includes administering to the subject a cell-permeable bioactive peptide which prevents damage to the hair cell stereocilia, hair cell apoptosis, or neuronal apoptosis. A cell-permeable bioactive peptide is, for example, a JNK-inhibitor peptide. Preferably, the cell-permeable bioactive peptide is SEQ ID NOs: 1, 2, 4, 5, 6, 11, 12, 13, 14, 15, or 16.

The hearing loss is caused by a noise trauma. Thus, in one aspect, the peptide is administered before the subject is exposed to a noise trauma. In another aspect, the peptide is administered after the subject is exposed to a noise trauma. The noise trauma can be, e.g., at least 90 dB SPL. Alternatively, the hearing loss is caused by antibiotic treatment. Thus, in one aspect, the peptide is administered before the subject is exposed to an antibiotic. In another aspect, the peptide is administered after the subject is exposed to an antibiotic. The antibiotic is, e.g., an aminoglycoside.

The hearing loss is caused by a chemotherapeutic agent. Thus, in one aspect, the peptide is administered before the subject is exposed to a chemotherapeutic agent. In another aspect, the peptide is administered after the subject is exposed to a chemotherapeutic agent.

The invention further provides a method of preventing or treating neuronal death or brain lesions in a subject. The method includes administering to the subject a cell-permeable bioactive peptide which prevents damage to the neurons or neuronal apoptosis. A cell-permeable bioactive peptide is, for example, a JNK-inhibitor ("JNKI") peptide. Preferably, the cell-permeable bioactive peptide is SEQ ID NOs:1, 2, 3, 4, 5, 6, 11, 12, 13, 14, 15, 16, or 21-28.

The neuronal death or brain lesions are caused by cerebral ischemia. Thus, in one aspect, the peptide is administered before the subject experiences an ischemic event. In another aspect, the peptide is administered after the subject experiences an ischemic event. The ischemic event is e, e.g., chronic or acute.

The neuronal death or brain lesions are caused by other excitotoxic mechanisms. Thus, in one aspect, the peptide is administered before the subject experiences an excitotoxic mechanism.

In another aspect, the peptide is administered after the subject experiences an excitotoxic mechanism. The excitotoxic mechanism can be, e.g., hypoxic/ischemic brain damage, traumatic brain damages, neuronal death arising from epileptic seizures, and several neurodegenerative disorders, such as Alzheimer's disease.

The invention also contemplates a method of inhibiting pancreatic islet cell death, where the method includes contacting a pancreatic islet cell with a cell-permeable bioactive peptide such that pancreatic cell death is inhibited. A cell-permeable bioactive peptide is, for example, a JNK-inhibitor peptide. Preferably, the cell-permeable bioactive peptide is SEQ ID NOs: 1, 2, 3, 4, 5, 6, 11, 12, 13, 14, 15, 16, or 21-28. The method can further include contacting the cell with collagenase.

Additionally, the invention contemplates a method of inhibiting pancreatic islet cell death in a subject by administering to the subject a cell-permeable bioactive peptide such that pancreatic cell death is inhibited. A cell-permeable bioactive peptide is, for example, a JNK-inhibitor peptide. Preferably, the cell-permeable bioactive peptide is SEQ ID NOs: 1, 2, 3, 4, 5, 6, 11, 12, 13, 14, 15, 16, or 21-28. The method can further include contacting the cell with collagenase. In one embodiment, the cell-permeable bioactive peptide is administered before the subject is exposed to a pro-inflammatory cytokine. In another embodiment, the cell-permeable bioactive peptide is administered after the subject is exposed to a pro-inflammatory cytokine In some aspects, the administration of the peptides of the invention can be by any one administration route selected from: intrauricular; intraperitoneal, nasal, intravenous, oral and patch delivery.

Among the advantages provided by the invention is that the JNK inhibitor peptides are small, and can be produced readily in bulk quantities and in high purity. The inhibitor peptides are also resistant to intracellular degradation, and are weakly immunogenic. Accordingly, the peptides are well suited for in vitro and in vivo applications in which inhibition of JNK-expression is desired.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIGS. 1A-C are diagrams showing alignments of conserved JBD domain regions in the indicated transcription factors.

FIG. 2 is a diagram showing alignments of generic TAT-IB fusion peptides.

FIG. 5 is a histogram depicting L-TAT-IB inhibition of phosphorylation by recombinant JNKs. Panel A shows L-TAT-IB inhibition of c-Jun, ATF2 and Elk1 phosphorylation by recombinant JNKs in vitro in the presence of MKK4. Panel B shows similar dose response experiments with MKK7.

FIG. 16A demonstrates the inhibitory effect of L-JNKI and D-JNKI on JNK activation and action in kinase assays with recombinant JNK1α1 and GST-Jun and GST-Elk1 substrates, respectively.

FIG. 16B demonstrates the inhibitory effect of the 20 amino acid minimal JNK-inhibitory sequence of JIP-IB1 (L-form of $JBD_{20}$) in dose response experiments, using conditions similar to those in FIG. 16A and with decreasing amounts of L-$JBD_{20}$.

FIG. 16C demonstrates the specificity of the JNKI peptides of the present invention in blocking JNK activation using kinase assays with different recombinant kinases.

In FIG. 17B, 4-fold more protein was loaded in the nuclear extracts (Nucl) than in the cytoplasmic ones (Cyt), and the abbreviations used are: C: Control; N: NMDA; L: L-JNKI+NMDA; D: D-JNKI+NMDA.

FIG. 17C illustrates the expression of c-fos relative to actin.

FIG. 18 contains a series of micrographs that depict Hoechst-stained neurons at 24 hours after NMDA treatment. FIG. 18 also contains a histogram depicting neuronal death at 12 h, 24 h, and 48 h after NMDA exposure (100 μM NMDA), as indicated by LDH activity.

FIG. 19 are illustrations and a histogram depicting transient ischemia in mice.

FIG. 19A demonstrates the effect on infarct volume of a pretreatment in which an intracerebro-ventricular (icv) injection of D-JNKI (15.7 ng in 2 μL phosphate buffer solution (PBS)) was administered to a subject 1 hour prior to occlusion.

FIG. 19B demonstrates the effect on infarct volume where the icv injection of D-JKNI was administered 1 hour prior to occlusion or at 3 hours, 6 hours and 12 hours post-occlusion.

FIG. 20A is a series of illustrations that depicts examples of lesions from a control rat (left panel) and a rat treated with D-JNKI 6 hours after occlusion (right panel).

FIG. 20B is a histogram depicting the infarct volumes, expressed as % of hemispheric volume, following the intra-peritoneal (i.p.) injection of D-JNKI at −0.5 h before or at +6 h or +12 h after occlusion.

FIG. 20C is a series of illustrations depicting the results of the immunohistochemistry for P-c-Jun in which c-Jun was phosphorylated in many neurons in the peri-infarcted cortex.

DETAILED DESCRIPTION OF THE INVENTION

Figure 3:
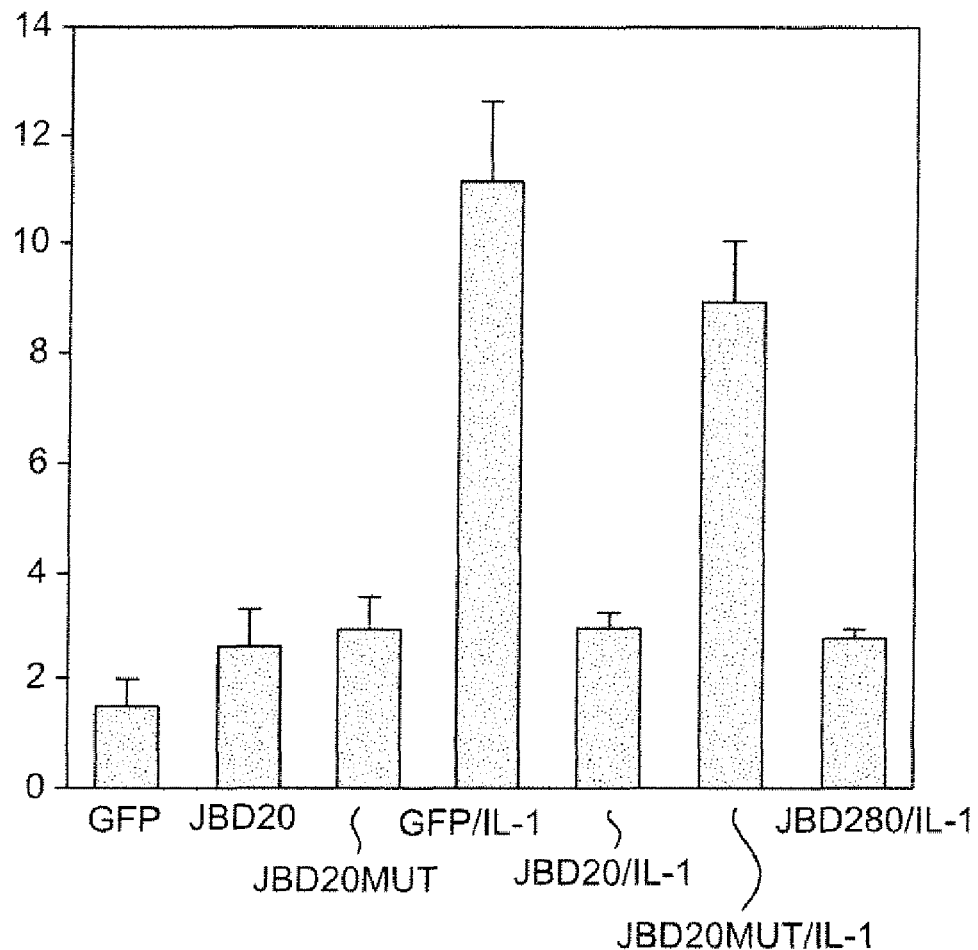
FIG. 3 is a histogram depicting inhibition of β-cell death by the minimal 23 amino acid long JBD domain of IB1 compared to the full 280 amino acid JBD domain.

The present invention is based in part on the discovery of cell permeable peptides that inhibit the activated c-Jun amino terminal kinase (JNK) signaling pathway. These peptides are referred to herein as JNK inhibitor peptides. Additionally, the discovery provides methods and pharmaceutical compositions for treating pathophysiologies associated with JNK signaling.

JNK inhibitor peptides were identified by inspecting sequence alignments between kJNK Binding Domains in various insulin binding (IB) proteins. The results of this alignment are shown in FIGS. 1A-1C. FIG. 1A depicts the region of highest homology between the JBDs of IB1, IB2, c-Jun and ATF2. Panel B depicts the amino acid sequence alignment of the JBDs of IB1 and IB2. Fully conserved residues are indicated by asterisks, while residues changed to Ala in the GFP-JBD$_{23Mut}$ vector are indicated by open circles. FIG. 1C shows the amino acid sequences of chimeric proteins that include a JNK inhibitor peptide domain and a trafficking domain. In the example shown, the trafficking domain is derived from the human immunodeficiency virus (HIV) TAT polypeptide, and the JNK inhibitor peptide is derived from an IB1 polypeptide. Human, mouse, and rat sequences are identical in Panels B and C.

Sequence comparison between the JNK binding domains of IB1 [SEQ ID NO: 17], IB2 [SEQ ID NO: 18], c-Jun [SEQ ID NO: 19] and ATF2 [SEQ ID NO: 20] revealed a partially conserved 8 amino acid sequence (FIG. 1A). A comparison of the JBDs of IB1 and IB2 further revealed two blocks of seven and three amino acids that are highly conserved between the two sequences. These two blocks are contained within a peptide sequence of 23 amino acids in IB1 [SEQ ID NO: 1] and 21 amino acids in IB2 [SEQ ID NO: 2]. The 20 amino acid minimal JNK-inhibitory sequence of JIP-IB1 (L-form of JBD$_{20}$ (SEQ ID NO:21)) is shown in FIG. 1C.

The JNK inhibitor peptides of the invention can be used in any situation in which inhibition of JNK activity is desired. This can include in vitro applications, ex vivo, and in vivo applications. As JNKs and all its isoforms participate in the development and establishment of pathological states or in pathways, the JNK peptides can be used to prevent or inhibit the occurrence of such pathological states. This includes prevention and treatment of diseases and prevention and treatment of conditions secondary to therapeutic actions. For example, the peptides of the present invention can be used to treat or prevent, e.g., diabetes, ionizing radiation, immune responses (including autoimmune diseases), ischemia/reperfusion injuries, heart and cardiovascular hypertrophies, and some cancers (e.g., Bcr-Abl transformation).

The peptides can also be used to inhibit expression of genes whose expression increases in the presence of an active JNK polypeptide. These genes and gene products includes, e.g., proinflammatory cytokines. Such cytokines are found in all forms of inflammatory, auto-inflammatory, immune and autoimmune diseases, degenerative diseases, myopathies, cardiomyopathies, and graft rejection.

The JNK inhibitor peptides described herein can also be used to treat or prevent effects associated with cellular shear stress, such as in pathological states induced by arterial hypertension, including cardiac hypertrophy and arteriosclerotic lesions, and at bifurcations of blood vessels, and the like; ionizing radiation, as used in radiotherapy and UV lights; free radicals; DNA damaging agents, including chemotherapeutic drugs; oncogenic transformation; neuronal and pancreatic cell damage, hearing loss, ischemia and reperfusion; hypoxia; and hypo- and hyperthermia.

The polynucleotides provided by the present invention can be used to express recombinant peptides for analysis, characterization or therapeutic use; as markers for tissues in which the corresponding peptides is preferentially expressed (either constitutively or at a particular stage of tissue differentiation or development or in disease states). Other uses for the nucleic acids include, e.g., molecular weight markers in gel electrophoresis-based analysis of nucleic acids.

The JNK inhibitor peptides disclosed herein are presented in Table 1. The table presents the name of the JNK inhibitor peptide, as well as its sequence identifier number, length, and amino acid sequence.

TABLE 1

| PEPTIDE NAME | SEQ ID | AA | Sequence |
|---|---|---|---|
| L-IB1 | 1 | 23 | DTYRPKRPTT LNLFPQVPRS QDT |
| L-IB2 | 2 | 21 | EEPHKHRPTT LRLTTLGAQD S |
| D-IB1 | 3 | 23 | TDQSRPVQPF LNLTTPRKPR YTD |
| D-IB2 | 4 | 21 | SDQAGLTTLR LTTPRHKHPE E |
| L-IB (generic) | 5 | 19 | XRPTTLXLXX XXXXXQDS/TX |
| D-IB (generic) | 6 | 19 | XS/TDQXXXXXX XLXLTTPRX |
| L-TAT | 7 | 10 | GRKKRRQRRR |
| D-TAT | 8 | 10 | RRRQRRKKRG |

TABLE 1-continued

| PEPTIDE NAME | SEQ ID | AA | Sequence |
|---|---|---|---|
| L-generic-TAT | 9 | 17 | XXXXRKKRRQ RRRXXXX |
| D-generic-TAT | 10 | 17 | XXXXRRRQRR KKRXXXX |
| L-TAT-IB1 | 11 | 35 | GRKKRRQRRR PPDTYRPKRP TTLNLFPQVP RSQDT |
| L-TAT-IB2 | 12 | 33 | GRKKRRQRRR PPEEPHKHRP TTLRLTTLGA QDS |
| L-TAT-IB (generic) | 13 | 42 | XXXXXXXRKK RRQRRRXXXX XXXXRPTTLX LXXXXXXXQD S/TX |
| D-TAT-IB1 | 14 | 35 | TDQSRPVQPF LNLTTPRKPR YTDPPRRRQR RKKRG |
| D-TAT-IB2 | 15 | 33 | SDQAGLTTLR LTTPRHKHPE EPPRRRQRRK KRG |
| D-TAT-IB (generic) | 16 | 42 | XT/SDQXXXXXX XLXLTTPRXX XXXXXXRRRQ RRKKRXXXXX XX |
| IB1-long | 17 | 29 | PGTGCGDTYR PKRPTTLNLF PQVPRSQDT |
| IB2-long | 18 | 27 | IPSPSVEEPH KHRPTTLRLT TLGAQDS |
| c-Jun | 19 | 29 | GAYGYSNPKI LKQSMTLNLA DPVGNLKPH |
| ATF2 | 20 | 29 | TNEDHLAVHK HKHEMTLKFG PARNDSVIV |
| L-JBD$_{20}$ | 21 | 20 | RPKRPTTLNL FPQVPRSQDT |
| D-JBD$_{20}$ | 22 | 20 | TDQSRPVQPF LNLTTPRKPR |
| L-TAT-JNK11 (i.e., L-TAT-JBD$_{20}$) | 23 | 32 | GRKKRRQRRR PPRPKRPTTL NLFPQVPRSQ DT |
| D-TAT-JNK11 (i.e., D-TAT-JBD$_{20}$) | 24 | 32 | TDQSRPVQPF LNLTTPRKPR PPRRRQR RKKRG |
| L-TAT-JNK11 (generic) | 25 | 34 | XXXXRKKRRQ RRRXXXXRPT TLXLXXXXXX XQDS/T |
| D-TAT-JNK11 (generic) | 26 | 34 | S/TDQXXXXXXX LXLTTPRXXX XRRRQRRKKR XXXX |
| L-JBD$_{20}$-mut | 27 | 20 | RPKRPTAANA FPQVPRSQDT |
| D-JBD$_{20}$-mut | 28 | 20 | TDQSRPVAPF ANAATPRKPR |

JNK Inhibitor Peptides

In one aspect, the invention provides a JNK inhibitor peptide. No particular length is implied by the term "peptide." In some embodiments, the JNK-inhibitor peptide is less than 280 amino acids in length, e.g., less than or equal to 150, 100, 75, 50, 35, or 25 amino acids in length. In various embodiment, the JNK-binding inhibitor peptide includes the amino acid sequence of one or more of SEQ ID NOs: 1-6 and 21-22. In one embodiment, the JNK inhibitor peptide peptides bind JNK. In another embodiment the peptide inhibits the activation of at least one JNK activated transcription factor, e.g. c-Jun, ATF2 or Elk1.

Examples of JNK inhibitor peptides include a peptide which includes (in whole or in part) the sequence NH$_2$-DTYR-PKRPTTLNLFPQVPRSQDT-COOH [SEQ ID NO: 1]. In another embodiment, the peptide includes the sequence NH$_2$-EEPHKHRPTTLRLTTLGAQDS-COOH [SEQ ID NO:2] Alternatively, examples of JNK inhibitor peptides include a peptide which includes (in whole or in part) the sequence NH$_2$-RPKRPTTLNL FPQVPRSQDT-COOH [SEQ ID NO:21].

The JNK inhibitor peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed, the term "D-retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

For example, a D retro-inverso peptide has the sequence NH$_2$-TDQSRPVQPFLNLTTPRKPRYTD-COOH [SEQ ID NO:3] or NH$_2$-SDQAGLTTLRLTTPRHKHPEE-COOH [SEQ ID NO: 4]. Alternatively, a D retro-inverso peptide includes the sequence NH$_2$-TDQSRPVQPF LNLTTPRKPR-COOH [SEQ ID NO:22]. It has been unexpectedly found that D-retro-inverso peptides have a variety of useful properties. For example, D-TAT and D-TAT-IB and D-TAT-JNKI peptides enter cells as efficiently as L-TAT and L-TAT-IB and D-TAT-JNKI peptides, and D-TAT and D-TAT-IB and D-TAT-JNKI peptides are more stable than the corresponding L-peptides. Further, while D-TAT-IB1 are ~10-20 fold less efficient in inhibiting JNK than L-TAT-IB and L-TAT-JNKI, they are ~50 fold more stable in vivo. Moreover, the D-retroinverso JNKI peptides are protease-resistant. Finally, as is discussed further below, D-TAT-IB and D-TAT-JNKI peptides protect interleukin-1 treated and ionizing irradiated cells from apoptosis, and these peptides are useful in treating neurons, as the TAT sequence contains six pairs of amino acid that render the TAT sequence extremely sensitive to the neuronal proteases that are involved in peptide processing in the nervous system. See e.g., Steiner et al., *J. Biol. Chem.* 267: 23435-23438 (1992); Brugidou et al., *Biochem. & Biophys. Res. Comm.* 214:685-693 (1995); each of which is incorporated herein by reference in its entirety.

A JNK inhibitor peptide according to the invention includes the amino acid sequence $NH_2$-$X_n$-RPTTLX-LXXXXXXXQDS/T-$X_n$-COOH [SEQ ID NO: 5, and residues 17-42 of L-TAT-IB, SEQ ID NO: 13, as shown in FIG. 2]. As used herein, $X_n$ may be zero residues in length, or may be a contiguous stretch of peptide residues derived from SEQ ID NOS:1 and 21, preferably a stretch of between 1 and 7 amino acids in length, or may be 10, 20, 30 or more amino acids in length. The single residue represented by S/T may be either Ser or Thr in the generic sequence. In a further embodiment, a JNK inhibitor peptide of the invention may be a D retro-inverso peptide having the sequence $NH_2$-$X_n$-S/TDQXXXXXXXLXLTTPR-$X_n$-COOH [SEQ ID NO: 6], and residues 17-42 of L-TAT-IB, SEQ ID NO: 16, as shown in FIG. 2].

JNK-inhibitor peptides are obtained or produced by methods well-known in the art, e.g. chemical synthesis, genetic engineering methods as discussed below. For example, a peptide corresponding to a portion of a JNK inhibitor peptide including a desired region or domain, or that mediates the desired activity in vitro, may be synthesized by use of a peptide synthesizer.

A candidate JNK inhibitor peptide is analyzed by hydrophilicity analysis (see, e.g., Hopp and Woods, 1981. *Proc Natl Acad Sci USA* 78: 3824-3828) that can be utilized to identify the hydrophobic and hydrophilic regions of the peptides, thus aiding in the design of substrates for experimental manipulation, such as in binding experiments, antibody synthesis. Secondary structural analysis may also be performed to identify regions of a JNK inhibitor peptide that assume specific structural motifs. See e.g., Chou and Fasman, 1974. *Biochem* 13: 222-223. Manipulation, translation, secondary structure prediction, hydrophilicity and hydrophobicity profiles, open reading frame prediction and plotting, and determination of sequence homologies can be accomplished using computer software programs available in the art. Other methods of structural analysis including, e.g., X-ray crystallography (see, e.g., Engstrom, 1974. *Biochem Exp Biol* 11: 7-13); mass spectroscopy and gas chromatography (see, e.g., METHODS IN PROTEIN SCIENCE, 1997. J. Wiley and Sons, New York, N.Y.) and computer modeling (see, e.g., Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

The present invention additionally relates to nucleic acids that encode JNK-binding peptides having L-form amino acids, e.g., those L-peptides indicated in Table 1, as well as the complements of these sequences.

Nucleic acids encoding the JNK inhibitor peptides may be obtained by any method known in the art (e.g., by PCR amplification using synthetic primers hybridizable to the 3'- and 5'-termini of the sequence and/or by cloning from a cDNA or genomic library using an oligonucleotide sequence specific for the given gene sequence).

For recombinant expression of one or more JNK inhibitor peptides, the nucleic acid containing all or a portion of the nucleotide sequence encoding the peptide may be inserted into an appropriate expression vector (i.e., a vector that contains the necessary elements for the transcription and translation of the inserted peptide coding sequence). In some embodiments, the regulatory elements are heterologous (i.e., not the native gene promoter). Alternately, the necessary transcriptional and translational signals may also be supplied by the native promoter for the genes and/or their flanking regions.

A variety of host-vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Promoter/enhancer sequences within expression vectors may utilize plant, animal, insect, or fungus regulatory sequences, as provided in the invention. For example, promoter/enhancer elements can b used from yeast and other fungi (e.g., the GAL4 promoter, the alcohol dehydrogenase promoter, the phosphoglycerol kinase promoter, the alkaline phosphatase promoter). Alternatively, or in addition, they may include animal transcriptional control regions, e.g., (i) the insulin gene control region active within pancreatic β-cells (see, e.g., Hanahan, et al., 1985. *Nature* 315: 115-122); (ii) the immunoglobulin gene control region active within lymphoid cells (see, e.g., Grosschedl, et al., 1984. *Cell* 38: 647-658); (iii) the albumin gene control region active within liver (see, e.g., Pinckert, et al., 1987. *Genes and Dev* 1: 268-276; (iv) the myelin basic protein gene control region active within brain oligodendrocyte cells (see, e.g., Redhead, et al., 1987. *Cell* 48: 703-712); and (v) the gonadotropin-releasing hormone gene control region active within the hypothalamus (see, e.g., Mason, et al., 1986. *Science* 234: 1372-1378), and the like.

Expression vectors or their derivatives include, e.g. human or animal viruses (e.g., vaccinia virus or adenovirus); insect viruses (e.g., baculovirus); yeast vectors; bacteriophage vectors (e.g., lambda phage); plasmid vectors and cosmid vectors.

A host cell strain may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptides. Moreover, different host cells possess characteristic and specific mechanisms for the translational and post-translational processing and modification (e.g., glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

Also included in the invention are derivatives, fragments, homologs, analogs and variants of JNK inhibitor peptides and nucleic acids encoding these peptides. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments are less than the length of the corresponding full-length nucleic acid or polypeptide from which the JNK inhibitor peptide, or nucleic acid encoding same, is derived. Derivatives and analogs may be full length or other than full length, if the derivative or analog contains a modified nucleic acid or amino acid. Derivatives or analogs of the JNK inhibitor peptides include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Thus, included in the invention are peptides having mutated sequences such that they remain homologous, e.g. in sequence, in function, and in antigenic character or other function, with a protein having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

The invention also encompasses allelic variants of the disclosed polynucleotides or peptides; that is, naturally-occurring alternative forms of the isolated polynucleotide that also encode peptides that are identical, homologous or related to that encoded by the polynucleotides. Alternatively, non-naturally occurring variants may be produced by mutagenesis techniques or by direct synthesis.

Species homologs of the disclosed polynucleotides and peptides are also provided by the present invention. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non-coding regions, or both.

In some embodiments, altered sequences include insertions such that the overall amino acid sequence is lengthened while the protein retains trafficking properties. Additionally, altered sequences may include random or designed internal deletions that shorten the overall amino acid sequence while the protein retains transport properties.

The altered sequences can additionally or alternatively be encoded by polynucleotides that hybridize under stringent conditions with the appropriate strand of the naturally-occurring polynucleotide encoding a polypeptide or peptide from which the JNK inhibitor peptide is derived. The variant peptide can be tested for JNK-binding and modulation of JNK-mediated activity using the herein described assays. 'Stringent conditions' are sequence dependent and will be different in different circumstances. Generally, stringent conditions can be selected to be about 5° C. lower than the thermal melting point ($T_M$) for the specific sequence at a defined ionic strength and pH. The $T_M$ is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

High stringency can include, e.g., Step 1: Filters containing DNA are pretreated for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Step 2: Filters are hybridized for 48 hours at 65° C. in the above prehybridization mixture to which is added 100 mg/ml denatured salmon sperm DNA and 5-20×10$^6$ cpm of $^{32}$P-labeled probe. Step 3: Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Step 4: Filters are autoradiographed. Other conditions of high stringency that may be used are well known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Moderate stringency conditions can include the following: Step 1: Filters containing DNA are pretreated for 6 hours at 55° C. in a solution containing 6×SSC, 5×Denhardt's solution, 0.5% SDS and 100 mg/ml denatured salmon sperm DNA. Step 2: Filters are hybridized for 18-20 hours at 55° C. in the same solution with 5-20×106 cpm $^{32}$P-labeled probe added. Step 3: Filters are washed at 37° C. for 1 hour in a solution containing 2×SSC, 0.1% SDS, then washed twice for 30 minutes at 60° C. in a solution containing 1×SSC and 0.1% SDS. Step 4: Filters are blotted dry and exposed for autoradiography. Other conditions of moderate stringency that may be used are well-known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Low stringency can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5-20× 106 cpm $^{32}$P-labeled probe. Step 3: Filters are washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g., as employed for cross-species hybridizations). See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Chimeric Peptides Including a JNK Inhibitor Domain and a Trafficking Domain

In another aspect the invention provides a chimeric peptide that includes a first and second domain. The first domain includes a trafficking sequence, while the second domain includes a JNK inhibitor sequence linked by a covalent bond, e.g. peptide bond, to the first domain. The first and second domains can occur in any order in the peptide, and the peptide can include one or more of each domain.

A trafficking sequence is any sequence of amino acids that directs a peptide in which it is present to a desired cellular destination. Thus, the trafficking sequence can direct the peptide across the plasma membrane, e.g., from outside the cell, through the plasma membrane, and into the cytoplasm. Alternatively, or in addition, the trafficking sequence can direct the peptide to a desired location within the cell, e.g., the nucleus, the ribosome, the ER, a lysosome, or peroxisome.

In some embodiments, the trafficking peptide is derived from a known membrane-translocating sequence. For example, the trafficking peptide may include sequences from the human immunodeficiency virus (HIV) 1 TAT protein. This protein is described in, e.g., U.S. Pat. Nos. 5,804,604 and 5,674,980, each incorporated herein by reference. The JNK inhibitor peptide is linked to some or all of the entire 86 amino acids that make up the TAT protein. For example, a functionally effective fragment or portion of a TAT protein that has fewer than 86 amino acids, which exhibits uptake into cells, and optionally uptake into the cell nucleus, can be used. See e.g., Vives et al., J. Biol. Chem., 272(25):16010-17 (1997), incorporated herein by reference in its entirety. In one embodiment, the fragment includes a peptide containing TAT residues 48-57, e.g. $NH_2$-GRKKRRQRRR-COOH [SEQ ID NO: 7] or a generic TAT sequence $NH_2$-$X_n$-RKKRRQRRR-$X_n$-COOH [SEQ ID NO: 9]. A TAT peptide that includes the region that mediates entry and uptake into cells can be further defined using known techniques. See, e.g., Franked et al., Proc. Natl. Acad. Sci, USA 86: 7397-7401 (1989).

The TAT sequence may be linked either to the N-terminal or the C-terminal end of JNK inhibitor sequence. A hinge of two proline residues may be added between the TAT and JNK inhibitor peptide to create the full fusion peptide. For example, L-amino acid fusion peptides may be the L-TAT-IB1 peptide [SEQ ID NO: 11], the L-TAT-IB2 peptide [SEQ ID NO: 12], or the generic L-TAT-IB peptide [SEQ ID NO: 13]. Alternatively, L-amino acid fusion peptides may be the L-TAT-JNKI1 peptide [SEQ ID NO:23] or the generic L-TAT-JNKI1 peptide [SEQ ID NO:25]. D retro-inverso fusion peptides may be the D-TAT-IB1 peptide [SEQ ID NO: 14], the D-TAT-IB2 peptide [SEQ ID NO:15], or the generic D-TAT-IB peptide [SEQ ID NO:16]. Alternatively, D retro-inverso fusion peptides may be the D-TAT-JNKI1 peptide [SEQ ID NO:24] or the generic D-TAT-JNKI1 peptide [SEQ ID NO:26]. The TAT peptide may be a D retro-inverso peptide having the sequence $NH_2$-$X_n$-RRRQRRKKR-$X_n$-COOH [SEQ ID NO: 10]. In SEQ ID NOs:5-6, 9-10, 13, 16, and 25-26, the number of "X" residues is not limited to the one depicted and can equal any number of amino acid residues, including zero, and may vary as described above.

The trafficking sequence can be a single (i.e., continuous) amino acid sequence present in the TAT sequence. Alternatively it can be two or more amino acid sequences, which are present in TAT protein, but in the naturally-occurring protein are separated by other amino acid sequences. As used herein, TAT protein includes a naturally-occurring amino acid sequence that is the same as that of naturally-occurring TAT protein, or its functional equivalent protein or functionally equivalent fragments thereof (peptides). Such functional equivalent proteins or functionally equivalent fragments possess uptake activity into the cell and into the cell nucleus that is substantially similar to that of naturally-occurring TAT protein. TAT protein can be obtained from naturally-occurring sources or can be produced using genetic engineering techniques or chemical synthesis.

The amino acid sequence of naturally-occurring HIV TAT protein can be modified, for example, by addition, deletion and/or substitution of at least one amino acid present in the naturally-occurring TAT protein, to produce modified TAT protein (also referred to herein as TAT protein). Modified TAT protein or TAT peptide analogs with increased or decreased stability can be produced using known techniques. In some embodiments TAT proteins or peptides include amino acid sequences that are substantially similar, although not identical, to that of naturally-occurring TAT protein or portions thereof. In addition, cholesterol or other lipid derivatives can be added to TAT protein to produce a modified TAT having increased membrane solubility.

Variants of the TAT protein can be designed to modulate intracellular localization of TAT-JNK inhibitor peptide. When added exogenously, such variants are designed such that the ability of TAT to enter cells is retained (i.e., the uptake of the variant TAT protein or peptide into the cell is substantially similar to that of naturally-occurring HIV TAT). For example, alteration of the basic region thought to be important for nuclear localization (see, e.g., Dang and Lee, J. Biol. Chem. 264: 18019-18023 (1989); Hauber et al., J. Virol. 63: 1181-1187 (1989); Ruben et al., J. Virol. 63: 1-8 (1989)) can result in a cytoplasmic location or partially cytoplasmic location of TAT, and therefore, of the JNK inhibitor peptide. Alternatively, a sequence for binding a cytoplasmic or any other component or compartment (e.g., endoplasmic reticulum, mitochondria, gloom apparatus, lysosomal vesicles,) can be introduced into TAT in order to retain TAT and the JNK inhibitor peptide in the cytoplasm or any other compartment to confer regulation upon uptake of TAT and the JNK inhibitor peptide.

Other sources for the trafficking peptide include, e.g., VP22 (described in, e.g., WO 97/05265; Elliott and O'Hare, Cell 88: 223-233 (1997)), or non-viral proteins (Jackson et al, Proc. Natl. Acad. Sci. USA 89: 10691-10695 (1992)).

The JNK inhibitor sequence and the trafficking sequence can be linked by chemical coupling in any suitable manner known in the art. Many known chemical cross-linking methods are non-specific, i.e.; they do not direct the point of coupling to any particular site on the transport polypeptide or cargo macromolecule. As a result, use of non-specific cross-linking agents may attack functional sites or sterically block active sites, rendering the conjugated proteins biologically inactive.

One way to increasing coupling specificity is to directly chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, CHEMICAL MODIFICATION OF PROTEINS, Holden-Day, 1974, pp. 39-43. Among these reagents are, for example, J-succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonyl-chloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl) cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis (succinimidylpropionate) ("DSP"), and N-succinimidyl 3-(2-pyridyldithio) propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, CHEMISTRY OF PROTEIN CONJUGATION AND CROSS-LINKING, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., cat. No. 21651H).

Alternatively, the chimeric peptide can be produced as a fusion peptide that includes the trafficking sequence and the JNK inhibitor sequence which can conveniently be expressed in known suitable host cells. Fusion peptides, as described herein, can be formed and used in ways analogous to or readily adaptable from standard recombinant DNA techniques, as describe above.

Production of Antibodies Specific for JNK Inhibitor Peptides

JNK inhibitor peptides, including chimeric peptides including the JNK inhibitor peptides (e.g., peptides including the amino acid sequences shown in Table 1), as well peptides, or derivatives, fragments, analogs or homologs thereof, may be utilized as immunogens to generate antibodies that immunospecifically-bind these peptide components. Such antibodies include, e.g., polyclonal, monoclonal, chimeric, single chain, Fab fragments and a Fab expression library. In a specific embodiment, antibodies to human peptides are disclosed. In another specific embodiment, fragments of the JNK inhibitor peptides are used as immunogens for antibody production. Various procedures known within the art may be used for the production of polyclonal or monoclonal antibodies to a JNK inhibitor peptide, or derivative, fragment, analog or homolog thereof.

For the production of polyclonal antibodies, various host animals may be immunized by injection with the native peptide, or a synthetic variant thereof, or a derivative of the foregoing. Various adjuvants may be used to increase the immunological response and include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.) and human adjuvants such as *Bacille Calmette-Guerin* and *Corynebacterium parvum*.

For preparation of monoclonal antibodies directed towards a JNK inhibitor peptide, or derivatives, fragments, analogs or homologs thereof, any technique that provides for the production of antibody molecules by continuous cell line culture may be utilized. Such techniques include, but are not limited to, the hybridoma technique (see, Kohler and Milstein, 1975. *Nature* 256: 495-497); the trioma technique; the human B-cell hybridoma technique (see, Kozbor, et al., 1983. *Immunol Today* 4: 72) and the EBV hybridoma technique to produce human monoclonal antibodies (see, Cole, et al., 1985. In: *Monoclonal Antibodies and Cancer Therapy*, Alan R. Liss, Inc., pp. 77-96). Human monoclonal antibodies may be utilized in the practice of the present invention and may be produced by the use of human hybridomas (see, Cote, et al., 1983. *Proc Natl Acad Sci USA* 80: 2026-2030) or by transforming human B-cells with Epstein Barr Virus in vitro (see, Cole, et al., 1985. In: *Monoclonal Antibodies and Cancer Therapy* (Alan R. Liss, Inc., pp. 77-96).

According to the invention, techniques can be adapted for the production of single-chain antibodies specific to a JNK inhibitor peptide (see, e.g., U.S. Pat. No. 4,946,778). In addition, methodologies can be adapted for the construction of Fab expression libraries (see, e.g., Huse, et al., 1989. *Science* 246: 1275-1281) to allow rapid and effective identification of monoclonal Fab fragments with the desired specificity for a JNK inhibitor peptide or derivatives, fragments, analogs or homologs thereof. Non-human antibodies can be "humanized" by techniques well known in the art. See e.g., U.S. Pat. No. 5,225,539. Antibody fragments that contain the idiotypes to a JNK inhibitor peptide may be produced by techniques known in the art including, e.g., (i) an $F(ab')_2$ fragment produced by pepsin digestion of an antibody molecule; (ii) an Fab fragment generated by reducing the disulfide bridges of an $F(ab')_2$ fragment; (iii) an Fab fragment generated by the treatment of the antibody molecule with papain and a reducing agent and (iv) Fv fragments.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a JNK inhibitor peptide is facilitated by generation of hybridomas that bind to the fragment of a JNK inhibitor peptide possessing such a domain. Antibodies that are specific for a domain within a JNK inhibitor peptide, or derivative, fragments, analogs or homologs thereof, are also provided herein.

The anti-JNK inhibitor peptide antibodies may be used in methods known within the art relating to the localization and/or quantitation of a JNK inhibitor peptide (e.g., for use in measuring levels of the peptide within appropriate physiological samples, for use in diagnostic methods, for use in imaging the peptide, and the like). In a given embodiment, antibodies for the JNK inhibitor peptides, or derivatives, fragments, analogs or homologs thereof that contain the antibody derived binding domain, are utilized as pharmacologically active compounds (hereinafter "Therapeutics").

Methods of Treating or Preventing Disorders

Disorders Associated Undesired JNK Activity

Also included in the invention also are methods of treating cell-proliferative disorders associated with JNK activation in a subject by administering to a subject a biologically-active therapeutic compound (hereinafter "Therapeutic").

The term "cell-proliferative disorder" denotes malignant as well as non-malignant cell populations that often appear to differ morphologically and functionally from the surrounding tissue. For example, the method may be useful in treating malignancies of the various organ systems, in which activation of JNK has often been demonstrated, e.g., lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus. Cancers with Bcr-Abl oncogenic transformations that clearly require activation of JNK are also included.

The method is also useful in treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, septic shock and other types of acute inflammation, and lipid histiocytosis. Especially preferred are immunopathological disorders. Essentially, any disorder, which is etiologically linked to JNK kinase activity, would be considered susceptible to treatment.

Hearing Loss

Also included in the invention are methods of preventing or treating hearing loss by administering to a subject a Therapeutic, i.e., a cell-permeable bioactive peptide where the peptide prevents damage to the hair cell stereocilia, hair cell apoptosis or neuronal apoptosis. Preferably, the Therapeutic is the peptide of SEQ ID NO: 1, 2, 3, 4, 5, 6, 11, 12, 13, 14, 15, 16, 21, 22, 23, 24, 25, 26, 27 or 28.

Exposure to loud noise causes noise-induced hearing loss (NIHL) by damaging the organs of the Corti, Damage an NIHL depends upon both the level of the noise and the duration of the exposure. Hearing loss may be temporary (TTS) if a repair mechanism is able to restore the organ of the Corti, However it becomes permanent (PTS) when hair cells or neurons die. Structural correlates to noise trauma are of two types: (1) mild damage of synapses and or hair cell stereocilia which can be repaired and accounts for TTS and recovery and (2) severe damage inducing hair cell and neuronal apoptosis which can not be repaired and accounts for PTS.

The Therapeutic is administered to the subject before exposure to a noise trauma, antibiotic or chemotherapeutic agent. Alternatively, the Therapeutic is administers after the subject is exposed to a noise trauma, antibiotic or chemotherapeutic agent.

A noise trauma is a noise which is sufficient to cause damage to the corti. For example a noise trauma us at least 70 dB SPL, at least 90 dB SPL or at least 100 dB SPL, at least 120 dB SPL or at least 130 dB SPL.

Antibiotics include for example penicillins such as penicillin G, penicillin V, ampicillin, amoxicillin, dicloxacillin, and oxacillin; cephalosporins such as cephalexin (Keflex), cefaclor (Ceclor), and cefixime (Suprax); aminoglycoside such as tobramycin, and streptomycin; macrolides, such as erythromycin, azithromycin (Zithromax) and clarithromycin; sulfonamides such as trimethoprim-sulfamethoxazole or tetracylines such as tetracycline, or doxycycline.

Neuronal Disorders

Also included in the invention are methods of treating or preventing neuronal cell death related disorders by administering to a cell or subject a composition of a cell-permeable bioactive peptide where the peptide prevents damage to neurons or neuronal apoptosis. The composition is for example the peptide of SEQ ID NO:1, 2, 3, 4, 5, 6, 11, 12, 13, 14, 15, 16, or 21-26. Preferably, the composition function to inhibit excitotoxic or oxidative stress-induced death of neuronal cells. A neuronal cell is any cell derived from the central or peripheral nervous system, e.g., neuron, neurite or dendrite. The cell is contacted in vivo, ex vivo or in vitro. The subject is e.g., any mammal, e.g., a human, a primate, mouse, rat, dog, cat, cow, horse, pig.

Neuronal cell death is measure by methods known in the art. For example cell death is determined microscpopy or using a chemical indicator such as Calcein-am (Molecular Probes).

Excitotoxicity is the main mechanism underlying neuronal death in stroke, anoxic and traumatic brain damage is excitotoxicity. Excitotoxicity is triggered by the excessive activation of ionotropic glutamate-receptors, particularly, the N-methyl-D-aspartate subtype of receptor, thereby leading to the rapid influx of $Ca^{2+}$ that triggers cell death. See e.g., Dirnagl et al., *Trends in Neurosci.* 22:391-97 (1999); Zipfel et al., *J. of Neurotrauma* 17:857-69 (2000).

The methods are useful to alleviate the symptoms of a variety of neuronal disorders. The neuronal disorder is acute or chronic. Neuronl disorder include those associated with n excitotoxic event such as ischemic stroke, cerebral ischemia, hypoxic/ischemic brain damage, traumatic brain damage, neuronal death arising from epileptic seizures, and neuronal death associated with several neurodegenerative disorders, such as Alzheimer's disease, amyotrophic lateral sclerosis (ALS), and Huntington's disease.

Neuronal death in cerebral ischemia is associated with excitotoxic mechanisms. Cerebral ischemia (e.g., global cerebral ischemia and focal cerebral ischemia) is due to stroke, head injury or cardiac arrest. Global cerebral ischemia results from cardiac arrest or bilateral carotid artery occlusion. Focal cerebral ischemia results from a reduction in the cerebral blood flow following cerebral artery occlusion. Focal cerebral ischemia results in necrotic neuronal death by a complex pathogenic cascade of events that includes energy depletion, excitotoxicity, and peri-infarct depolarization, as well as a more delayed mechanism involving both apoptosis and inflammation. Focal cerebral ischemia can be further divided into thrombotic or embolic focal ischemia. A thrombotic stroke occurs when cerebral arteries become blocked by a blood clot that is formed within the brain. An embolic stroke is also caused by a clotted artery, but in embolic stroke, the clot is formed somewhere other than in the brain itself.

The methods described herein lead to a reduction in the severity or the alleviation of one or more symptoms of an neuronal disorder such as those described herein. Neuronal disorders are diagnosed and or monitored, typically by a physician using standard methodologies.

The JNKI peptides of the invention have been shown, as described in the Examples, to provide high levels of neuroprotection, and moreover, the level of protection remains high even when the JNKI peptide is administered 6-12 hours after the onset of ischemia. While 30-50% neuroprotection has been demonstrated with various compounds administered up to 9 hours post-ischemia (see e.g., Fink et al., *J. Cereb. Blood Flow Metab.*, 18:1071-76 (1998); Williams et al., *Neurore-port,* 13:821-24 (2002), each of which is hereby incorporated by reference in its entirety), the JNKI peptides of the present invention have been shown to provide protection when administered 12 hours after the ischemic event, as described in the Examples below.

Most patients that are experiencing, or have experienced, an excitotoxic event, such as an ischemic stroke, seek medical assistance within 3 to 6 hours following the excitotoxic event. The length of time available to treat or prevent excitotoxic damage, such as the damage that occurs in an ischemic event, is important, as activation of the cell death machinery can take several hours following the excitotoxic event. Accordingly, the Therapeutic can be administered to the subject before experiencing an excitotoxic event. Alternatively, the Therapeutic can be administered after the subject experiences an excitotoxic event.

Inhibiting Pancreatic Islet Cell Death

Also include are methods of inhibiting cell damage or death or preventing aberrant cell damage such as oxidative-stress induced cell death (e.g., apoptotic cell death) by administering to a subject a bioactive therapeutic administering to a cell or subject a composition (Therapeutic) containing a bioactive peptide where the peptide prevents cell death or damage. The cell is for example a pancreatic cell. Preferably, the Therapeutic is the peptide of SEQ ID NO: 1, 2, 3, 4, 5, 6, 11, 12, 13, 14, 15, 16, or 21-26. Optionally, the cell or subject is also administered collagenase.

The peptide is administered either before or after the subject is exposed to a pro-inflammatory cytokine such as the interleukins.

The subject can be e.g., any mammal, e.g., a human, a primate, mouse, rat, dog, cat, cow, horse, pig.

Pharmaceutical Compositions

The Therapeutics include, e.g.: (i) any one or more of the JNK inhibitor peptides, and derivative, fragments, analogs and homologs thereof, (ii) antibodies directed against the JNK inhibitor peptides; (iii) nucleic acids encoding a JNK inhibitor peptide, and derivatives, fragments, analogs and homologs thereof, (iv) antisense nucleic acids to sequences encoding a JNK inhibitor peptide, and (v) modulators (i.e., inhibitors, agonists and antagonists).

The term "therapeutically effective" means that the amount of inhibitor peptide, for example, which is used, is of sufficient quantity to ameliorate the JNK associated disorder.

Treatment includes administration of a reagent that modulates JNK kinase activity. The term "modulate" includes the suppression of expression of JNK when it is over-expressed. It also includes suppression of phosphorylation of c-jun, ATF2 or NFAT4, for example, by using a peptide of any one or more of SEQ ID NOs: 1-6, and 21-22 and SEQ ID NOs: 11-16 and 23-26 as a competitive inhibitor of the natural c-jun ATF2 and NFAT4 binding site in a cell. Thus also includes suppression of hetero- and homo-meric complexes of transcription factors made up of c-jun, ATF2, or NFAT4 and their related partners, such as for example the AP-1 complex that is made up of c-jun, AFT2 and c-fos. When a cell proliferative disorder is associated with JNK overexpression, such suppressive JNK inhibitor peptides can be introduced to a cell. In some instances, "modulate" may include the increase of JNK expression, for example by use of an IB peptide-specific antibody that blocks the binding of an IB-peptide to JNK, thus preventing JNK inhibition by the IB-related peptide. The JNK inhibitor, peptides, fusion peptides and nucleic acids of the invention can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal, intrauricular, or patch routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, e.g. in a viral vector (a variant of the VDEPT technique—see below). The vector could be targeted to the specific cells to be treated, or it could contain regulatory elements, which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. a JNK inhibitor peptide, in a vector by expression from encoding DNA in a viral vector (see for example, EP-A-415731 and WO 90/07936).

In a specific embodiment of the present invention, nucleic acids include a sequence that encodes a JNK inhibitor peptide, or functional derivatives thereof, are administered to modulate activated JNK signaling pathways by way of gene therapy. In more specific embodiments, a nucleic acid or nucleic acids encoding a JNK inhibitor peptide, or functional derivatives thereof, are administered by way of gene therapy. Gene therapy refers to therapy that is performed by the administration of a specific nucleic acid to a subject. In this embodiment of the present invention, the nucleic acid produces its encoded peptide(s), which then serve to exert a therapeutic effect by modulating function of the disease or disorder. Any of the methodologies relating to gene therapy available within the art may be used in the practice of the present invention. See e.g., Goldspiel, et al., 1993. *Clin Pharm* 12: 488-505.

In a preferred embodiment, the Therapeutic comprises a nucleic acid that is part of an expression vector expressing any one or more of the IB-related peptides, the $JBD_{20}$-related peptides or fragments, derivatives or analogs thereof, within a suitable host. In a specific embodiment, such a nucleic acid possesses a promoter that is operably-linked to coding region(s) of a JNK inhibitor peptide. The promoter may be inducible or constitutive, and, optionally, tissue-specific. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. *Proc Natl Acad Sci USA* 86: 8932-8935.

Delivery of the Therapeutic nucleic acid into a patient may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g., constructing the nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. *J Biol Chem* 262: 4429-4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, e.g., transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth Enzymol* 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g., injection of epithelial cells (e.g., subcutaneously), application of recombinant skin cells as a skin graft onto the patient, and intravenous injection of recombinant blood cells (e.g., hematopoietic stem or progenitor cells). The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973-985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

Immunoassays

The peptides and antibodies of the present invention may be utilized in assays (e.g., immunoassays) to detect, prognose, diagnose, or monitor various conditions, diseases, and disorders characterized by aberrant levels of JNK, or a JNK inhibitor peptide, or monitor the treatment thereof. An "aberrant level" means an increased or decreased level in a sample relative to that present in an analogous sample from an unaffected part of the body, or from a subject not having the disorder. The immunoassay may be performed by a method comprising contacting a sample derived from a patient with an antibody under conditions such that immunospecific-binding may occur, and subsequently detecting or measuring the amount of any immunospecific-binding by the antibody. In a specific embodiment, an antibody specific for a JNK inhibitor peptide may be used to analyze a tissue or serum sample from a patient for the presence of JNK or a JNK inhibitor peptide; wherein an aberrant level of JNK or a JNK inhibitor peptide is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, fluorescent immunoassays, complement-fixation assays, immunoradiometric assays, and protein-A immunoassays, etc.

Kits

The present invention additionally provides kits for diagnostic or therapeutic use that include one or more containers containing an anti-JNK inhibitor peptide antibody and, optionally, a labeled binding partner to the antibody. The label incorporated into the antibody may include, but is not limited to, a chemiluminescent, enzymatic, fluorescent, calorimetric or radioactive moiety. In another specific embodiment, kits for diagnostic use that are comprised of one or more containers containing modified or unmodified nucleic acids that encode, or alternatively, that are the complement to, a JNK inhibitor peptide and, optionally, a labeled binding partner to the nucleic acids, are also provided. In an alternative specific embodiment, the kit may comprise, in one or more containers, a pair of oligonucleotide primers (e.g., each 6-30 nucleotides in length) that are capable of acting as amplification primers for polymerase chain reaction (PCR; see, e.g., Innis, et al., 1990. PCR PROTOCOLS, Academic Press, Inc., San Diego, Calif.), ligase chain reaction, cyclic probe reaction, and the like, or other methods known within the art. The kit may, optionally, further comprise a predetermined amount of a purified JNK inhibitor peptide, or nucleic acids thereof, for use as a diagnostic, standard, or control in the assays.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

SPECIFIC EXAMPLES

Example 1

Identification of JNK Inhibitor Peptides

Amino acid sequences important for efficient interaction with JNK were identified by sequence alignments between known JBDs. Sequence comparison between the JBDs of IB1 [SEQ ID NO:17], IB2 [SEQ ID NO:18], c-Jun [SEQ ID NO:19] and ATF2 [SEQ ID NO:20] defined a weakly conserved 8 amino acid sequence (FIG. 1A). Since the JBDs of IB1 and IB2 are approximately 100 fold as efficient as c-Jun or ATF2 in binding JNK (Dickens et al. *Science* 277: 693 (1997), it was reasoned that conserved residues between IB1 and IB2 must be important to confer maximal binding. The comparison between the JBDs of IB1 and IB2 defined two blocks of seven and three amino acids that are highly conserved between the two sequences. These two blocks are contained within a peptide sequence of 23 amino acids in IB1[SEQ ID NO: 1] and 21 amino acid IB2 [SEQ ID NO:2]. These sequences are shown in FIG. 1B, dashes in the IB2 sequence indicate a gap in the sequence in order to align the conserved residues.

The JNK inhibitor (JNKI) peptides of the present invention were obtained by linking the 20 amino acid JNK-binding motif of JIP-1/IB1, referred to herein as $JBD_{20}$, to a trafficking protein, such as for example, the 10 amino acid $HIV-TAT_{48-57}$ transporter sequence.

Example 2

Preparation of JNK Inhibitor Fusion Proteins

JNK inhibitor fusion proteins were synthesized by covalently linking the C-terminal end of $JBD_{23}$ or the 21 amino acid sequence derived from the JBD of IB2 (JBD$_{21}$) or the C-terminal end of the JBD$_{20}$ amino acid sequence to a N-terminal 10 amino acid long carrier peptide derived from the HIV-TAT$_{48-57}$ (Vives et al., *J. Biol. Chem.* 272: 16010 (1997)) via a spacer consisting of two proline residues. This spacer was used to allow for maximal flexibility and prevent unwanted secondary structural changes. As shown in FIG. 1C, these preparations were designated L-TAT [SEQ ID NO:7], L-TAT-IB1 [SEQ ID NO: 11], L-TAT-IB2 [SEQ ID NO: 12] and L-TAT-JNKI1 [SEQ ID NO:23], respectively. All-D retro-inverso peptides TAT-fusion peptides were also synthesized and were designated D-TAT [SEQ ID NO:8], D-TAT-IB1 [SEQ ID NO:14], and D-TAT-JNKI1 [SEQ ID NO:24] respectively. All D and L peptides were produced by classical F-mock synthesis and further analysed by Mass Spectrometry. They were finally purified by HPLC. To determine the effects of the proline spacer, two types of TAT peptide were produced one with and one without two prolines. The addition of the two prolines did not appear to modify the entry or the localization of the TAT peptide inside cells.

Generic peptides showing the conserved amino acid residues are given in FIG. 2. An "X" indicates any amino acid. The number of Xs in a given peptide is not limited to the one depicted, and may vary (i.e., X can represent any number of amino acid residues, including zero). See above for a more detailed description of the generic sequences.

Example 3

Inhibition of βCell Death By JBD$_{23}$

Effects of the 23 a.a. long JBD sequence of IB1 on JNK biological activities were then studied. The 23 a.a. sequence was linked N-terminal to the Green Fluorescent Protein (GFP-JBD$_{23}$ construct), and the effect of this construct on pancreatic β-cell apoptosis induced by IL-1β was evaluated. See FIG. 3. This mode of apoptosis was previously shown to be blocked by transfection with JBD$_{1-280}$, whereas specific inhibitors of ERK1/2 or p38 did not protect. See Ammendrup et al, *supra*.

Oligonucleotides corresponding to the 23 amino acid sequence (JBD$_{23}$; FIG. 1B) and a sequence mutated at the fully conserved regions (JBD$_{23mut}$) were synthesized and directionally inserted into the EcoRI and SalI sites of the pEGFP-N1 vector encoding the Green Fluorescent Protein (GFP) (from Clontech). Insulin producing βTC-3 cells were cultured in RPMI 1640 medium supplemented with 10% Fetal Calf Serum, 100 μg/mL Streptomycin, 100 units/mL Penicillin and 2 mM Glutamine. Insulin producing βTC-3 cells were transfected with the indicated vectors and IL-1β (10 ng/mL) was added to the cell culture medium. The number of apoptotic cells were counted at 48 hours after the addition of IL-1β using an inverted fluorescence microscope. Apoptotic cells were discriminated from normal cells by the characteristic "blebbing out" of the cytoplasm were counted after two days.

As indicated in FIG. 3, GFP is Green Fluorescent protein expression vector used as a control; JBD23 is the vector expressing a chimeric GFP linked to the 23 a.a. sequence from the JBD of IB1; JBD23Mut is the same vector as GFP-JBD23, but with a JBD mutated at four conserved residues shown as FIG. 1B; and JBD280 is the GFP vector linked to the entire JBD (a.a. 1-280). The GFP-JBD$_{23}$ expressing construct prevented IL-1β induced pancreatic β-cell apoptosis as efficiently as the entire JBD$_{1-280}$ (FIG. 3, JBD23/IL-1 compared to JBD280/IL-1). As additional controls, sequences mutated at fully conserved IB1 residues had greatly decreased ability to prevent apoptosis (FIG. 3, JBD23Mut/IL-1).

Example 4

Cellular Import of TAT-IB1 and TAT-IB2 Peptides

The ability of the L- and D-enantiomeric forms of TAT, TAT-IB1 and TAT-IB2 peptides ("TAT-IB peptides") to enter cells were evaluated.

L-TAT, D-TAT, L-TAT-IB1, L-TAT-IB2 and D-TAT-IB1 peptides [SEQ ID NOs:7, 8, 11, 12 and 14, respectively] were labeled by N-terminal addition of a glycine residue conjugated to fluorescein. Labeled peptides (1 μM) were added to βTC-3 cell cultures, which were maintained as described in Example 3. At predetermined times, cells were washed with PBS and fixed for five minutes in ice-cold methanol-acetone (1:1) before being examined under a fluorescence microscope. Fluorescein-labeled BSA (1 μM, 12 moles/mole BSA) was used as a control. Results demonstrated that all the above fluorescein labeled peptides had efficiently and rapidly (less than five minutes) entered cells once added to the culture medium. Conversely, fluorescein labeled bovine serum albumin (1 μM BSA, 12 moles fluorescein/mole BSA) did not enter the cells.

A time course study indicated that the intensity of the fluorescent signal for the L-enantiomeric peptides decreased by 70% following a 24 hours period. Little to no signal was present at 48 hours. In contrast, D-TAT and D-TAT-IB1 were extremely stable inside the cells. Fluorescent signals from these all-D retro-inverso peptides were still very strong 1 week later, and the signal was only slightly diminish at 2 weeks post treatment.

Example 5

In Vitro Inhibition of c-JUN, ATF2 and Elk1 Phosphorylation

Figure 4A:
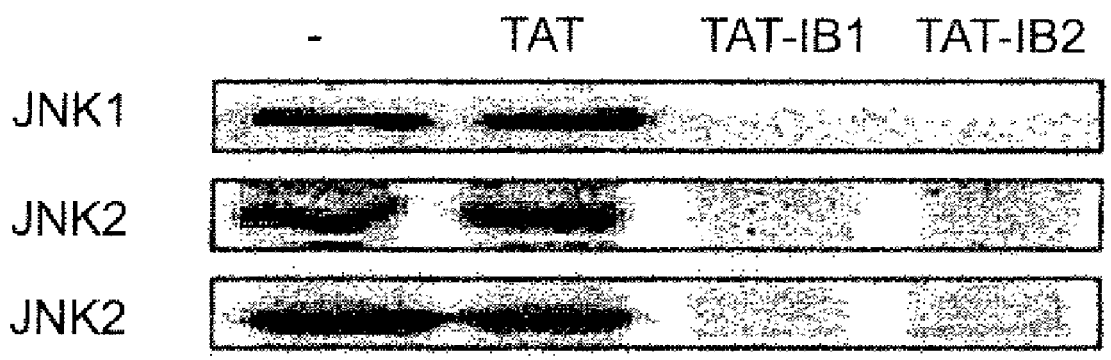
FIG. 4 is an illustration demonstrating the effects of TAT, TAT-IB1 and TAT-IB2 peptides on phosphorylation of recombinant JNKs. Panel A shows inhibition of c-Jun, ATF2 and Elk1 phosphorylation by recombinant JNKs in vitro. Panel B shows dose response experiments similar to Panel A.

The effects of the peptides on JNKs-mediate phosphorylation of their target transcription factors were investigated in vitro. Recombinant and nonactivated JNK1, JNK2 and JNK3 were produced using a TRANSCRIPTION AND TRANSLATION rabbit reticulocyte lysate kit (Promega) and used in solid phase kinase assays with c-Jun, ATF2 and Elk1, either alone or fused to glutathione-S-transferase (GST), as substrates. Dose response studies were performed wherein L-TAT, L-TAT-IB1 or L-TAT-IB2 peptides (0-25 μM) were mixed with the recombinant JNK1, JNK2, or JNK3 kinases in reaction buffer (20 mM Tris-acetate, 1 mM EGTA, 10 mM p-nitrophenyl-phosphate (pNPP), 5 mM sodium pyrophosphate, 10 mM p-glycerophosphate, 1 mM dithiothreitol) for 20 minutes. The kinase reactions were then initiated by the addition of 10 mM MgCl$_2$ and 5 μCi $^{33}$P-γ-dATP and 1 μg of either GST-Jun (a.a. 1-89), GST-AFT2 (a.a. 1-96) or GST-ELK1 (a.a. 307-428). GST-fusion proteins were purchased from Stratagene (La Jolla, Calif.). Ten μL of glutathione-agarose beads were also added to the mixture. Reaction products were then separated by SDS-PAGE on a denaturing 10% polyacrylamide gel. Gels were dried and subsequently exposed to X-ray films (Kodak). Nearly complete inhibition of c-Jun, ATF2 and Elk1 phosphorylation by JNKs was observed at TAT-IB peptide doses as low as 2.5 μM. However, a marked exception was the absence of TAT-IB inhibition of JNK3 phosphorylation of Elk1. Overall, the TAT-IB1 peptide appeared slightly superior to TAT-IB2 in inhibiting JNK family phosphorylation of their target transcription factors. (See, FIG. 4A).

Figure 4B:
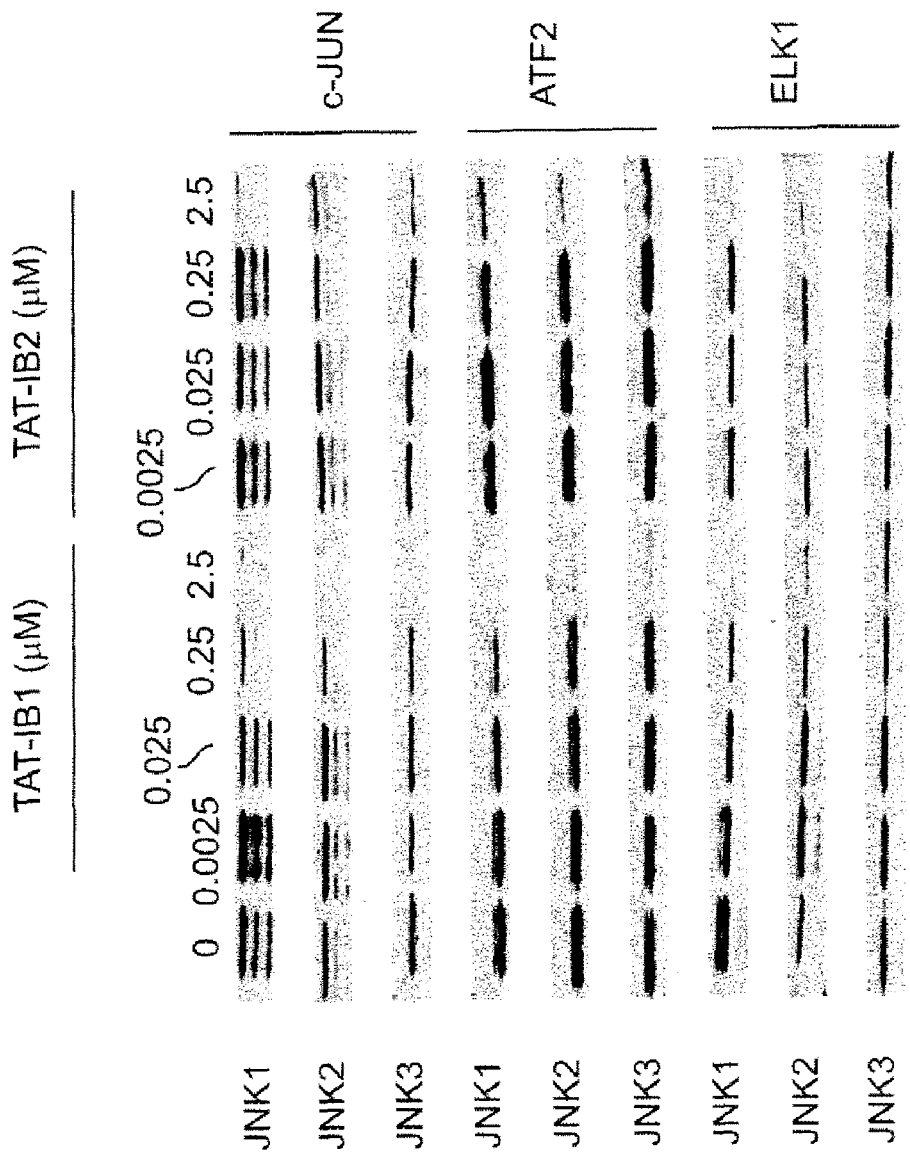

The ability of D-TAT, D-TAT-IB1 and L-TAT-IB1 peptides (0-250 µM dosage study) to inhibit GST-Jun (a.a. 1-73) phosphorylation by recombinant JNK1, JNK2, and JNK3 by were analyzed as described above. Overall, D-TAT-IB1 peptide decreased JNK-mediated phosphorylation of c-Jun, but at levels approximately 10-20 fold less efficiently than L-TAT-IB1. (See, FIG. 4B).

Example 6

Inhibition of c-JUN Phosphorylation by Activated JNKs

Figure 6:
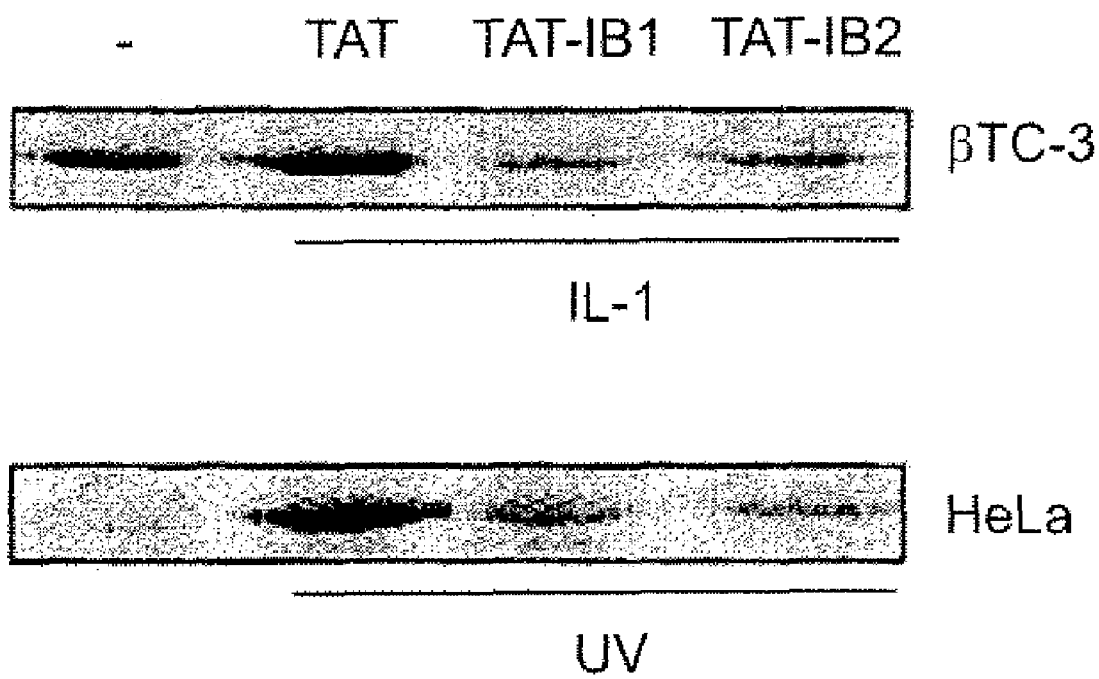
FIG. 6 is an illustration demonstrating the inhibition of c-Jun phosphorylation by activated JNKs.
Figure 7:
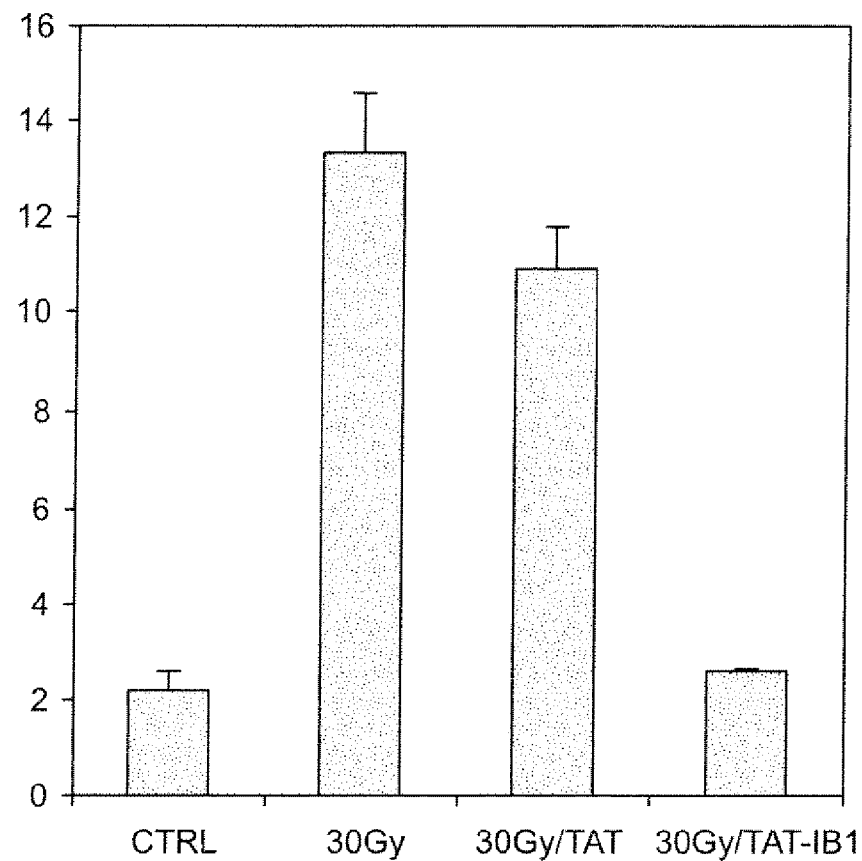
FIG. 7 is a histogram depicting short term inhibition of IL-1β induced pancreatic β-cell death by the L-TAT-IB peptides.
Figure 8:
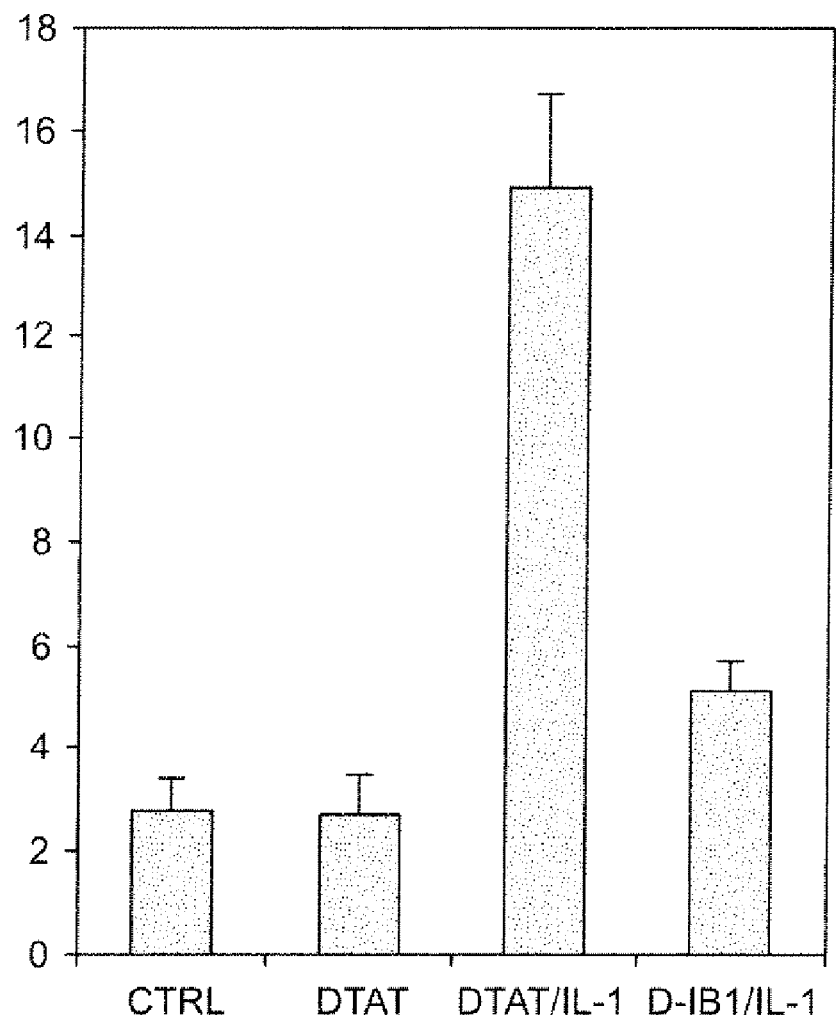
FIG. 8 is a histogram depicting short term inhibition of IL-1β induced pancreatic β-cell death by the D-TAT-IB peptides.

The effects of the L-TAT, L-TAT-IB1 or L-TAT-IB2 peptides on JNKs activated by stressful stimuli were evaluated using GST-Jun to pull down JNKs from UV-light irradiated HeLa cells or IL-1β treated βTC cells. βTC cells were cultured as described above. HeLa cells were cultured in DMEM medium supplemented with 10% Fetal Calf Serum, 100 µg/mL Streptomycin, 100 units/ml Penicillin and 2 mM Glutamine. One hour prior to being used for cell extract preparation, βTC cells were activated with IL-1β as described above, whereas HeLa cells were activated by UV-light (20 J/m$^2$). Cell extracts were prepared from control, UV-light irradiated HeLa cells and IL-1β treated βTC-3 cells by scraping the cell cultures in lysis buffer (20 mM Tris-acetate, 1 mM EGTA, 1% Triton X-100, 10 mM p-nitrophenyl-phosphate, 5 mM sodium pyrophosphate, 10 mM β-glycerophosphate, 1 mM dithiothretiol). Debris was removed by centrifugation for five minutes at 15,000 rpm in an SS-34 Beckman rotor. One-hundred µg extracts were incubated for one hour at room temperature with one µg GST-jun (amino acids 1-89) and 10 µL of glutathione-agarose beads (Sigma). Following four washes with the scraping buffer, the beads were resuspended in the same buffer supplemented with L-TAT, L-TAT-IB1 or L-TAT-IB2 peptides (25 µM) for 20 minutes. Kinase reactions were then initiated by the addition of 10 mM MgCl$_2$ and 5 µCi $^{33}$P-γ-dATP and incubated for 30 minutes at 30° C. Reaction products were then separated by SDS-PAGE on a denaturing 10% polyacrylamide gel. Gels were dried and subsequently exposed to X-ray films (Kodak). The TAT-IB peptides efficiently prevented phosphorylation of c-Jun by activated JNKs in these experiments. (See, FIG. 6).

Example 7

In Vivo Inhibition of c-JUN Phosphorylation by TAT-IB Peptides

To determine whether the cell-permeable peptides could block JNK signaling in vivo, we used a heterologous GAL4 system. HeLa cells, cultured as described above, were co-transfected with the 5×GAL-LUC reporter vector together with the GAL-Jun expression construct (Stratagene) comprising the activation domain of c-Jun (amino acids 1-89) linked to the GAL4 DNA-binding domain. Activation of JNK was achieved by the co-transfection of vectors expressing the directly upstream kinases MKK4 and MKK7 (See, Whitmarsh et al., Science 285: 1573 (1999)). Briefly, 3×10$^5$ cells were transfected with the plasmids in 3.5-cm dishes using DOTAP (Boehringer Mannheim) following instructions from the manufacture. For experiments involving GAL-Jun, 20 ng of the plasmid was transfected with 1 µg of the reporter plasmid pFR-Luc (Stratagene) and 0.5 µg of either MKK4 or MKK7 expressing plasmids. Three hours following transfection, cell media were changed and TAT, TAT-IB1, and TAT-IB2 peptides (1 µM) were added. The luciferase activities were measured 16 hours later using the "Dual Reporter System" from Promega after normalization to protein content. As shown in FIG. 5, addition of both the TAT-IB1 and TAT-IB2 peptides blocked activation of c-Jun following MKK4 and MKK7 mediated activation of JNK. Because HeLa cells express both JNK1 and JNK2 isoforms but not JNK3, we transfected cells with JNK3. Again, the two TAT-IB peptides inhibited JNK2 mediated activation of c-Jun.

Example 8

Inhibition of IL-1β Induced Pancreatic β-Cell Death by TAT-IB Peptides

We investigated the effects of the L-TAT-IB peptides on the promotion of pancreatic β-cell apoptosis elicited by IL-1β. βTC-3 cell cultures were incubated for 30 minutes with 1 µM of either L-TAT-IB1 or L-TAT-IB2 peptides followed by 10 ng/mL of IL-1β. A second addition of peptide (1 µM) was performed 24 hours later. Apoptotic cells were counted after two days of incubation with IL-1β using Propidium Iodide (red stained cell are dead cells) and Hoechst 33342 (blue stained cell are cells with intact plasma membrane) nuclear staining. As shown in FIG. 5, addition of the TAT-IB peptides inhibited IL-1β-induced apoptosis of βTC-3 cells cultured in the presence of IL-1β for two days.

Long term inhibition of IL-1β induced cells death was examined by treating βTC-3 cells as described above, except that incubation of the cells with the peptides and IL-1β was sustained for 12 days. Additional peptides (1 µM) were added each day and additional IL-1β (10 ng/mL) was added every 2 days. The TAT-IB1 peptide confers strong protection against apoptosis in these conditions. Taken together, these experiments establish that TAT-IB peptides are biologically active molecules able to prevent the effects of JNK signaling on cell fate.

Example 9

Synthesis of an all-D-Retro-Inverso Peptides

Peptides of the invention may be all-D amino acid peptides synthesized in reverse to prevent natural proteolysis (i.e., all-D-retro-inverso peptides). An all-D retro-inverso peptide of the invention would provide a peptide with functional properties similar to the native peptide, wherein the side groups of the component amino acids would correspond to the native peptide alignment, but would retain a protease resistant backbone.

Retro-inverso peptides of the invention are analogs synthesized using D-amino acids by attaching the amino acids in a peptide chain such that the sequence of amino acids in the retro-inverso peptide analog is exactly opposite of that in the selected peptide which serves as the model. To illustrate, if the naturally occurring TAT protein (formed of L-amino acids) has the sequence GRKKRRQRRR [SEQ ID NO:7], the retro-inverso peptide analog of this peptide (formed of D-amino acids) would have the sequence RRRQRRKKRG [SEQ ID NO:8]. The procedures for synthesizing a chain of D-amino acids to form the retro-inverso peptides are known in the art. See, e.g., Jameson et al., *Nature,* 368, 744-746 (1994); Brady et al., Nature, 368, 692-693 (1994)); Guichard et al., J. Med. Chem. 39, 2030-2039 (1996). Specifically, the retro-peptides were produced by classical F-mock synthesis and further analysed by Mass Spectrometry. They were finally purified by HPLC.

Since an inherent problem with native peptides is degradation by natural proteases and inherent immunogenicity, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound, both by prolonging half-life and decreasing the extent of the immune response aimed at actively destroying the peptides.

Example 10

Long Term Biological Activity of all-D-Retro-Inverso IB Peptides

Long term biological activity is predicted for the D-TAT-IB retro-inverso containing peptide heteroconjugate when compared to the native L-amino acid analog owing to protection of the D-TAT-IB peptide from degradation by native proteases, as shown in Example 5.

Figure 10:
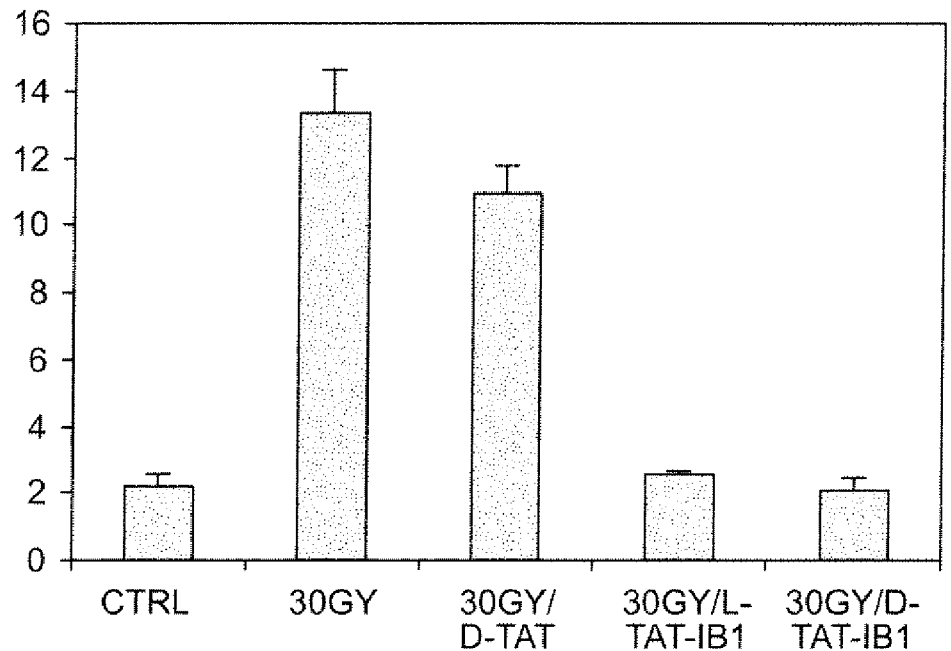
FIG. 10 is a histogram depicting inhibition of irradiation induced human colon cancer WiDr cell death by L-TAT-IB1 and D-TAT-IB1 peptides.

Inhibition of IL-1β induced pancreatic β-cell death by the D-TAT-IB1 peptide was analyzed. As shown in FIG. 10, βTC-3 cells were incubated as described above for 30 minutes with one single addition of the indicated peptides (I μM), then IL-1β (10 ng/ml) was added. Apoptotic cells were then counted after two days of incubation with IL-1β by use of Propidium Iodide and Hoechst 33342 nuclear staining. A minimum of 1,000 cells were counted for each experiment. Standard Error of the Means (SEM) are indicated, n=5. The D-TAT-IB1 peptide decreased IL-1 induced apoptosis to a similar extent as L-TAT-IB peptides (compare FIG. 5 and FIG. 10).

Figure 9:
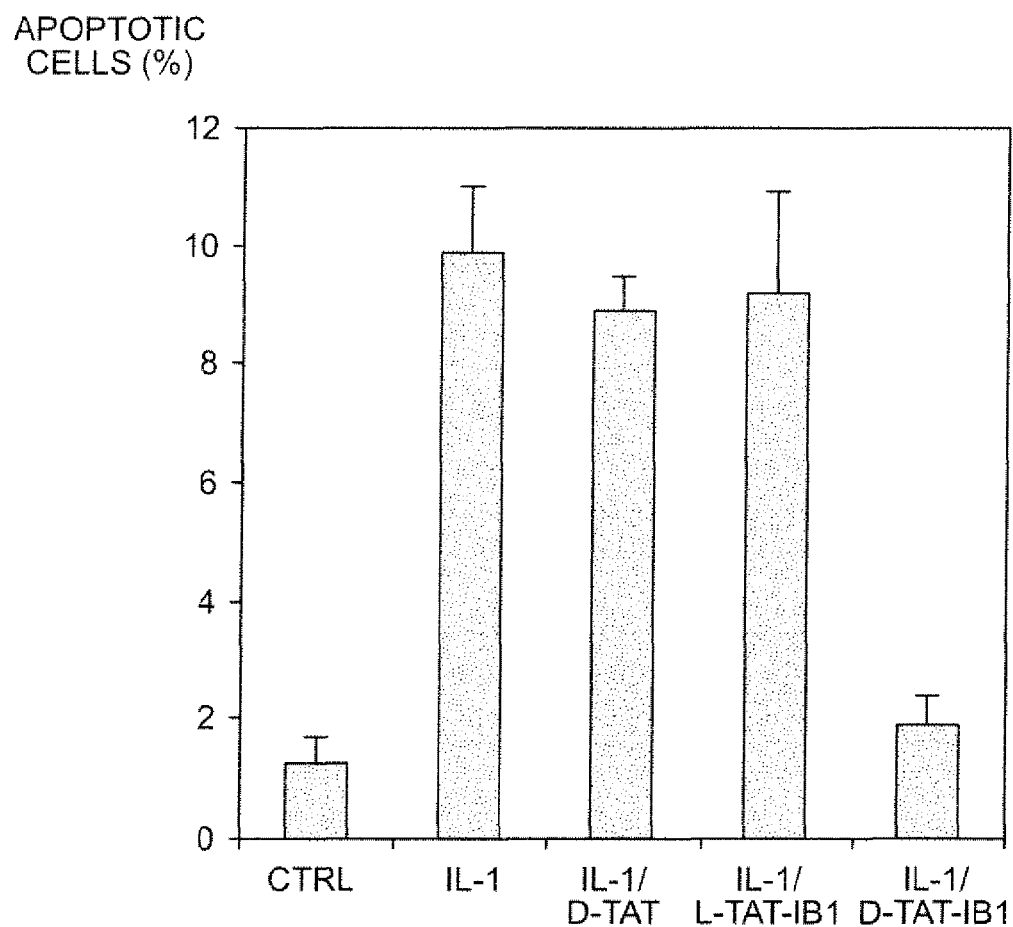
FIG. 9 is a histogram depicting long term inhibition of IL-1β induced pancreatic β-cell death by L-TAT-IB1 and D-TAT-IB1 peptides.

Long term inhibition of IL-1β induced cell-death by the D-TAT-IB1 peptide was also analyzed. βTC-3 cells were incubated as above for 30 minutes with one single addition of the indicated peptides (1 μM), then IL-1β (10 ng/ml) was added, followed by addition of the cytokine every two days. Apoptotic cells were then counted after 15 days of incubation with IL-1β by use of Propidium Iodide and Hoechst 33342 nuclear staining. Note that one single addition of the L-TAT-IB1 peptide does not confer long-term protection. A minimum of 1,000 cells were counted for each experiment. Standard Error of the Means (SEM) are indicated, n=5. Results are shown in FIG. 9. D-TAT-IB1, but not L-TAT-IB1, was able to confer long term (15 day) protection.

Example 11

Inhibition of Irradiation Induced Pancreatic β-Cell Death by TAT-IB Peptides

JNK is also activated by ionizing radiation. To determine whether TAT-IB peptides would provide protection against radiation-induced JNK damage, "WiDr" cells were irradiated (30 Gy) in presence or absence of D-TAT, L-TAT-IB1 or D-TAT-IB1 peptides (1 μM added 30 minutes before irradiation), as indicated in FIG. 10. Control cells (CTRL) were not irradiated. Cells were analyzed 48 hours later by mean of PI and Hoechst 33342 staining, as described above. n=3, SEM are indicated. L-TAT-IB1 and D-TAT-IB1 peptides were both able to prevent irradiation induced apoptosis in this human colon cancer cell line.

Example 12

Radioprotection to Ionizing Radiation by TAT-IB Peptides

To determine the radioprotective effects of the TAT-IB peptides, C57 B1/6 mice (2 to 3 months old) were irradiated with a Phillips RT 250 R-ray at a dose rate of 0.74 Gy/min (17 mA, 0.5 mm Cu filter). Thirty minutes prior to irradiation, the animals were injected i.p. with either the TAT, L-TAT-IB1 and D-TAT-IB1 peptides (30 μl of a 1 mM solution). Briefly, mice were irradiated as follows: mice were placed in small plastic boxes with the head lying outside the box. The animals were placed on their back under the irradiator, and their neck fixed in a small plastic tunnel to maintain their head in a correct position. The body was protected with lead. Prior to irradiation mice were maintained on standard pellet mouse chow, however post irradiation mice were fed with a semi-liquid food that was renewed each day.

The reaction of the lip mucosa was then scored by 2 independent observers according to the scoring system developed by Parkins et al. (Parkins et al, *Radiotherapy & Oncology*, 1: 165-173, 1983), in which the erythema status as well as the presence of edema, desquamation and exudation was quoted. Additionally, animals were weighed before each recording of their erythema/edema status.

Figure 12:
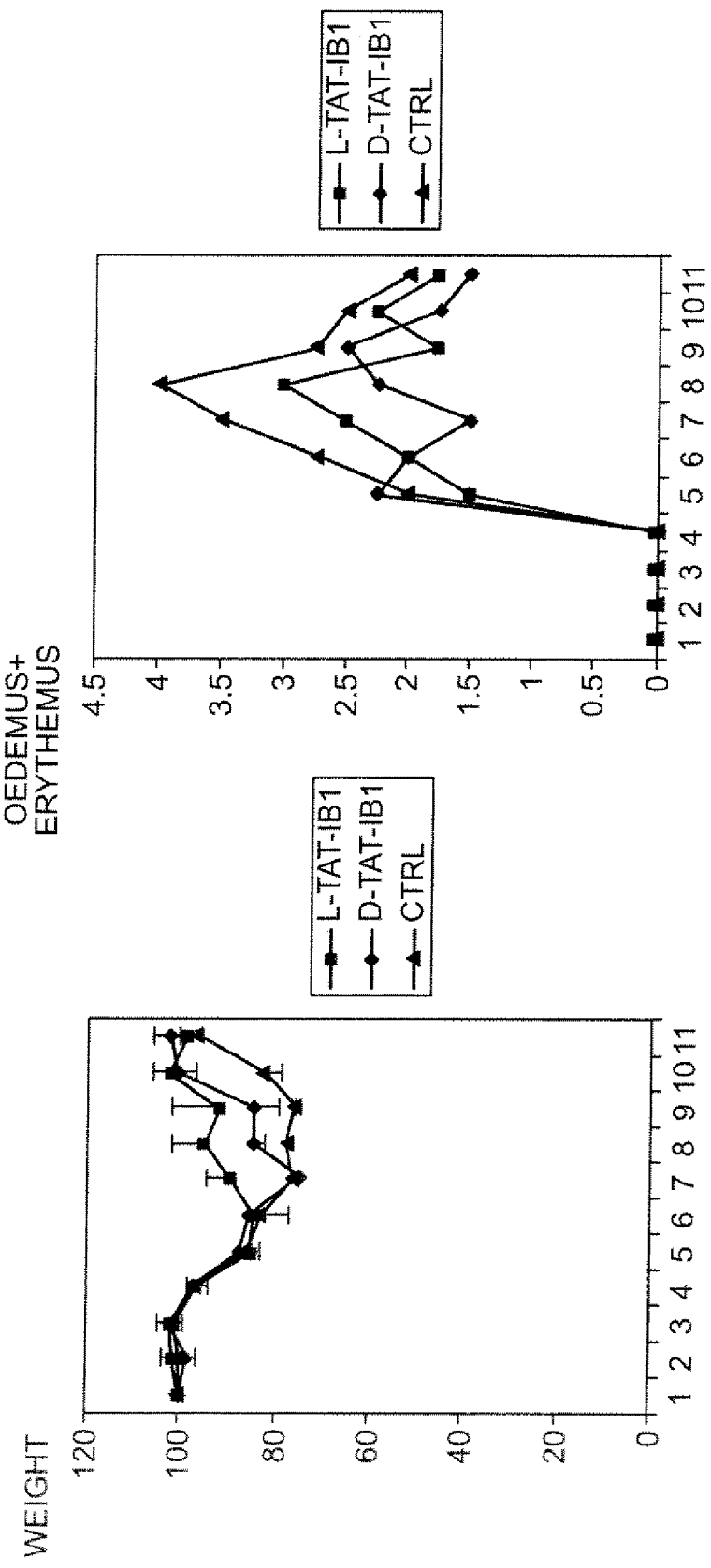
FIG. 12 are graphs depicting the protective effects of the TAT-IB1 peptides in mice. Panel A shows the effect of irradiation on weight. Panel B shows the effect of irradiation on oedemus and erythemus status.

FIG. 12A: illustrated the weight of the mice following irradiation. Values are reported to the initial weight of the mice that was set to 100. CTRL: control mice injected with 30 μl of a saline solution. n=2 for each values reported, S.D. are indicated. x values are days FIG. 12B is illustrative of the erythema/edema scoring following irradiation. The edema and erythema status of the ventral lip of the same mice as in FIG. 12A was quantified. n=2 for each value reported. x values are days The results of these experiments indicate that the TAT-IB Peptides can protect against weight loss and erythema/edema associated with ionizing radiation.

Example 13

Suppression of JNK Transcription Factors by L-TAT-IB1 Peptides

Figure 11:
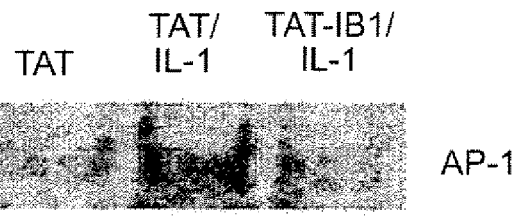
FIG. 11 is an illustration showing the modulation of JNK kinase activity by L-TAT, TAT-IB1 and D-TAT-IB1 peptides.

Gel retardation assays were carried out with an AP-1 doubled labeled probe (5'-CGC TTG ATG AGT CAG CCG GAA-3' (SEQ ID NO:29). HeLa cell nuclear extracts that were treated or not for one hour with 5 ng/ml TNF-α, as indicated. TAT and L-TAT-IB1 peptides were added 30 minutes before TNF-α. Only the part of the gel with the specific AP-1 DNA complex (as demonstrated by competition experiments with non-labeled specific and non-specific competitors) is shown. L-TAT-IB1 peptides decrease the formation of the AP-1 DNA binding complex in the presence of TNF-α. (See, FIG. 11).

Example 14

Protection Against Noise-Induced Hearing Loss by D-TAT-IB Peptides

Figure 13:
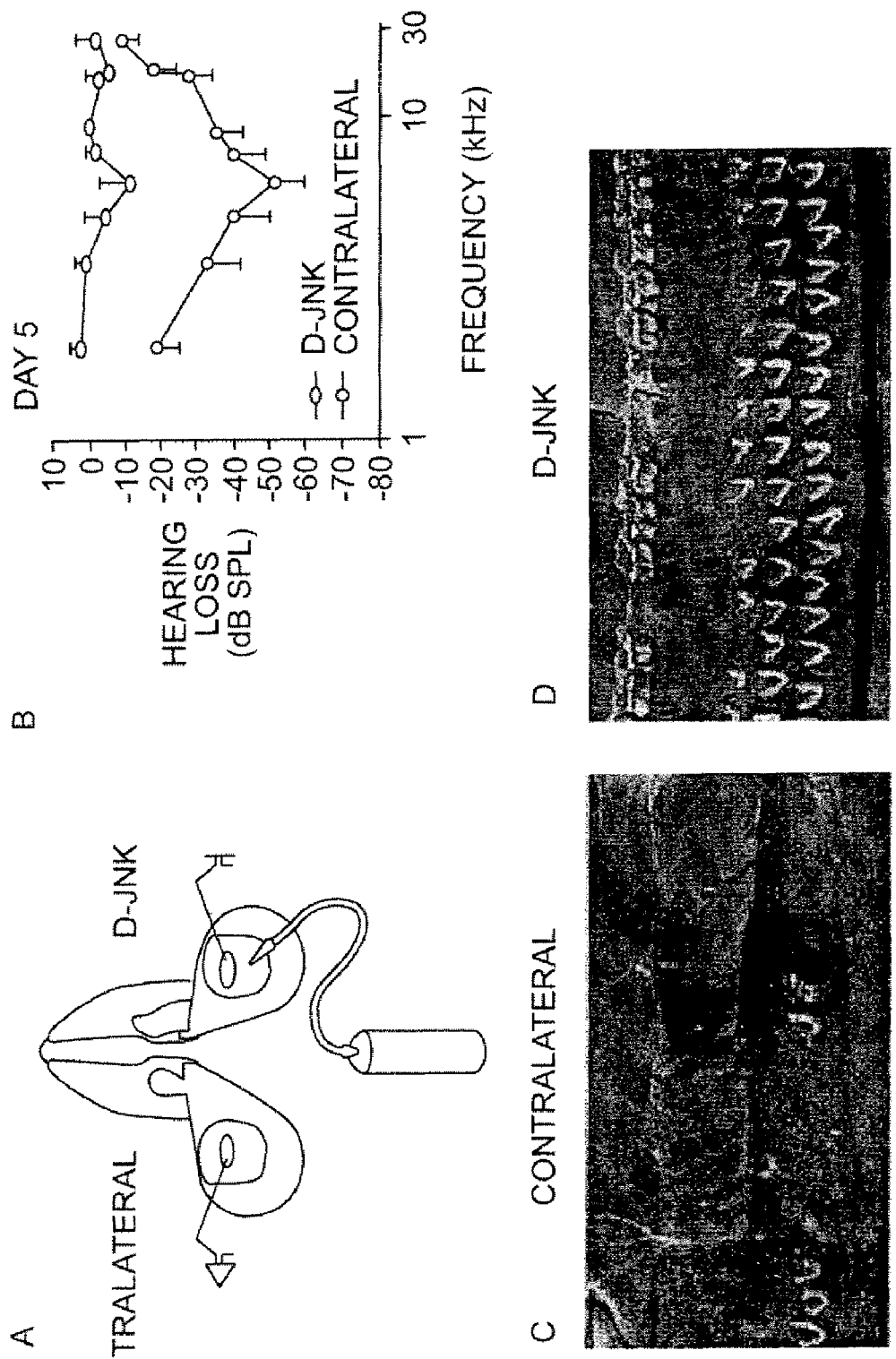
FIG. 13 is a figure depicting the protective effect of D-JNK1 on noise-induced hearing loss. Panel A shows a schematic depiction of the experiment, panel B shows a graph of hearing loss, panels C and D depict histological examination of the contralateral (control) and D-JNK1-injected ear, respectively.

A solution of D-JNKI (1 uM, 1 ul/hr) was injected into the right internal ear of a guinea pig as shown in FIG. 13, panel A, whereas the left ear was injected with saline only. The pig was then exposed to a noise trauma (120 db, 30 minutes), and recording of hearing sensitivity was performed three days after (FIG. 13, panel B) as well as histological examination of the inner ear (FIG. 13, panel C an D). As shown in FIG. 13 the ciliated structures on the JNKI treated ear are completely protected from noise induced destruction as judged from the histological examination, in contrast to the non-treated ear where most of the ciliated structures have disappear. Further-more, the sensitivity of the D-JNK1 treated ear to noise appear to be preserved (FIG. 13, panel B).

Example 15

Protection Against Antibiotic-Induced Hearing Loss by D-TAT-IB Peptides

Figure 14A:
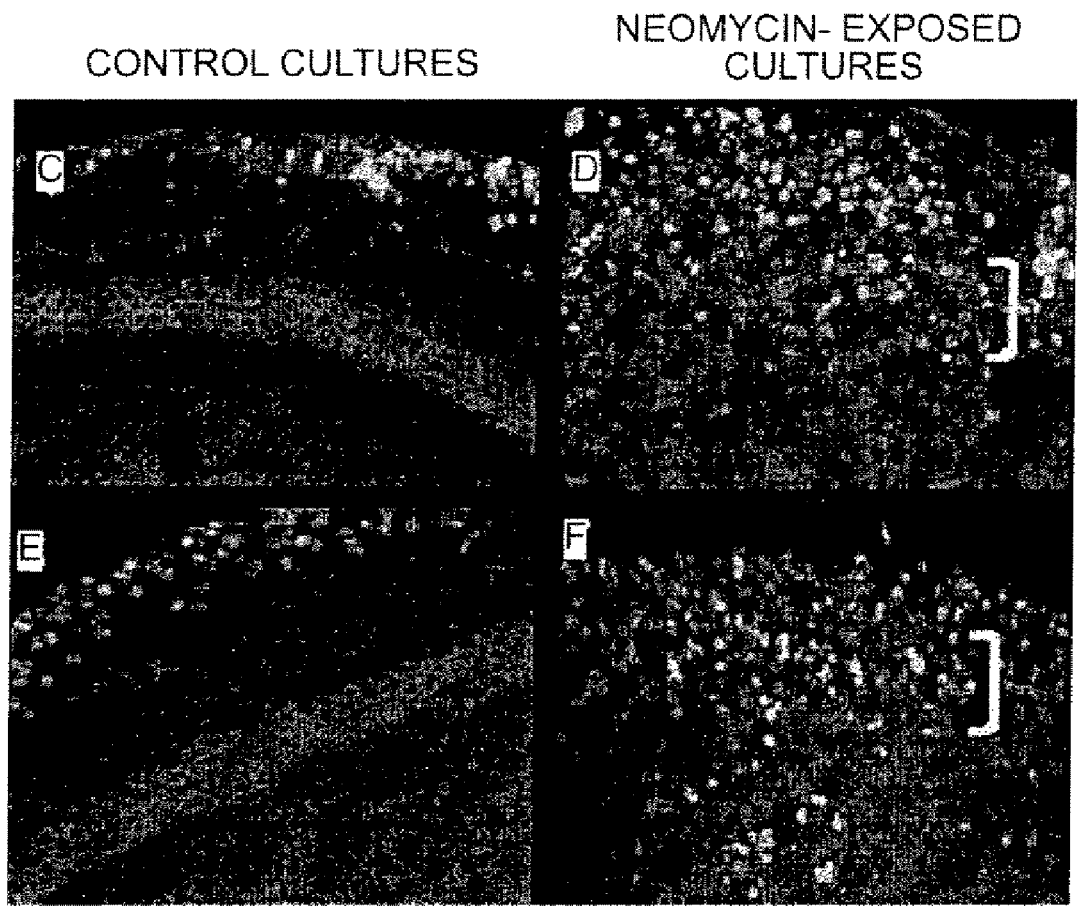
FIGS. 14A and B are figures depicting the protective effect of D-JNK1 on antibiotic-induced hearing loss.

Chicken internal ears were treated with streptomycin in the presence/absence of D_JNKI. TUNELi experiments were then performed to detect apoptosis (green nuclei). As shown in FIG. 14, D-JNKI fully protects internal ears from streptomycin induced apoptosis. Thus D-JNK-I is useful in the prevention of hearing loss conditions sustained by antibiotic therapy.

Example 16

Figure 15:
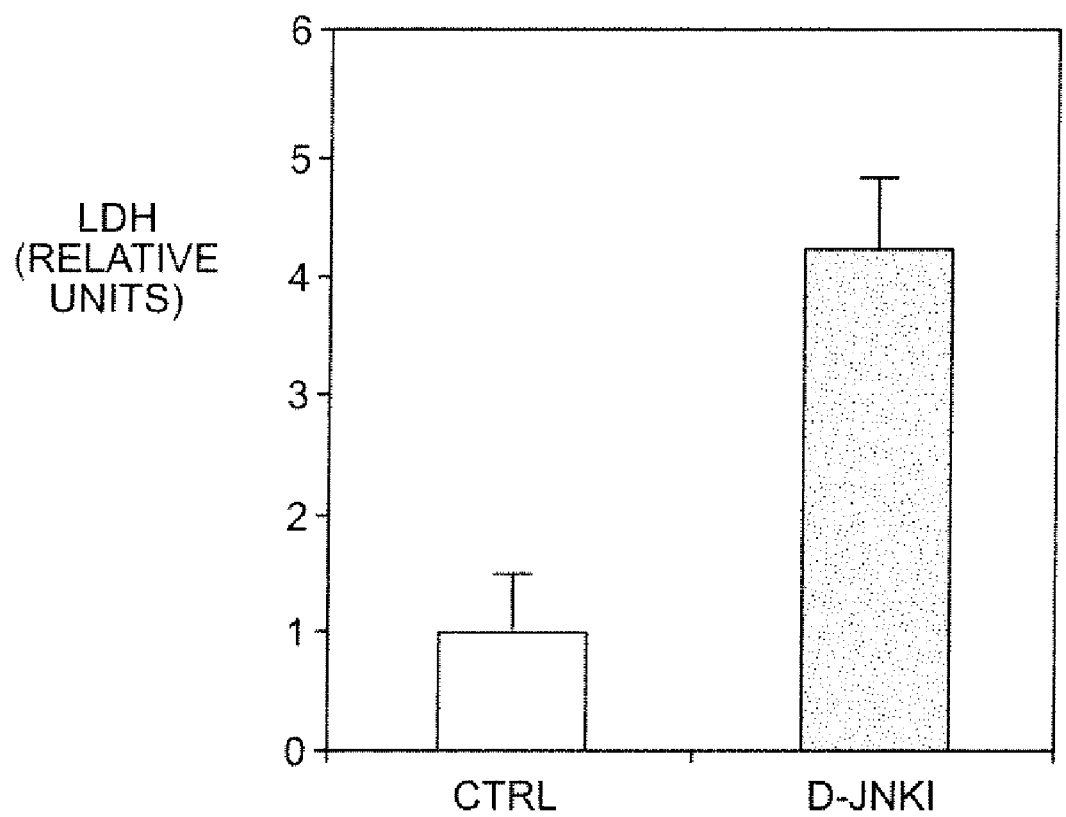
FIG. 15 is a bar graph depicting the increased recovery of pancreatic islets subjected to D-JNK1 treatment during the isolation procedure.

Protection Against Pancreatic Islet Destruction Induced by Pro-Inflammatory Cytokines by D-TAT-IB Peptides Pancreatic islets cells were treated with D-JNK1 (1 mM for one hour before being exposed to interleukin 1B (10 ng/ml). As shown in FIG. 15, D-JNKI treated islets resist IL-1B induced destruction. This indicates that treatment with D-JNKI helps preserve grafted islets.

Example 17

Increase Recovery of Pancreatic Islets Cells by D-TAT-IB Peptides

D-JNK-I were added together with collagenase during islet cell isolation. This resulted in an increased yield of islet after 3 days in culture as measured by the increase in lactate dehydrogenase. See FIG. 15.

Example 18

General Methods Used in Testing the Effects of JNKI Peptides on JNK Activation and JNK-Related Action General Neuronal Culture: Small pieces of cortex from the brains of two day old rat pups were dissected and incubated with 200 units of papain for 30 minutes at 34° C. Then, the neurons were plated at densities of approximately $1 \times 10^6$ cells/plate on dishes that had been pre-coated with 100 µg/mL poly-D-lysine. The cells were cultured using a B27/Neurobasal (Life Technologies) culture medium, supplemented with 0.5 m glutamine, 100 U/mL penicillin and 100 µg/mL streptomycin.

Lactate dehydrogenase (LDH) cytotoxicity assay: The amount of LDH released into the culture medium was measured using the Cytotox 96 non-radioactive cytotoxicity assay kit (Promega).

GST-c-Jun pull-down and kinase assay: Cellular extracts were prepared by scraping cells in lysis buffer (20 mM Tris-acetate, 1 mM EGTA, 1% Triton X-100, 10 mM p-nitrophenyl-phosphate, 5 mM sodium pyrophosphate, 10 mM β-glycerophosphate, 1 mM dithiothreitol). 25 µg samples were incubated for 1 hour at room temperature with 1 µg GST-c-Jun (amino acid residues 1-89) and 10 µL glutathione-agarose beads (Sigma). The beads were washed four times and then resuspended in the lysis buffer described above. In vitro kinase assays were then performed using recombinant JNK1α1 and 0.5 µg of a substrate selected from the group consisting of GST-fusion proteins (e.g., GST-Jun and GST-Elk1 fusion proteins), casein and histone (Sigma). Reactions were initiated with 10 mM $MgCl_2$ and 10 µM ATP in the presence of 5 µCi $^{33}$P-ATP, and were incubated for 30 minutes at 30 degrees Celsius. The reaction products were separated by SDS-PAGE, and the gels were dried and then exposed to X-ray films (Kodak).

Western blots: Total protein extracts were obtained by scraping cells in lysis buffer (described above), separating the proteins on a 12% SDS polyacrylamide gel. The separated proteins were then transferred onto polyvinylidene fluoride (PVDF) membrane. Antibodies used in the Western blots described herein were obtained from Alexis.

Separation of nuclei from cytoplasm: To isolate nuclei for Western blot analysis (see FIG. 17B), neurons were lysed for 15 minutes in lysis buffer, and then the samples were centrifuged at 300 g for 10 minutes at 4° C. The nuclear pellets were reconstituted in lysis buffer and then sonicated.

Real-time RT-PCR: Real-time RT-PCR was performed using specific primers on a lightcycler apparatus (Roche). The housekeeping actin transcript was used to normalize for the amount and quality of the RNAs that were extracted by the Chomczynski method. See Chomczynski et al., *Anal. Biochem.*, 162:156-59 (1987), hereby incorporated by reference in its entirety. The sequences of the primers used were as follows:

| | | |
|---|---|---|
| c-Fos: | Forward: 5'-GCTGACAGATACACTCCAAG-3' | (SEQ ID NO: 30) |
| | Reverse: 5'-CCTAGATGATGCCGGAAACA-3' | (SEQ ID NO: 31) |
| Actin: | Forward: 5'-AACGGCTCCGGCATGTGCAA-3' | (SEQ ID NO: 32) |
| | Reverse: 5'-ATTGTAGAAGGTGTGGTGCCA-5' | (SEQ ID NO: 33 |

P-c-jun immunohistochemistry: P-c-jun, as used herein refers to phosphorylated forms of c-jun. P-c-jun was targeted with a rabbit polyclonal antibody (500x in PBS) (Cell Signaling Technology). The resulting antibody complex was visualized with 3,3-diaminobenzidine as the substrate.

Transient ischemia in adult mice: Using male ICR-CD1 mice (approximately 6 weeks old and weighing in the range of about 18 to 37 g) (Harlan, Inc.), ischemia was provoked by introducing a filament from the common carotid artery into the internal carotid artery and advancing the filament into the arterial circle, thereby occluding the middle cerebral artery. See e.g., Huang et al., *Science*, 265:1883-85 (1994); Hara et al., *Proc. Natl. Acad. Sci.* (*USA*) 94:2007-12 (1997); each of which is hereby incorporated by reference in its entirety. Regional cerebral blood flow was measured by laser-Doppler flowmetry with a probe fixed on the skull throughout the ischemia and until 10 minutes after reperfusion. Rectal temperature was measured and maintained at 37° C. The animals were sacrificed 48 hours after reperfusion. Serial cryostat sections 20 μM-thick were traced using a computer-microscope system equipped with the Neurolucida program (Microbrightfield, Inc.), and the volumes of the ischemic area and of the whole brain were calculated (blind) with the Neuroexplorer program. Systolic and diastolic blood pressure were measured with an arterial catheter in three additional mice from 10 minutes before the D-JNKI1 injection until 30 minutes afterwards. These blood pressure measurements showed that the injections did not affect blood pressure (i.e., less than 10% change). The Guidelines of the Swiss Federal Veterinary Office were followed in all experiments.

Permanent focal ischemia in young (P 14) rats: Middle cerebral artery occlusion was obtained by electrocoagulating the middle cerebral artery at a position closed to its origin at the junction with the olfactory branch. The rats (from Wistar), which weighed in the range of about 27-35 g, were sacrificed 24 hours after middle cerebral artery occlusion. The rats were sacrificed using an overdose of chloral hydrate and were perfused through the left ventricle with Zamboni's fixative. The brains were postfixed for 2 hours in the same solution used for perfusion, and then the brains were infiltrated overnight in 30% sucrose for cryoprotection. The outlines of each ischemic area were drawn on (stained) with a computer-microscope system. The area of the ischemic lesion and of the whole brain were traced from 50 μm serial cryostat sections stained with cresyl violet using the Neurolucida program, and the volumes of each were calculated using the Neuroexplorer program, as described above.

Statistics: Data from both ischemia models (i.e., transient and permanent) were transformed logarithmically to satisfy the Gaussian criterion. Data was analyzed with an overall ANOVA (p<0.0001 for both models) followed by one-tailed unpaired t-tests.

Example 19

Sensitivity and Specificity of JNKI Peptides Against JNK Action

The JNKI 1 peptides used in these experiments are aimed at blocking the access of JNK to c-Jun and other substrates by a direct competitive mechanism. See e.g., Bonny et al., *Diabetes*, 50:77-82 (2001); Barr et al., *J. Biol. Chem.*, 277:10987-97 (2002), each of which is hereby incorporated by reference in its entirety.

Figure 16:
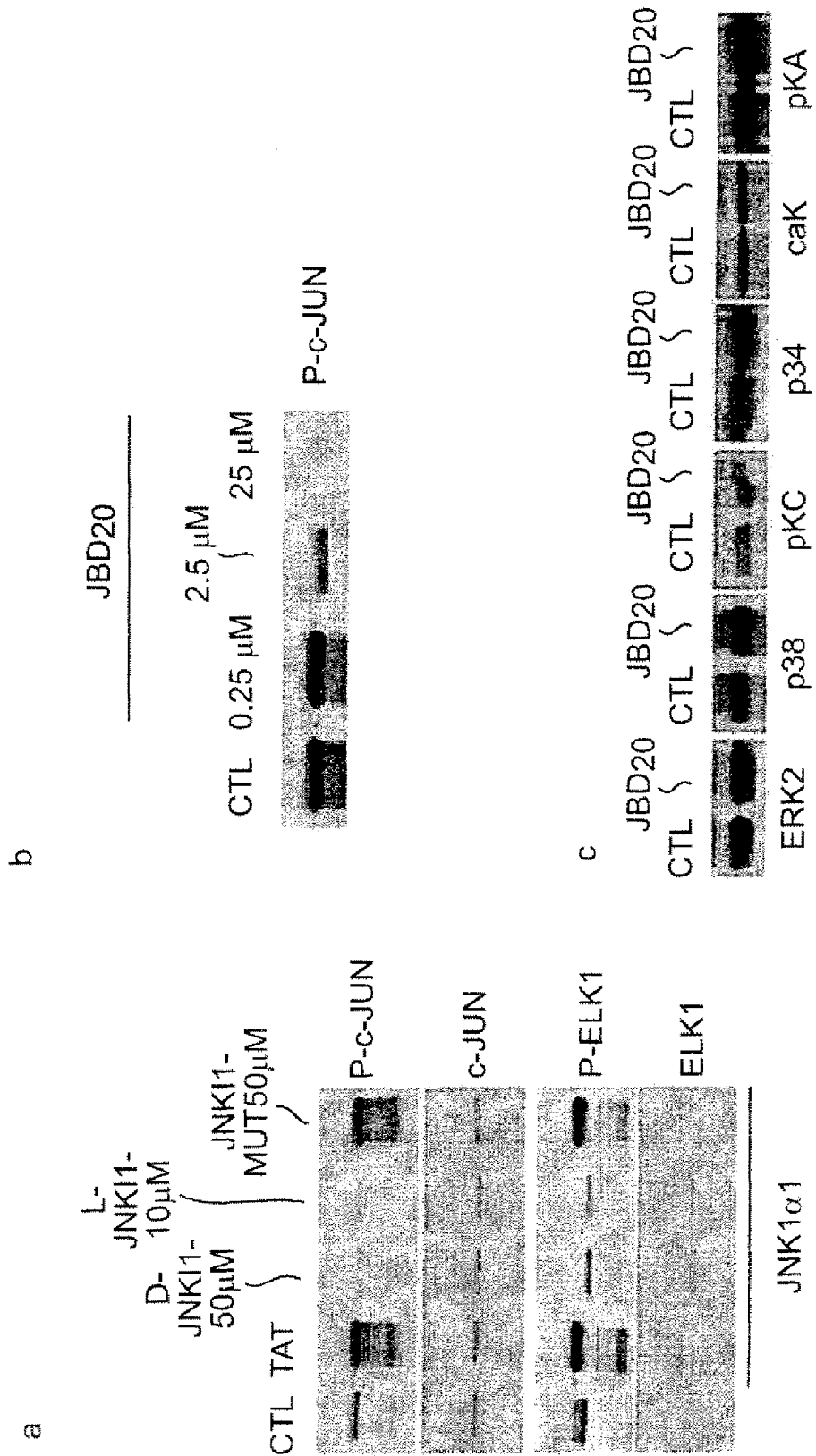
FIG. 16A is an illustration demonstrating the sensitivity and specificity of the JNK-inhibitory (JNKI) peptides of the present invention against JNK activation and action.
FIG. 16B is an illustration demonstrating the sensitivity and specificity of the JNK-inhibitory (JNKI) peptides of the present invention against JNK activation and action.
FIG. 16C is an illustration demonstrating the sensitivity and specificity of the JNK-inhibitory (JNKI) peptides of the present invention against JNK activation and action.

The inhibitory effect of L-JNKI1 and D-JNKI1 on JNK activation and action was tested using the kinase assays, as described above in Example 18. The results of these experiments are shown in FIGS. 16A-16C. The inhibitory effect of L-JNKI1 and D-JNKI1 on JNK activation and action is shown by their ability to prevent the phosphorylation in vitro of known JNK targets c-Jun and Elk1 using JNK1α1. (See FIG. 16A). The terms "P-Jun" and "P-Elk1," as used herein, refer to the radiolabeled (i.e., phosphorylated with $^{33}$P-ATP) forms of GST-Jun and GST-Elk1 substrates, respectively. FIG. 16B demonstrates the inhibitory effect of the 20 amino acid minimal JNK-inhibitory sequence of JIP-IB1 (L-form of $JBD_{20}$ (SEQ ID NO:21)) in dose response experiments, using conditions similar to those used to test the inhibitory effect of L-JNKI1 and D-JNKI1 and using decreasing amounts of L-$JBD_{20}$. FIG. 16B illustrates that the L-$JBD_{20}$ peptide (SEQ ID NO:21) alone (i.e., without the TAT sequence) can inhibit JNK action. $JBD_{20}$ was also shown to inhibit other JNK targets including ATF2, IRS-1, MADD, bcl-xl. In each of these cases, the $IC_{50}$ was about 1 μM (data not shown). The TAT sequence was not linked to $JBD_{20}$ in these experiments, because, at concentration greater than 50 μM, the TAT sequence induces a nonspecific precipitation of the proteins in the extracts. Below 50 μM, TAT does not influence the inhibitory properties of the $JBD_{20}$ peptides.

In vitro experiments were performed to determine the specificity of the JNKI peptides in blocking JNK activation. In particular, the effect of these peptides on the activity of 40 different kinases (10 μM peptides, 10 μM ATP) towards their respective substrates was tested. The complete list of substrates used in these experiments can be found on the world wide web at [[http://]] www.upstate.com/img/pdf/KinaseProfiler.pdf. As expected, the JNKI peptides had an affect on the JNKs and MKK4 and MKK7 kinases, all of which contain JNK-binding domains. The peptides (both the L-JNKI1 and D-JNKI1 forms) completely failed to interfere with the activities of all other kinases. Additional experiments showed that 500 μM of the $JBD_{20}$ peptides did not interfere with the activity of 6 particular kinases: ERK2, p38, pKC, p34, caK and pKA (FIG. 16C). The substrates for these kinases are ERK2:ERK1; p38:ATF2; p34, pKC, pKA:histone; and caK:caseine. This level of specificity is far above those achieved with other small chemical inhibitors of Jun-N-terminal kinase, thereby demonstrating the extremely high selectivity of the JNKI peptides of the invention. For a discussion of other small chemical inhibitors of the Jun N-terminal kinase (JNK), see Bennett et al., *Proc. Natl. Acad. Sci.* (*USA*), 98:13681-86 (2001), hereby incorporated by reference in its entirety.

Example 20

Figure 17:
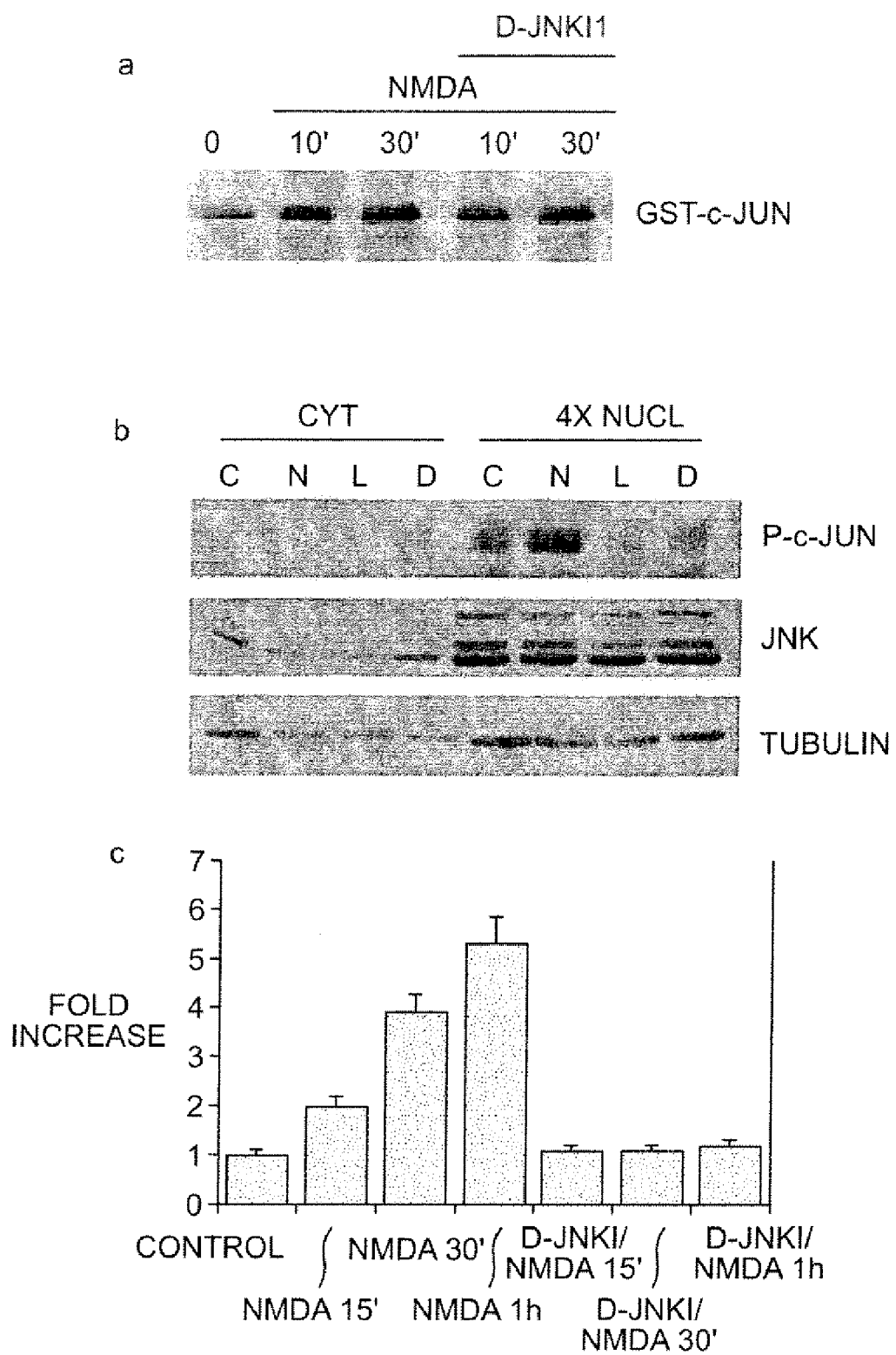
FIG. 17A is an illustration demonstrating N-methyl-D-aspartate ("NMDA")-induced activation of JNK in untreated neurons (0) and in neurons exposed to 100 μM NMDA for 10 minutes (10') or for 30 minutes (30').
FIG. 17B is an illustration that demonstrates the effects of the JNKI peptides of the present invention on the level of c-Jun phosphorylation and the amount of JNK after exposure to NMDA.
FIG. 17C is a histogram that depicts the quantification of c-fos expression by real-time PCR using extracted RNA.
Figure 18:
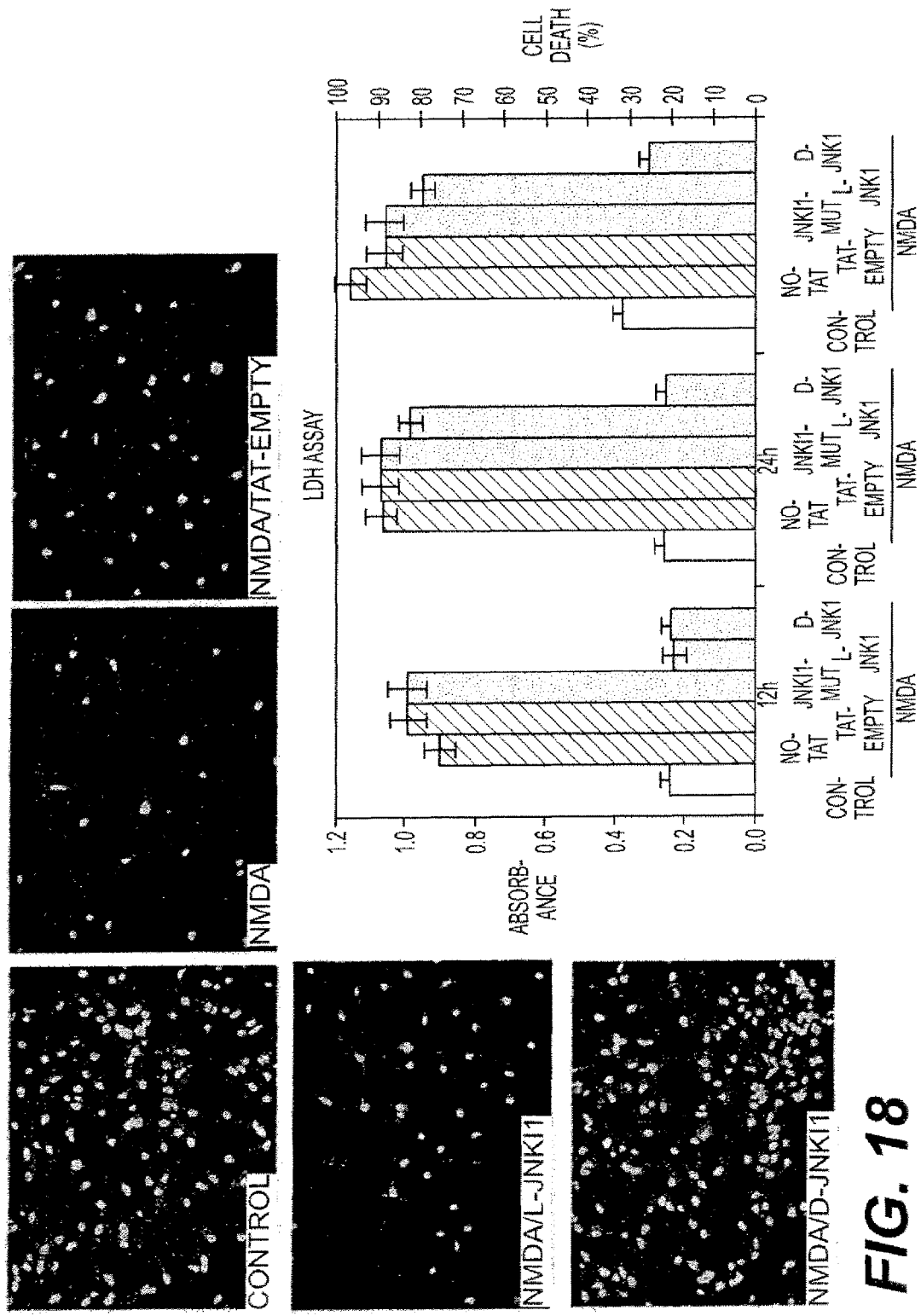
FIG. 18 are illustrations and a histogram depicting the time course of NMDA neurotoxicity and neuroprotection by L-JNKI, D-JNKI and two control peptides, TAT-empty (the TAT sequence alone, without $JBD_{20}$) and L-JNKI 1-mut (wherein 6 amino acids have been mutated to alanine).

Effects of the JNKI Peptides on JNK Targets Inside NMDA-Treated Cortical Neurons A series of experiments were performed to analyze the effects of the JNKI peptides of the invention on different JNK targets inside neurons. The activation of JNK in N-methyl-D-aspartate (NMDA)-treated cortical neurons in culture was estimated by performing kinase assays on pulled-down JNK using GST-c-Jun, using the methods described above. (See e.g., Ko et al., *J. Neurochem.* 71:1390-1395 (1998); Coffey et al., *J. Neurosci.* 20:7602-7613 (2000), each of which is hereby incorporated in its entirety by reference). The results of these experiments are shown in FIGS. 17-18.

FIG. 17A shows the JNK activity in untreated neurons ("0"), after 10 minutes exposure to 100 μM NMDA (10') or after 30 minutes exposure to 100 μM NMDA. The two lanes at the right of FIG. 17C demonstrate that JNK activation was essentially unchanged by D-JNKI1. The increase in JNK activity appeared maximal (i.e., 2.2 fold) after 30 minutes of NMDA treatment (FIG. 17A). This increase in JNK activity translated into an elevated c-Jun phosphorylation (FIG. 17B). Addition of the cell-penetrating peptides L-JNKI1 and D-JNKI1 was shown to completely prevent the increase in P-c-Jun after 5 hours of exposure to 100 μM NMDA, despite a normal level of JNK activation. Addition of L-JNKI1 and D-JNKI1 brought the level of P-c-Jun below even the level of P-c-Jun in the control.

NMDA-induced transcription of the c-fos gene, under the influence of JNK via the Elk1 transcription factor was also completely prevented by the addition of L-JNKI and D-JNKI (FIG. 17C). c-fos expression was quantitated by real-time PCR (Lightcycler) using RNA extracted using the methods described above in Example 18. The data in FIG. 17C is presented as c-fos expression relative to actin (n=4). For a description of the induction of c-fos expression through JNK-mediated TCF/Elk-1 phosphorylation, see Cavigelli et al., *EMBO J.*, 14:5957-5964 (1995), hereby incorporated by reference in its entirety.

The time course of NMDA neurotoxicity and neuroprotection by L-JNKI1 and D-JNKI1 as well as two control peptides, TAT-empty (i.e., the TAT sequence alone, without the $JBD_{20}$ sequence) and L-JNKI1 $_{mut}$ (having six amino acids mutated to alanine, as described in Bonny et al., *Diabetes* 50:77-82 (2001), hereby incorporated by reference in its entirety). The micrographs of FIG. 18 show Hoechst-stained neurons at 24 hours after treatment. Addition of the L-JNKI1 and D-JNKI1 peptides completely protected neurons against the excitotoxic effects of NMDA (FIG. 18) or kainate (data not shown), while the addition of control peptides had no neuroprotective effect. At 12 hours post-treatment, both L-JNKI1 and D-JNKI1 peptides were shown to inhibit neuronal death whereas TAT-empty peptides had no effect (FIG. 18).

As seen in FIG. 18, the D-form of the cell-penetrating peptides of the invention, i.e., D-JNKI1, was superior in protecting neurons for extended periods of time, i.e., 12 hours, 24 hours and 48 hours post-exposure to 100 μM NMDA. These micrographs indicate that at 24 hours post-treatment, D-JNKI1 still gave total neuroprotection, as the control cultures and the cultures treating with D-JNKI1 and NMDA were comparable. The L-form of JNKI1 no longer protected the neurons at 24 hours post-treatment, presumably because the L-forms of peptides are generally more susceptible to degradation. The TAT-empty peptides did not affect cell death in any conditions. The histogram in FIG. 18 depicts the level of neuronal death at 12, 24 and 48 hours after exposure to 100 μM NMDA, as indicated by LDH activity in the medium of the Petri dish. Absorbance values, which represent the LDH concentration, have been converted into % neuronal death values by dividing the absorbance values by the average absorbance for total LDH. The average absorbance for total LDH was obtained from the medium plus lysed neurons.

Example 21

In Vivo Delivery of Cell-Permeable JNKI Peptides

To test the feasibility of using the cell-permeable peptides in in vivo applications, their ability to penetrate into the brain was evaluated using FITC-labeled L-JNKI1 and D-JNKI1. For a discussion on the in vivo delivery of a biologically active protein into a mouse, see Schwarze et al., *Science*, 285:1569-72 (1999), hereby incorporated by reference in its entirety. These experiments showed that both FITC-labeled L-JNKI1 and D-JNKI1 were able to cross the blood-brain barrier and penetrate into the neurons of adult mice and rats of various ages. Both FITC-labeled L-JNKI1 and D-JNKI1 were able to penetrate into the neurons within 1 hour of intraperitoneal injection (data not shown).

Example 22

Neuroprotection by the JNKI Peptides Against Transient and Permanent Focal Cerebral Ischemia In a model of mild ischemia in mice, the left middle cerebral artery was occluded for 30 minutes, followed by 48 h of reperfusion. The control vehicle-treated group received an injection of phosphate buffer saline (PBS) only. In the control vehicle-treated group, this occlusion resulted systematically in a major infarction containing severely pyknotic cells, which were predominantly found in the cortex and the stratum in all brains, and in 7 of the brains, these cells were also found in the hippocampus. The mean infarction volume was 67.4 $mm^3$ (n=12) in those subjects in the control vehicle-treated group.

To evaluation the efficacy and "therapeutic window" of treatment (i.e., the timeframe following injury during which treatment with the peptides of the invention remains effective), subjects were treated with intracerebro-ventricular (icv) injection of D-JNKI1 (15.7 ng in 2 μL of PBS). FIG. 19A demonstrates cresyl violet-stained sections that show typical examples of the resulting infarct (bar, 1 mm). FIG. 19B depicts infarction volumes following icv injection of D-JNKI1 at different times before (−1 hour) or after (+3, 6, or 12 hours) after middle cerebral artery occlusion. In FIG. 19B, an asterisk (*) indicates the result is statistically different from the control (as indicated by a t-test).

Pretreatment 1 hour before middle cerebral artery occlusion with the icv injection of D-JNKI1 significantly decreased the infarct volume measured 48 hours after reperfusion by 88%, to a volume of 7.8 $mm^3$. (FIG. 19A-19B). Administering the D-JNKI1 peptide 3 or 6 hours after middle cerebral artery occlusion was still potently protective, as the mean infarct volume for subjects injected 3 hours post-occlusion was reduced to 5.8 $mm^3$ (a reduction of 91% compared to untreated animals), and the mean infarct volume for subjects injected 6 hours post-occlusion was reduced to 4.8 $mm^3$ (a reduction of 93% compared to untreated animals). In contrast, D-JNKI1 peptide injection at 12 hours after middle cerebral artery occlusion was not significantly protective. To confirm the achievement of complete ischemia followed by reperfusion was confirmed in all animals by monitoring regional cerebral blood flow in the territory of the left middle cerebral artery.

Figure 20:
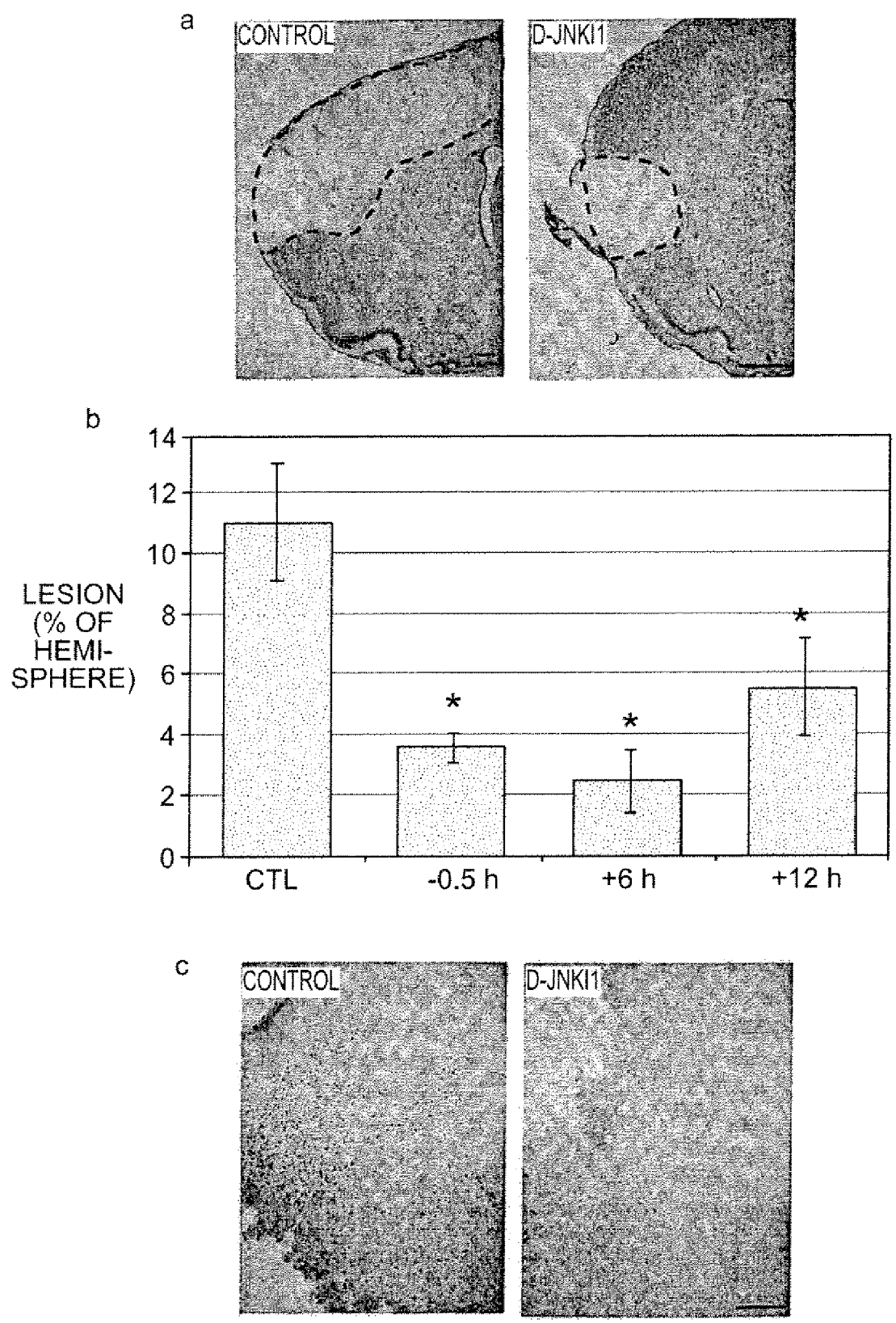
FIG. 20 are illustrations and a histogram demonstrating protection by D-JNKI against permanent focal ischemia in young rats (P 14) that had been perfused 24 hours post-occlusion.

The protective abilities of D-JNKI1 against permanent focal ischemia in young (P14) rats was also evaluated. An ischemic zone in the cerebral cortex of P14 rats by performing a permanent occlusion of the middle cerebral artery, thereby inducing a zone of massive degeneration restricted to the parietotemporal cortex. As brain volumes in the P14 rats were variable, the lesions were expressed as a percentage of the volume of the cerebral hemisphere. D-JNKI1 was injected intraperitoneally at a concentration of 11 mg/kg, which corresponds to approximately 340 μg. D-JNKI1 was administered 30 minutes prior to middle cerebral artery occlusion, or 6 or 12 hours post-occlusion. The rats were fixed at 24 hours post-occlusion. At each of these time-points (i.e., administration at −30 minutes, +6 h or +12 h), D-JNKI1 caused major and statistically significant decreases in the infarct volume, as compared to control animals (FIGS. 20A-20B). Administration of D-JNKI1 30 minutes prior to occlusion led to a decrease in the infarct volume of 68%, while peptide administration at 6 and 12 hours post-occlusion led to decreases in infarct volume of 78% and 49%, respectively.

Immunohistochemistry analysis was performed to determine the activation of the c-Jun transcription factor, a major target of JNK, in the brains of rat pups with permanent ischemia. Phosphorylation of c-Jun was evident in many neurons in the peri-infarcted cortex (FIG. 5C, bar=200 μM). In contrast, in brains treated with D-JNKI1 peptide, the peri-infarcted cortex was negative, and only a few positive neurons at the border of the infarcted region were detected.

Example 22

Behavioral Evaluation of Potential Side-Effects of JNKI Peptides

Typically, the high toxicity of other neuroprotective compounds has severely limited their clinical use. (See Gladstone et al., *Stroke*, 33:2123-36 (2002), incorporated by reference in its entirety). The ability of mice to maintain themselves on horizontal turning rotarod was used as criterion for possible side effects of different doses of D-JNKI1 and of a therapeutic dose of MK-801 (1 mg/Kg, a standard therapeutic dose). In particular, the motor function of the mice was evaluated using the rotarod test at 3 h, 24 h, 6 days and 12 days after both i.p. (11 and 110 mg/Kg) and icv injections of D-JNKI1 (2 μl containing 15.7 ng or 157 ng of D-JNKI1). The i.p. injection of MK-801 (1 mg/Kg) was used as a control compound during this assessment procedure.

The mice were trained the day before and in the morning of the experimental day, in order to reduce the variability between subjects. Both training and test sessions were identical for control and injected mice. The motor function of each mouse was examined immediately before the injection and at 1, 6 and 12 days after the injection. The mice were placed on the rotarod, which was programmed to accelerate uniformly from 4 to 40 rpm. The latency to falls for each mouse tested was recorded. The results of this assessment using the rotarod method are presented in Table 2 as median latency to fall (measured in seconds).

TABLE 2

EFFECT OF D-JNKI1 ON MOTOR COORDINATION

| | | Median latency to fall (secs) | | | | |
|---|---|---|---|---|---|---|
| | DOSE | −1 h | +3 h | 1 day | 6 days | 12 days |
| PBS | 2 μl icv | 234 | 202 | 238 | 268 | 246 |
| MK-801 | 1 mg/Kg i.p. | 226 | incapable | 174 | 233 | 292 |
| D-JNKI1 | 11 mg/Kg i.p. | 204 | 221 | 372 | 287 | 418 |
| | 110 mg/Kg i.p. | 276 | 266 | 447 | 416 | 325 |
| | 15.7 ng icv | 210 | 342 | 302 | 345 | 285 |
| | 157 ng icv | 260 | 200 | 253 | 338 | 335 |
| | 2 μl PBS icv | 234 | 202 | 238 | 268 | 246 |

As seen in Table 2, motor coordination was found to be unimpaired with both the i.p. and icv D-JNKI1 doses (i.e., both the dose, 2.8 μl/Kg, that conferred 90% neuroprotection, and a 10-fold higher dose). In contrast, MK-801 led to a dramatic impairment of motor coordination, as the mice were unable to stand on the rotor wheel. (See e.g., Table 2; Dawson et al., *Brain Res.* 892:344:350 (2001) (describing similar results for other neuroprotectants), and a 10-fold higher dose of MK-801 killed all the mice. The side effects of the lower dose of MK-801 were found to essentially disappear after 24 hours. At 6 and 15 days following treatment with D-JNKI1, no sign of motor impairment was found, and the rotarod scores were reproducibly better than in the control mice.

EQUIVALENTS

From the foregoing detailed description of the specific embodiments of the invention, it should be apparent that unique cell-permeable bioactive peptides have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. A method of treating or reducing the likelihood of hearing loss in a subject, the method comprising administering to the subject a peptide consisting of an amino acid sequence at least 95% identical to an amino acid sequence selected from a group consisting of amino acid sequences of SEQ ID NO:23, the amino acid sequence of TDQSRPVQPFLNLTTFPRKPR in which all of the amino acids are in the D configuration, and the amino acid sequence of TDQSRPVQPFLNLTTFPRKPRPPRRRQRRKKRG in which all of the amino acids are in the D configuration, wherein the peptide directly inhibits at least one c-Jun amino terminal kinase (JNK) protein.

2. The method of claim 1, wherein the peptide consists of an amino acid sequence selected from a group consisting of amino acid sequences of SEQ ID NO:23, the amino acid sequence of TDQSRPVQPFLNLTTFPRKPR in which all of the amino acids are in the D configuration, or the amino acid sequence of TDQSRPVQPFLNLTTFPRKPRPPRRRQRRKK RG in which all of the amino acids are in the D configuration.

3. The method of claim 1, wherein the peptide is administered to the subject before the subject is exposed to a noise trauma.

4. The method of claim 1, wherein the peptide is administered to the subject after the subject is exposed to a noise trauma.

5. The method of claim 3 or 4, wherein the noise trauma is a noise of at least about 90 dB SPL.

6. The method of claim 1, wherein the peptide is administered to the subject before the subject is exposed to an antibiotic.

7. The method of claim 1, wherein the peptide is administered to the subject after the subject is exposed to an antibiotic.

8. The method of claim 6 or 7, wherein the antibiotic is an aminoglycoside.

9. The method of claim 1, wherein the peptide is administered to the subject before the subject is exposed to a chemotherapeutic agent.

10. The method of claim 1, wherein the peptide is administered to the subject after the subject is exposed to a chemotherapeutic agent.

11. The method of claim 1, wherein the peptide is administered to the subject by any administration route selected from a group consisting of intrauricular; intraperitoneal, nasal, intravenous, oral and patch delivery.

12. The method of claim 1, wherein the peptide consists of an amino acid sequence at least 95% identical to the amino acid sequence of TDQSRPVQPFLNLTTPRKPRPPRRR QRRKKRG in which all of the amino acids are in the D configuration.

13. The method of claim 12, wherein the peptide is administered to the subject before the subject is exposed to a noise trauma.

14. The method of claim 12, wherein the peptide is administered to the subject after the subject is exposed to a noise trauma.

15. The method of claim 13 or 14, wherein the noise trauma is a noise of at least about 90 dB SPL.

16. The method of claim 12, wherein the peptide is administered to the subject before the subject is exposed to an antibiotic.

17. The method of claim 12, wherein the peptide is administered to the subject after the subject is exposed to an antibiotic.

18. The method of claim 16 or 17, wherein the antibiotic is an aminoglycoside.

19. The method of claim 12, wherein the peptide is administered to the subject before the subject is exposed to a chemotherapeutic agent.

20. The method of claim 12, wherein the peptide is administered to the subject after the subject is exposed to a chemotherapeutic agent.

21. The method of claim 12, wherein the peptide is administered to the subject by any administration route selected from a group consisting of intrauricular; intraperitoneal, nasal, intravenous, oral and patch delivery.

* * * * *

UNITED STATES PATENT AND TRADEMARK OFFICE
CERTIFICATE OF CORRECTION

| | |
|---|---|
| PATENT NO. | : 8,236,924 B2 |
| APPLICATION NO. | : 12/101911 |
| DATED | : August 7, 2012 |
| INVENTOR(S) | : Christophe Bonny |

It is certified that error appears in the above-identified patent and that said Letters Patent is hereby corrected as shown below:

At column 49, lines 40-41, delete "the amino acid sequence of TDQSRPVQPFLNLTTFPRKPR" and insert --the amino acid sequence of TDQSRPVQPFLNLTTPRKPR--.

At column 49, lines 42-43, delete "the amino acid sequence of TDQSRPVQPFLNLTTFPRKPRPPRRRQRRKKRG" and insert --the amino acid sequence of TDQSRPVQPFLNLTTPRKPRPPRRRQRRKKRG--.

Signed and Sealed this
Thirtieth Day of October, 2012

David J. Kappos
*Director of the United States Patent and Trademark Office*

SEQUENCE LISTING

<160> NUMBER OF SEQ ID NOS: 33

<210> SEQ ID NO 1
<211> LENGTH: 23
<212> TYPE: PRT
<213> ORGANISM: Artificial sequence
<220> FEATURE:
<223> OTHER INFORMATION: Chemically synthesized

<400> SEQUENCE: 1

Asp Thr Tyr Arg Pro Lys Arg Pro Thr Thr Leu Asn Leu Phe Pro Gln
1               5                   10                  15

```
Val Pro Arg Ser Gln Asp Thr
            20

<210> SEQ ID NO 2
<211> LENGTH: 21
<212> TYPE: PRT
<213> ORGANISM: Artificial sequence
<220> FEATURE:
<223> OTHER INFORMATION: Chemically synthesized

<400> SEQUENCE: 2

Glu Glu Pro His Lys His Arg Pro Thr Thr Leu Arg Leu Thr Thr Leu
1               5                   10                  15

Gly Ala Gln Asp Ser
            20

<210> SEQ ID NO 3

<400> SEQUENCE: 3

000

<210> SEQ ID NO 4

<400> SEQUENCE: 4

000

<210> SEQ ID NO 5
<211> LENGTH: 17
<212> TYPE: PRT
<213> ORGANISM: Artificial sequence
<220> FEATURE:
<223> OTHER INFORMATION: Description of Artificial Sequence: JNK
      Inhibitor Peptide
<220> FEATURE:
<221> NAME/KEY: MISC_FEATURE
<222> LOCATION: (6)..(6)
<223> OTHER INFORMATION: Wherein Xaa is any amino acid.
<220> FEATURE:
<221> NAME/KEY: MISC_FEATURE
<222> LOCATION: (8)..(14)
<223> OTHER INFORMATION: Wherein Xaa is any amino acid.
<220> FEATURE:
<221> NAME/KEY: MISC_FEATURE
<222> LOCATION: (17)..(17)
<223> OTHER INFORMATION: Wherein Xaa is Ser or Thr.

<400> SEQUENCE: 5

Arg Pro Thr Thr Leu Xaa Leu Xaa Xaa Xaa Xaa Xaa Xaa Xaa Gln Asp
1               5                   10                  15

Xaa

<210> SEQ ID NO 6

<400> SEQUENCE: 6

000

<210> SEQ ID NO 7
<211> LENGTH: 10
<212> TYPE: PRT
<213> ORGANISM: Artificial sequence
<220> FEATURE:
<223> OTHER INFORMATION: Chemically synthesized

<400> SEQUENCE: 7

Gly Arg Lys Lys Arg Arg Gln Arg Arg Arg
1               5                   10
```

<210> SEQ ID NO 8

<400> SEQUENCE: 8

000

<210> SEQ ID NO 9
<211> LENGTH: 9
<212> TYPE: PRT
<213> ORGANISM: Artificial sequence
<220> FEATURE:
<223> OTHER INFORMATION: Chemically synthesized

<400> SEQUENCE: 9

Arg Lys Lys Arg Arg Gln Arg Arg Arg
1               5

<210> SEQ ID NO 10

<400> SEQUENCE: 10

000

<210> SEQ ID NO 11
<211> LENGTH: 35
<212> TYPE: PRT
<213> ORGANISM: Artificial sequence
<220> FEATURE:
<223> OTHER INFORMATION: Chemically synthesized

<400> SEQUENCE: 11

Gly Arg Lys Lys Arg Arg Gln Arg Arg Arg Pro Pro Asp Thr Tyr Arg
1               5                   10                  15

Pro Lys Arg Pro Thr Thr Leu Asn Leu Phe Pro Gln Val Pro Arg Ser
            20                  25                  30

Gln Asp Thr
        35

<210> SEQ ID NO 12
<211> LENGTH: 33
<212> TYPE: PRT
<213> ORGANISM: Artificial sequence
<220> FEATURE:
<223> OTHER INFORMATION: Chemically synthesized

<400> SEQUENCE: 12

Gly Arg Lys Lys Arg Arg Gln Arg Arg Arg Pro Pro Glu Glu Pro His
1               5                   10                  15

Lys His Arg Pro Thr Thr Leu Arg Leu Thr Thr Leu Gly Ala Gln Asp
            20                  25                  30

Ser

<210> SEQ ID NO 13
<211> LENGTH: 34
<212> TYPE: PRT
<213> ORGANISM: Artificial sequence
<220> FEATURE:
<223> OTHER INFORMATION: Chemically synthesized
<220> FEATURE:
<221> NAME/KEY: MISC_FEATURE
<222> LOCATION: (10)..(17)
<223> OTHER INFORMATION: Wherein Xaa is any amino acid.
<220> FEATURE:
<221> NAME/KEY: MISC_FEATURE
<222> LOCATION: (23)..(23)
<223> OTHER INFORMATION: Wherein Xaa is any amino acid.

```
<220> FEATURE:
<221> NAME/KEY: MISC_FEATURE
<222> LOCATION: (25)..(31)
<223> OTHER INFORMATION: Wherein Xaa is any amino acid.
<220> FEATURE:
<221> NAME/KEY: MISC_FEATURE
<222> LOCATION: (34)..(34)
<223> OTHER INFORMATION: Wherein Xaa is Ser or Thr.

<400> SEQUENCE: 13

Arg Lys Lys Arg Arg Gln Arg Arg Xaa Xaa Xaa Xaa Xaa Xaa Xaa
1               5                   10                  15

Xaa Arg Pro Thr Thr Leu Xaa Leu Xaa Xaa Xaa Xaa Xaa Xaa Gln
            20                  25                  30

Asp Xaa

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17
<211> LENGTH: 29
<212> TYPE: PRT
<213> ORGANISM: Artificial sequence
<220> FEATURE:
<223> OTHER INFORMATION: Chemically synthesized

<400> SEQUENCE: 17

Pro Gly Thr Gly Cys Gly Asp Thr Tyr Arg Pro Lys Arg Pro Thr Thr
1               5                   10                  15

Leu Asn Leu Phe Pro Gln Val Pro Arg Ser Gln Asp Thr
            20                  25

<210> SEQ ID NO 18
<211> LENGTH: 27
<212> TYPE: PRT
<213> ORGANISM: Artificial sequence
<220> FEATURE:
<223> OTHER INFORMATION: Chemically synthesized

<400> SEQUENCE: 18

Ile Pro Ser Pro Ser Val Glu Glu Pro His Lys His Arg Pro Thr Thr
1               5                   10                  15

Leu Arg Leu Thr Thr Leu Gly Ala Gln Asp Ser
            20                  25

<210> SEQ ID NO 19
<211> LENGTH: 29
<212> TYPE: PRT
<213> ORGANISM: Artificial sequence
<220> FEATURE:
<223> OTHER INFORMATION: Chemically synthesized
```

```
<400> SEQUENCE: 19

Gly Ala Tyr Gly Tyr Ser Asn Pro Lys Ile Leu Lys Gln Ser Met Thr
1               5                   10                  15

Leu Asn Leu Ala Asp Pro Val Gly Asn Leu Lys Pro His
            20                  25

<210> SEQ ID NO 20
<211> LENGTH: 29
<212> TYPE: PRT
<213> ORGANISM: Artificial sequence
<220> FEATURE:
<223> OTHER INFORMATION: Chemically synthesized

<400> SEQUENCE: 20

Thr Asn Glu Asp His Leu Ala Val His Lys His Lys His Glu Met Thr
1               5                   10                  15

Leu Lys Phe Gly Pro Ala Arg Asn Asp Ser Val Ile Val
            20                  25

<210> SEQ ID NO 21
<211> LENGTH: 20
<212> TYPE: PRT
<213> ORGANISM: Artificial sequence
<220> FEATURE:
<223> OTHER INFORMATION: Chemically synthesized

<400> SEQUENCE: 21

Arg Pro Lys Arg Pro Thr Thr Leu Asn Leu Phe Pro Gln Val Pro Arg
1               5                   10                  15

Ser Gln Asp Thr
            20

<210> SEQ ID NO 22

<400> SEQUENCE: 22

000

<210> SEQ ID NO 23
<211> LENGTH: 32
<212> TYPE: PRT
<213> ORGANISM: Artificial sequence
<220> FEATURE:
<223> OTHER INFORMATION: Chemically synthesized

<400> SEQUENCE: 23

Gly Arg Lys Lys Arg Arg Gln Arg Arg Pro Pro Arg Pro Lys Arg
1               5                   10                  15

Pro Thr Thr Leu Asn Leu Phe Pro Gln Val Pro Arg Ser Gln Asp Thr
            20                  25                  30

<210> SEQ ID NO 24

<400> SEQUENCE: 24

000

<210> SEQ ID NO 25
<211> LENGTH: 30
<212> TYPE: PRT
<213> ORGANISM: Artificial sequence
<220> FEATURE:
<223> OTHER INFORMATION: Chemically synthesized
<220> FEATURE:
<221> NAME/KEY: MISC_FEATURE
<222> LOCATION: (10)..(13)
```

```
<223> OTHER INFORMATION: Wherein Xaa is any amino acid.
<220> FEATURE:
<221> NAME/KEY: MISC_FEATURE
<222> LOCATION: (19)..(19)
<223> OTHER INFORMATION: Wherein Xaa is any amino acid.
<220> FEATURE:
<221> NAME/KEY: MISC_FEATURE
<222> LOCATION: (21)..(27)
<223> OTHER INFORMATION: Wherein Xaa is any amino acid.
<220> FEATURE:
<221> NAME/KEY: MISC_FEATURE
<222> LOCATION: (30)..(30)
<223> OTHER INFORMATION: Wherein Xaa is Ser or Thr.

<400> SEQUENCE: 25

Arg Lys Lys Arg Arg Gln Arg Arg Arg Xaa Xaa Xaa Xaa Arg Pro Thr
1               5                   10                  15

Thr Leu Xaa Leu Xaa Xaa Xaa Xaa Xaa Xaa Xaa Gln Asp Xaa
            20                  25                  30

<210> SEQ ID NO 26

<400> SEQUENCE: 26

000

<210> SEQ ID NO 27
<211> LENGTH: 20
<212> TYPE: PRT
<213> ORGANISM: Artificial sequence
<220> FEATURE:
<223> OTHER INFORMATION: Chemically synthesized

<400> SEQUENCE: 27

Arg Pro Lys Arg Pro Thr Ala Ala Asn Ala Phe Pro Gln Val Pro Arg
1               5                   10                  15

Ser Gln Asp Thr
            20

<210> SEQ ID NO 28

<400> SEQUENCE: 28

000

<210> SEQ ID NO 29
<211> LENGTH: 21
<212> TYPE: DNA
<213> ORGANISM: Artificial sequence
<220> FEATURE:
<223> OTHER INFORMATION: Description of Artificial Sequence:
      oligonucleotide probe

<400> SEQUENCE: 29
cgcttgatga gtcagccgga a                                            21

<210> SEQ ID NO 30
<211> LENGTH: 20
<212> TYPE: DNA
<213> ORGANISM: Artificial sequence
<220> FEATURE:
<223> OTHER INFORMATION: Description of Artificial Sequence:
      oligonucleotide primer

<400> SEQUENCE: 30
gctgacagat acactccaag                                              20

<210> SEQ ID NO 31
```

```
<211> LENGTH: 20
<212> TYPE: DNA
<213> ORGANISM: Artificial sequence
<220> FEATURE:
<223> OTHER INFORMATION: Description of Artificial Sequence:
      oligonucleotide primer

<400> SEQUENCE: 31
cctagatgat gccggaaaca                                             20

<210> SEQ ID NO 32
<211> LENGTH: 20
<212> TYPE: DNA
<213> ORGANISM: Artificial sequence
<220> FEATURE:
<223> OTHER INFORMATION: Description of Artificial Sequence:
      oligonucleotide primer

<400> SEQUENCE: 32
aacggctccg gcatgtgcaa                                             20

<210> SEQ ID NO 33
<211> LENGTH: 21
<212> TYPE: DNA
<213> ORGANISM: Artificial sequence
<220> FEATURE:
<223> OTHER INFORMATION: Description of Artificial Sequence:
      oligonucleotide primer

<400> SEQUENCE: 33
attgtagaag gtgtggtgcc a                                           21
```